(12) United States Patent
Kamatani et al.

(10) Patent No.: US 6,953,628 B2
(45) Date of Patent: Oct. 11, 2005

(54) LUMINESCENCE DEVICE AND DISPLAY APPARATUS

(75) Inventors: Jun Kamatani, Kawasaki (JP); Shinjiro Okada, Isehara (JP); Akira Tsuboyama, Sagamihara (JP); Takao Takiguchi, Tokyo (JP); Seishi Miura, Sagamihara (JP); Koji Noguchi, Sagamihara (JP); Takashi Moriyama, Kawasaki (JP); Manabu Furugori, Atsugi (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 10/073,011

(22) Filed: Feb. 12, 2002

(65) Prior Publication Data

US 2003/0059646 A1 Mar. 27, 2003

Related U.S. Application Data

(63) Continuation of application No. PCT/JP01/10477, filed on Nov. 30, 2001.

(30) Foreign Application Priority Data

Nov. 30, 2000 (JP) ........................................ 2000-364650
Mar. 8, 2001 (JP) ........................................ 2001-064203

(51) Int. Cl.[7] .............................................. H05B 33/14
(52) U.S. Cl. ....................... 428/690; 428/917; 313/504; 313/506; 257/102; 257/103
(58) Field of Search .................................. 428/690, 917; 313/504, 506; 257/102, 103; 546/4, 10

(56) References Cited

U.S. PATENT DOCUMENTS

| | | | |
|---|---|---|---|
| 2001/0019782 A1 | 9/2001 | Igarashi et al. | ............. 428/690 |
| 2002/0024293 A1 * | 2/2002 | Igarashi et al. | ............. 313/483 |
| 2002/0055014 A1 * | 5/2002 | Okada et al. | ............... 428/690 |
| 2002/0121638 A1 * | 9/2002 | Grushin et al. | ............... 257/40 |
| 2002/0197511 A1 * | 12/2002 | D'Andrade et al. | ........ 428/690 |
| 2003/0068536 A1 | 4/2003 | Tsuboyama et al. | ........ 428/704 |

FOREIGN PATENT DOCUMENTS

| | | |
|---|---|---|
| JP | 5-78655 | 3/1993 |
| JP | 5-320633 | 12/1993 |
| JP | 2001-247859 | 9/2001 |
| JP | 2001-345183 | 12/2001 |
| WO | WO 02/02714 A2 | 1/2002 |

OTHER PUBLICATIONS

D.F. O'Brien et al., "Improved Energy Transfer in Electrophosphorescent Devices," 74(3) *Applied Phys. Lett.* 442–444 (Jan. 1999).

M.A. Baldo et al. "Very High–Efficiency Green Organic Light–Emitting Devices Based on Electrophosphorescence," 75 (1) *Applied Phys. Lett.* 4–6 (Jul. 1999).

P.S. Vincett et al., "Electrical Conduction and Low Voltage Blue Electroluminescence in Vacuum–Deposited Organic Films," 94 *Thin Solid Films* 171–183 (Aug. 1982).

Mirco G. Colombo et al., "Facial Tris Cyclometalated $Rh^{3+}$ and $Ir^{3+}$ Complexes: Their Synthesis, Structure, and Optical Spectroscopic Properties," 33 *Inorg. Chem.* 545–550 (1994) (no month).

C.H. Chen et al., "Recent Developments in Molecular Organic Electroluminescent Materials," 125 *Macromol Symp.* 1–48 (1997) (no month).

M.A. Baldo et al., "Highly Efficient Phosphorescent Emission From Organic Electroluminescent Devices," *Nature* 151–154 (Sep. 1998).

Tetsuo Tsutsui et al., "High Quantum Efficiency in Organic Light–Emitting Devices with Iridium–Complex as a Triplet Emissive Center," 38 *Jpn. J. Appl. Phys.* L1502–L1504 (Dec. 1999).

* cited by examiner

Primary Examiner—Marie Yamnitzky
(74) Attorney, Agent, or Firm—Fitzpatrick, Cella, Harper & Scinto

(57) ABSTRACT

In a luminescence device formed of one or plural layers of organic film between a cathode and an anode, at least one layer is a luminescence layer, and a luminescence molecule of a metal coordination compound having a basic structure represented by formula (1) $ML_mL'_n$ and having a substituent on at least one of cyclic groups incorporated as a guest in a host material at a concentration of at least 8 wt. %, which is higher than a concentration at which a luminescence molecule of a similar structure but having no substituent exhibits a maximum luminescence efficiency to form the luminescence layer. As a result, a high-efficiency luminescence device is provided, which is less likely to cause concentration extinction even when a luminescence molecule is contained at a high concentration relative to the host material in the luminescence layer.

3 Claims, 5 Drawing Sheets

LUMINESCENCE DEVICE AND DISPLAY APPARATUS

This application is a continuation of International Application No. PCT/JP01/10477, filed Nov. 30, 2001.

TECHNICAL FIELD

The present invention relates to an organic film luminescence device for use in a planar light source, a planar display, etc.

The present invention relates to a luminescence device using an organic compound, more particularly to a high-efficiency luminescence device containing in its luminescence layer a luminescence material comprising a metal coordination compound less liable to cause concentration extinction even when used at a high concentration.

BACKGROUND ART

An old example of organic luminescence device is, e.g., one using luminescence of a vacuum-deposited anthracene film (Thin Solid Films, 94 (1982) 171). In recent years, however, in view of the advantages such as easiness of providing a large-area device compared with an inorganic luminescence device and a possibility of obtaining desired luminescence colors in view of the development of various new materials and drivability at low voltages, an extensive study related to forming a luminescence device of a high-speed responsiveness and a high efficiency has been conducted.

As described in detail in, e.g., Macromol. Symp. 125, 1–48 (1997), an organic EL device generally has a structure comprising upper and lower electrodes and a plurality of organic film layers between the electrodes formed on a transparent substrate. Basic structures thereof are shown in FIGS. 1(a) and (b).

As shown in FIG. 1, an organic EL device generally has a structure comprising a transparent electrode 14, a metal electrode 11, and a plurality of organic film layers therebetween on a transparent substrate 15.

In the device of FIG. 1(a), the organic layers comprise a luminescence layer 12 and a hole-transporting layer 13. For the transparent electrode 14, ITO, etc., having a large work function are used, for providing a good hole-injection characteristic from the transparent electrode 14 to the hole-transporting layer 13. For the metal electrode 11, a metal, such as aluminum, magnesium or an alloy of these, having a small work function is used for providing a good electron-injection characteristic. These electrodes have a thickness of 50–200 nm.

For the luminescence layer 12, aluminum quinolynol complexes (a representative example thereof is Alq3 shown hereinafter), etc., having an electron-transporting characteristic and luminescence characteristic are used. For the hole-transporting layer, biphenyldiamine derivatives (a representative example thereof is .alpha.-NPD shown hereinafter), etc., having an electron-donative characteristic are used.

The above-structured device has a rectifying characteristic, and when an electric field is applied between the metal electrode 11 as a cathode and the transparent electrode 14 as an anode, electrons are injected from the metal electrode 11 into the luminescence layer 12 and holes are injected from the transparent electrode 15. The injected holes and electrons are recombined within the luminescence layer 12 to form excitons and cause luminescence. At this time, the hole-transporting layer 13 functions as an electron-blocking layer to increase the recombination efficiency at a boundary between the luminescence layer 12 and hole-transporting layer 13, thereby increasing the luminescence efficiency.

Further, in the structure of FIG. 1(b), an electron-transporting layer 16 is disposed between the metal electrode 11 and the luminescence layer 12. By separating the luminescence and the electron and hole-transportation to provide a more effective carrier blocking structure, effective luminescence can be performed. For the electron-transporting layer 16, an electron-transporting material, such as an oxadiazole derivative, is used.

Known luminescence processes used heretofore in organic EL devices include utilizing an excited singlet state and utilizing an excited triplet state, and the transition from the former state to the ground state is called "fluorescence" and the transition from the latter state to the ground state is called "phosphorescence". And the substances in these excited states are called a singlet exciton and a triplet exciton, respectively.

In most of the organic luminescence devices studied heretofore, fluorescence caused by the transition from the excited singlet state to the ground state has been utilized. On the other hand, in recent years, devices utilizing phosphorescence via triplet excitons have been studied.

Representative published literature may include:

Article 1: Improved energy transfer in electrophosphorescent device (D. F. O'Brien, et al., Applied Physics Letters, Vol. 74, No. 3, p. 422 (1999)); and Article 2: Very high-efficiency green organic light-emitting devices based on electrophosphorescence (M. A. Baldo, et al., Applied Physics Letters, Vol. 75, No. 1, p. 4 (1999)).

In these articles, a structure including 4 organic layers devices as shown in FIG. 1(c) has been principally used, including, from the anode side, a hole-transporting layer 13, a luminescence layer 12, an exciton diffusion-prevention layer 17 and an electron-transporting layer 11. Materials used therein include carrier-transporting materials and phosphorescent materials, of which the names and structures are shown below together with their abbreviations.

Alq3: aluminum quinolinol complex

α-NPD: N4,N4'-di-naphthalene-1-yl-N4,N4'-diphenyl-biphenyl-4,4'-diamine

CBP: 2,9-dimethyl-4,7-diphenyl-1,10-phenanthroline

PtOEP: platinum-octaethylporphyrin complex

Ir(ppy)$_3$: iridium-phenylpyridine complex

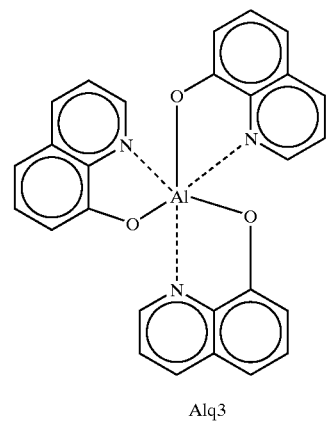

Alq3

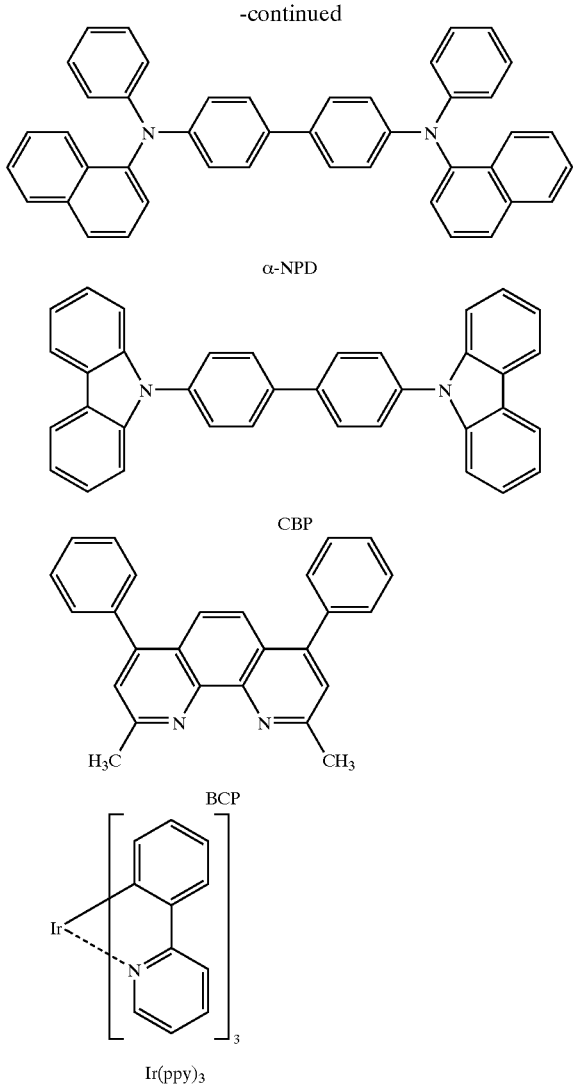

α-NPD

CBP

BCP

Ir(ppy)₃

The above-mentioned Articles 1 and 2 both have reported structures as exhibiting a high efficiency, including a hole-transporting layer 13 comprising α-NPD, an electron-transporting layer 16 comprising Alq3, an exciton diffusion-preventing layer 17 comprising BCP, and a luminescence layer 12 comprising CBP as a host and ca. 6% of platinum-octaethylporphyrin complex (PtOEP) or iridium-phenylpyrimidine complex (Ir(ppy)₃) as a phosphorescent material dispersed in mixture therein.

Such a phosphorescent material is particularly noted at present because it is expected to provide a high luminescence efficiency in principle for the following reasons. More specifically, excitons formed by a carrier recombination comprise singlet excitons and triplet excitons in a probability ratio of 1:3. Conventional organic EL devices have utilized fluorescence of which the luminescence efficiency is limited to at most 25%. On the other hand if phosphorescence generated from triplet excitons is utilized, an efficiency of at least three times is expected, and even an efficiency of 100%, i.e., four times, can be expected in principle, if a transition owing to the intersystem crossing from a singlet state having a higher energy to a triplet state is taken into account.

However, like a fluorescent-type device, such an organic luminescence device utilizing phosphorescence is generally required to be further improved regarding the deterioration of luminescence efficiency and device stability.

The reason for the deterioration has not been fully clarified, but the present inventors consider it to be as follows based on the mechanism of phosphorescence.

In the case where the luminescence layer comprises a host material having a carrier-transporting function and a phosphorescent guest material, a process of phosphorescence via triplet excitons may include unit processes as follows:

1. transportation of electrons and holes within a luminescence layer,
2. formation of host excitons,
3. excitation energy transfer between host molecules,
4. excitation energy transfer from the host to the guest,
5. formation of guest triplet excitons, and
6. transition of the guest triplet excitons to the ground state and phosphorescence.

Desirable energy transfer in each unit process and luminescence are caused in competition with various energy deactivation processes.

Particularly, in a phosphorescent material, this may be attributable to a life of the triplet excitons, which is longer by three or more digits than the life of a singlet exciton. More specifically, because it is held in a high-energy excited state for a longer period, it is likely to react with surrounding materials and cause polymer formation among the excitons, thus incurring a higher probability of a deactivation process resulting in a material change or life deterioration, as we have considered.

Needless to say, a luminescence efficiency of an organic luminescence device is increased by increasing the luminescence quantum yield of a luminescence center material, but it is also an important factor for enhancing the luminescence intensity of the device to increase the concentration of a luminescence material in the luminescence layer.

The luminescence intensity is increased in proportion to the concentration of a luminescence material in a luminescence layer in the case of a low concentration (up to several wt. %) of the luminescence material in the luminescence layer. However, above several % or 7%, a deviation from the proportional relationship is observed, and the luminescence intensity is rather lowered to result in a worse efficiency. This phenomenon is reported in Japanese Laid-Open Patent Application (JP-A) 05-078655, JP-A 05-320633, etc., and is known as concentration extinction or concentration deactivation.

Actually, in the case of using Ir(ppy)₃ in CBP as the host material, the best luminescence efficiency is attained at a concentration of ca. 6–7%, and the luminescence efficiency is rather lowered thereabove, down to about a half at 12% concentration and 1/10 or below at 100% concentration (Applied Physics Letters 4, vol. 75, 1999).

The phenomenon is caused by abundant presence of molecules in the triplet excited state waiting for luminescence in the case of a phosphorescence substance having a life of triplet exciton longer by 3 digits or more than the life of the singlet exciton. In this state, thermal deactivation of losing energy due to a mutual interaction of triplet excitons is likely to occur. This is called triplet-triplet extinction and is associated with a lowering in luminescence efficiency at a high current density. Further, it is also considered that due to a long retention time at a high energy state, the excitons have an increased probability of reacting with a surrounding material and forming polymers of excitons, thereby causing deactivation, or even leading to a material change or a deterioration of life.

DISCLOSURE OF INVENTION

An object of the present invention is to provide an organic luminescence device of a higher luminescence intensity by suppressing the above-mentioned concentration extinction phenomenon and providing an environment of using a luminescence material at a higher concentration.

More specifically, an object of the present invention is to provide a luminescence material less likely to lead to concentration extinction even when used at a high concentration with respect to the host material in a luminescence layer by introducing a substituent group into a metal coordination compound as such a luminescence material.

A more specific object of the present invention is to provide an organic luminescence device capable of a large luminescence intensity, that is an organic luminescence device, comprising: a pair of electrodes each disposed on a substrate, and at least one luminescence layer comprising an organic compound disposed between the electrodes; wherein the luminescence layer comprises a non-luminescent first organic compound and a phosphorescent second organic compound represented by formula (1) shown below, and the second organic compound is present at a concentration of at least 8 wt. % in the luminescence layer:

  (1), wherein M is a metal atom of Ir, Pt, Rh or Pd; L and L' are mutually different bidentate ligands; m is 1, 2 or 3; n is 0, 1 or 2 with the proviso that m+n is 2 or 3; a partial structure $ML_m$ is represented by formula (2) shown below and a partial structure $ML'_n$ is represented by formula (3), (4) or (5) shown below:

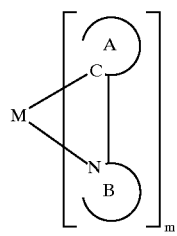 (2)

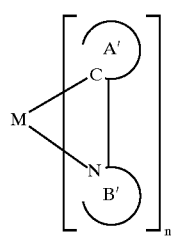 (3)

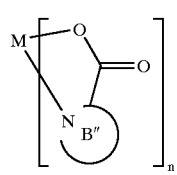 (4)

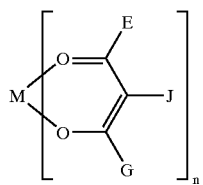 (5)

wherein N and C are nitrogen and carbon atoms, respectively; A and A' are respectively a cyclic group capable of having a substituent and bonded to the metal atom M via the carbon atom; B, B' and B" are respectively a cyclic group represented by a formula of (6)–(14) shown below capable of having a substituent and connected to the metal atom M via the nitrogen atom:

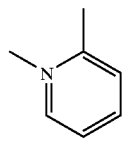 6

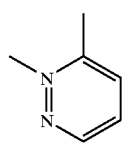 7

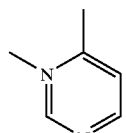 8

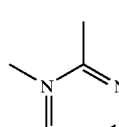 9

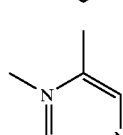 10

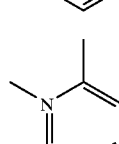 11

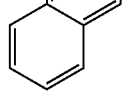 12

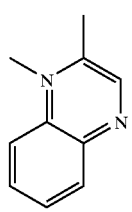

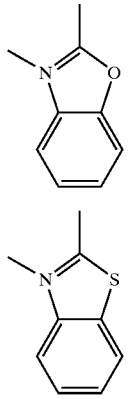

According to another aspect, the organic luminescence device of the present invention is a luminescence device comprising at least one layer of organic film disposed between a cathode and an anode and including at least one luminescence layer, that is characterized by containing a luminescence molecule of the formula (1) having a substituent and showing a maximum luminescence characteristic at a concentration higher than a concentration at which a luminescence molecule of a similar structure but having no substituent shows a maximum luminescence efficiency.

More specifically, in a luminescence device comprising at least one organic film layer between a cathode and an anode, including at least one luminescence layer, it is preferred that a luminescence molecule of the formula (1) including at least one cyclic group having a substituent is contained at a concentration higher than a concentration at which a luminescence molecule of a similar structure shows a maximum luminescence efficiency.

BEST MODE FOR PRACTICING THE INVENTION

Basic device structures according to the present invention are similar to those shown in FIGS. 1(a), (b) and (c).

Figure 1:
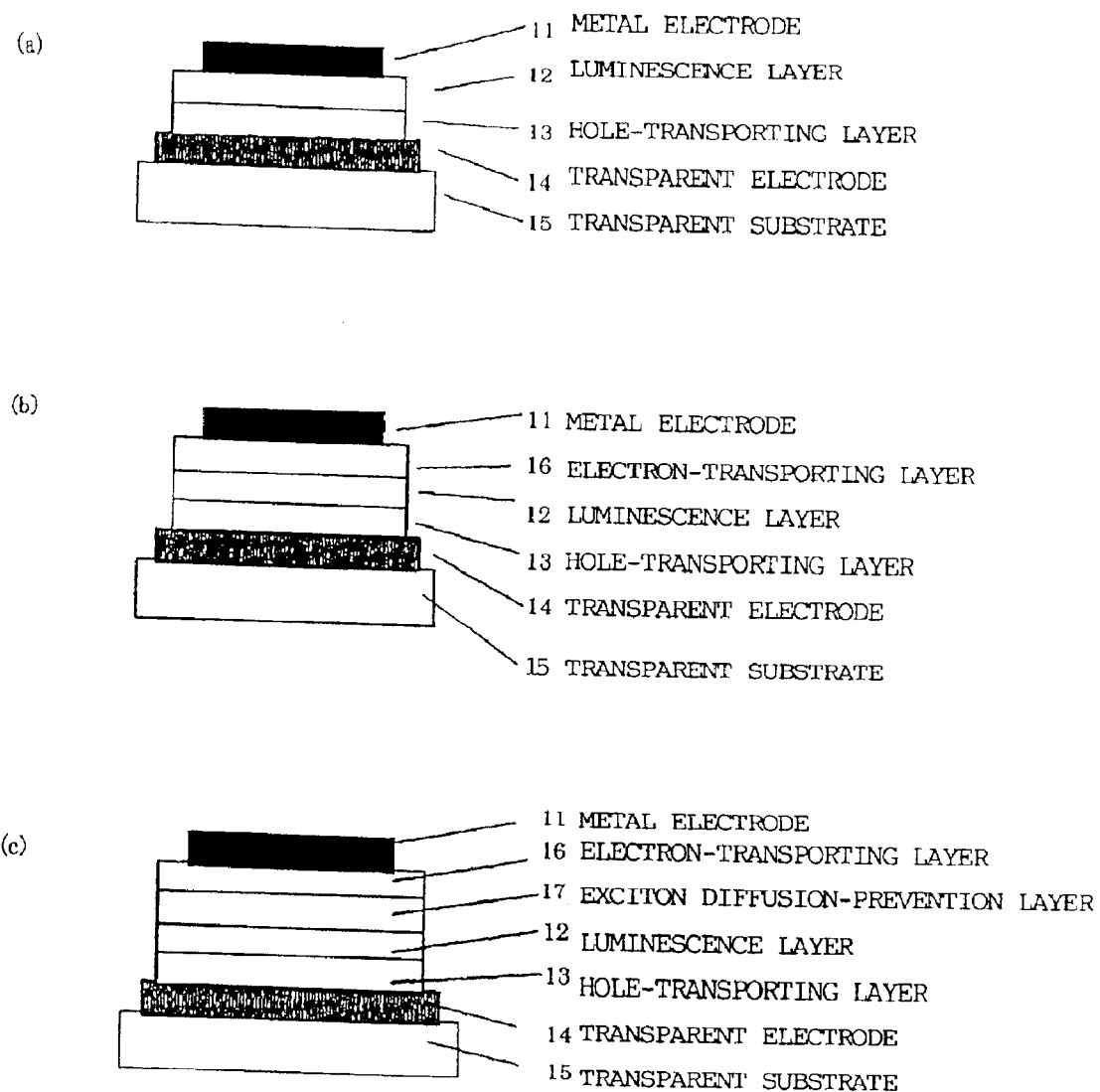
FIG. 1 illustrates embodiments of the luminescence device according to the present invention.

More specifically, as shown in FIG. 1, an organic luminescence device generally comprises, on a transparent electrode 15, a 50 to 200 nm-thick transparent electrode 14, a plurality of organic film layers and a 10 to 500 nm-thick metal electrode 11 formed so as to sandwich the organic layers.

FIG. 1(a) shows an embodiment wherein the organic luminescence device comprises a luminescence layer 12 and a hole-transporting layer 13. The transparent electrode 14 may comprise ITO, etc., having a large work function so as to facilitate hole injection from the transparent electrode 14 to the hole-transporting layer 13. The metal electrode 11 comprises a metal material having a small work function, such as aluminum, magnesium or alloys of these elements, so as to facilitate electron injection into the organic luminescence device.

The luminescence layer 12 comprises a compound according to the present invention. The hole-transporting layer 13 may comprise, e.g., a triphenyldiamine derivative, as represented by α-NPD mentioned above, and also a material having an electron-donative property as desired.

A device organized above exhibits a current-rectifying characteristic, and when an electric field is applied between the metal electrode 11 as a cathode and the transparent electrode 14 as an anode, electrons are injected from the metal electrode 11 into the luminescence layer 12, and holes are injected from the transparent electrode 15. The injected holes and electrons are recombined in the luminescence layer 12 to form excitons, which cause luminescence. In this instance, the hole-transporting layer 13 functions as an electron-blocking layer to increase the recombination efficiency at the boundary between the luminescence layer layer 12 and the hole-transporting layer 13, thereby providing an enhanced luminescence efficiency.

Further, in the structure of FIG. 1(b), an electron-transporting layer 16 is disposed between the metal electrode 11 and the luminescence layer 12 in FIG. 1(a). As a result, the luminescence function is separated from the functions of electron transportation and hole transportation to provide a structure exhibiting more effective carrier blocking, thus increasing the luminescence efficiency. The electron-transporting layer 16 may comprise, e.g., an oxadiazole derivative.

FIG. 1(c) shows another desirable form of a four-layer structure, including a hole-transporting layer 13, a luminescence layer 12, an exciton diffusion prevention layer 17 and an electron-transporting layer 16, successively from the side of the transparent electrode 14 as an anode.

Each of the organic film layers 12, 13, 16 and 17 is formed in a thickness of at most 200 nm, and particularly the luminescence layer 12 is formed in a thickness of 5–200 nm.

The present inventors have discovered that the use of a metal coordination compound including a substituted cyclic group and represented by the above-mentioned formula (1) results in a high efficiency luminescence and a lesser likelihood of concentration extinction even at a high concentration than the conventional level due to suppression of an inter-molecular interaction.

It has been also found that the suppression of concentration extinction is an effect attributable to a substituent on the metal coordination compound, and the concentration extinction becomes less likely to occur not regardless of the coordination number of ligands but owing to the presence of a substituent on at least one ligand.

Particularly, as a result, in a conventional phosphorescence-type organic EL device, the luminescence material can be used at a high concentration of 8% or higher in the luminescence layer, thereby providing an organic EL device exhibiting a high luminescence luminance.

The metal coordination compound used in the present invention emits phosphorescence, and its lowest excited state is believed to be an MLCT* (metal-to-ligand charge transfer) excited state or π-π* excited state in a triplet state, and phosphorescence is caused at the time of transition from such a state to the ground state.

It is generally said that phosphorescence life is shorter at MLCT* than at π-π*, but the molecular structure suppressing the concentration extinction used in the present invention is effective for both MLCT* and π-π* as the lowest excited state, and the molecule can be doped at a high concentration in the luminescence layer in either case.

The luminescence material of the present invention exhibited a high phosphorescence yield of from 0.1 to 0.9 and a short phosphorescence life of 0.1–30 μsec. The phosphorescence yield referred to herein is a relative quantum yield, i.e., a ratio of an objective sample's quantum yield Φ(sample) to a standard sample's quantum yield Φ(st)) and is determined according to the following formula:

Φ(sample)/Φ(st)=[$Sem$(sample)/$Iabs$(sample)]/[$Sem(st)/Iabs(st)$], wherein Iabs(st) denotes an absorption coefficient at an excitation wavelength of the standard sample; Sem(st), a luminescence spectral areal intensity when excited at the same wavelength: Iabs(sample), an absorption coefficient at an excitation wavelength of an objective compound; and Sem(sample), a luminescence spectral areal intensity when excited at the same wavelength.

Phosphorescence yield values described herein are relative values with respect to a phosphorescence yield Φ=1 of Ir(ppy)$_3$ as a standard sample.

Further, the luminescence (phosphorescence) life referred to herein is based on values measured according to the following method.

<<Method of Measurement of Life>>

A sample compound is dissolved in chloroform and spin-coated onto a quartz substrate in a thickness of ca. 0.1 μm and is exposed to pulsative nitrogen laser light at an excitation wavelength of 337 nm at room temperature by using a luminescence life meter (made by Hamamatsu Photonics K.K.). After completion of the excitation pulses, the decay characteristic of luminescence intensity is measured.

When an initial luminescence intensity is denoted by $I_0$, a luminescence intensity after t(sec) is expressed according to the following formula with reference to a luminescence life τ(sec):

$I=I_0 \cdot \exp(-t/\tau)$.

Thus, the luminescence life τ is a time period in which the luminescence intensity I is attenuated down to 1/e of the initial intensity I ($I/I_0=e^{-1}$, e is a base of natural logarithm).

A short phosphorescence life is a condition for providing an EL device of a high luminescence efficiency. More specifically, a long phosphorescence life means abundant presence of molecules in a triplet excited state waiting for the luminescence leading to a problem of a lowering in luminescence efficiency particularly at a high current density. The material of the present invention is a suitable luminescence material for an EL device because of a high phosphorescence yield and a short phosphorescence life. Further, it is assumed that because of a short phosphorescence life, the duration at a triplet state is shortened to suppress the concentration extinction. A high stability of the luminescence material of the present invention was also exhibited in an actual current conduction test of actual devices.

In the case of a phosphorescent material, the luminescence characteristic thereof is severely affected by its molecular environment. In the case of a fluorescence device, the basic property of a luminescence material is examined based on photoluminescence. In the case of phosphorescence, however, the photoluminescence performance does not directly lead to the luminescence performance of an EL device since it is frequently affected by the polarity of host molecules, temperature and solid/liquid state. As a result, EL device performances except for a part thereof cannot be estimated from the photoluminescence result.

In the case of a ligand of the present invention having a cyclic group having one or plural fluorine atoms, it becomes possible to shift the luminescence wavelength to a shorter side or a longer side because of a change in the energy gap. If it is assumed for convenience that HOMO/LUMO of metal electron orbits and HOMO/LUMO of ligand electron orbits can be considered separately, it is understood that HOMO/LUMO energy levels of ligand electron orbits are changed by fluorine atoms having a large electro-negativity to change the energy gap between the HOMO level of the metal and the LUMO level of the ligand, thereby shifting the luminescence from the MLCT state as the lowest excited state to a shorter wavelength side or a longer wavelength side. Accordingly, while a luminescence material exhibiting a stably high quantum yield over a broad wavelength range (blue to red) has not been found, it can be realized by a luminescence material of the present invention, thus being able to provide a luminescence material, which shows a high efficiency at a desired emission wavelength over a broad wavelength range (from blue to red).

When a device is formed, due to a large electronegativity of fluorine atoms, the inter-molecular interaction is suppressed to physically result in a suppressed crystallinity favoring a uniform film formation and physically suppressing the dimerization reaction to prohibit the energy deactivation leading to an improved luminescence efficiency, thus resulting in an improved electrical property and an improved device stability.

Further, in the case of using a ligand containing a plurality of fluorine atoms or polyfluoroalkyl groups as substituents, it is considered that a direct interaction between luminescence molecules is suppressed due to electrical repulsion caused by their electrical effect or due to steric hindrance, thereby preventing energy deactivation and concentration extinction.

Further, from the viewpoint of device preparation, a luminescence material having a substituent, particularly a fluorinated substituent, allows easier vacuum deposition due to a sublimation temperature decrease in the film formation by vacuum deposition, thus providing a great advantage.

As a result, as shown in the Examples hereinafter, by using a luminescence material having a substituent according to the present invention, a stable luminescence for many hours with suppressed concentration extinction can be expected. Further, it becomes possible to attain a high phosphorescence yield over a temperature range of −20° C. to 60° C. as an actual operation temperature range of an organic luminescence device. Further, in the case of using a compound at a concentration of 8 wt. % or higher with respect to a host material in the luminescence layer or at a concentration higher than a compound having no substituent, it becomes possible to provide an EL device exhibiting excellent luminescence performance while suppressing the concentration extinction. The concentration of the luminescence material of the present invention in the luminescence layer may be at least 8 wt. %, preferably 10 wt. % or higher, but the luminescence material potentially has a possibility of being used even at 100% without causing substantial concentration extinction.

Herein, the term "luminescence performance" refers to a characteristic attributable to a maximum luminescence efficiency that can be expressed as any of a maximum luminance, a maximum of luminance/current, a maximum of light flux/power consumption or a maximum of external quantum yield.

A high-efficiency luminescence device according to the present invention is applicable to a product requiring energy economization or a high luminance. More specifically, the luminescence device is applicable to a display apparatus, an illumination apparatus, a printer light source or a backlight for a luminescence layer display apparatus. As for a display apparatus, it allows a flat panel display which is light in weight and provides a highly recognizable display at a low energy consumption. As a printer light source, the luminescence device of the present invention can be used instead of a laser light source of a laser beam printer. Independently addressable devices are arranged in an array form to effect a desired exposure on a photosensitive drum thereby forming an image. The apparatus volume can be remarkably reduced by using the devices of the present invention. For the illumination apparatus or backlight, the energy economization effect according to the present invention can be expected.

For the application to a display, a drive system using a thin-film transistor (abbreviated as TFT) drive circuit according to an active matrix scheme may be used. By driving a display panel using a luminescence material of the present invention in a luminescence layer, it becomes possible to allow a stable display for many hours with a good picture quality.

Hereinbelow, some specific structural formulae of metal coordination compounds represented by the formula (1) used in the present invention are shown in Table 1 appearing hereinafter, which are however only representative examples and are not exhaustive. Ph-P9 used in Table 1 represent partial structures shown below, of which substituents R1, R2, . . . ate shown as A-R1, A-R2, . . . when contained in the cyclic group A in the formula (1) and as B-R1, B-R2, . . . when contained in the cyclic qroup B, . . . in Table 1.

Ph:

Tn1:

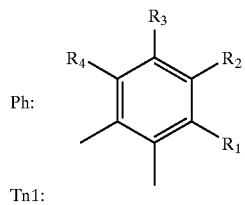

Tn2:

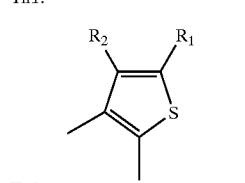

Tn3:

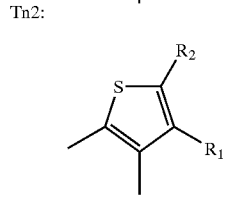

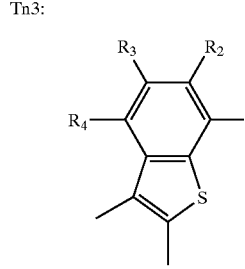

Np1:

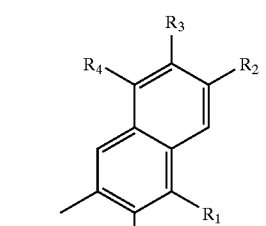

Np2:

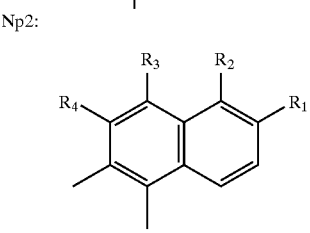

Pe:

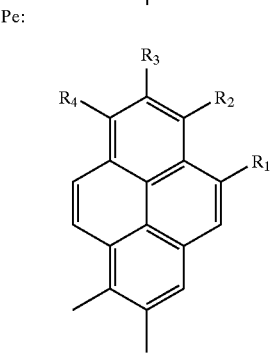

Cn1:

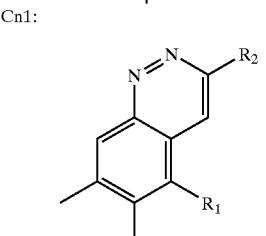

Cn2:

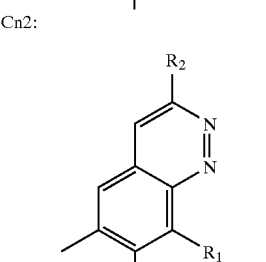

Fl:

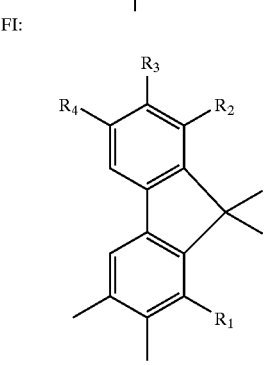

-continued
Qn1:
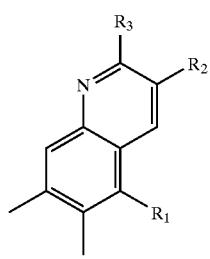
Qn2:
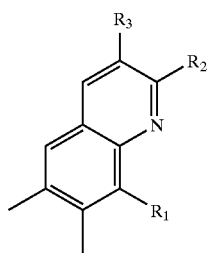
Cz:
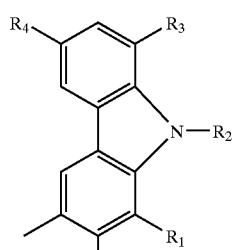
Fn1:
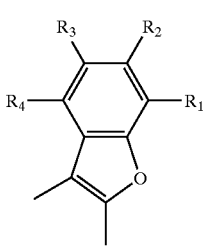
P1
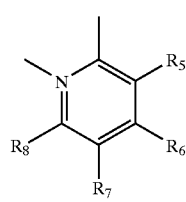
P2
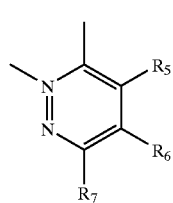
P3
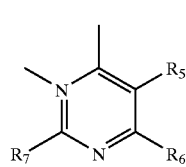
-continued
P4
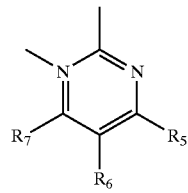
P5
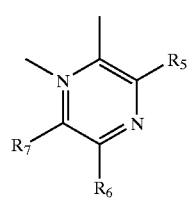
P6
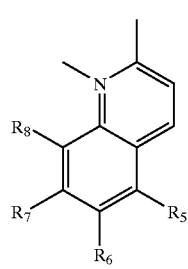
P7
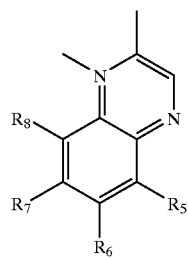
P8
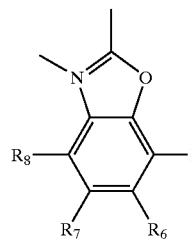
P9
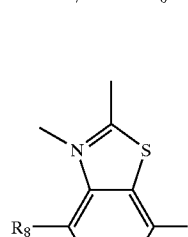
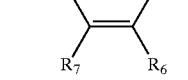

TABLE 1-1

| No | M | m | n | A | B | A-R1 | A-R2 | A-R3 | A-R4 | B-R5 | B-R6 | B-R7 | B-R8 |
|---|---|---|---|---|---|---|---|---|---|---|---|---|---|
| 1 | Ir | 3 | 0 | Ph | P1 | CH3 | H | H | H | H | H | H | H |
| 2 | Ir | 3 | 0 | Ph | P1 | H | CH3 | H | H | H | H | H | H |
| 3 | Ir | 3 | 0 | Ph | P1 | H | H | CH3 | H | H | H | H | H |
| 4 | Ir | 3 | 0 | Ph | P1 | H | H | H | CH3 | H | H | H | H |
| 5 | Ir | 3 | 0 | Ph | P1 | C2H5 | H | H | H | H | H | H | H |
| 6 | Ir | 3 | 0 | Ph | P1 | H | C2H5 | H | H | H | H | H | H |
| 7 | Ir | 3 | 0 | Ph | P1 | H | H | C2H5 | H | H | H | H | H |
| 8 | Ir | 3 | 0 | Ph | P1 | H | H | H | C2H5 | H | H | H | H |
| 9 | Ir | 3 | 0 | Ph | P1 | C3H7 | H | H | H | H | H | H | H |
| 10 | Ir | 3 | 0 | Ph | P1 | H | C3H7 | H | H | H | H | H | H |
| 11 | Ir | 3 | 0 | Ph | P1 | H | H | C3H7 | H | H | H | H | H |
| 12 | Ir | 3 | 0 | Ph | P1 | H | H | H | C3H7 | H | H | H | H |
| 13 | Ir | 3 | 0 | Ph | P1 | C4H9 | H | H | H | H | H | H | H |
| 14 | Ir | 3 | 0 | Ph | P1 | H | C4H9 | H | H | H | H | H | H |
| 15 | Ir | 3 | 0 | Ph | P1 | H | H | C4H9 | H | H | H | H | H |
| 16 | Ir | 3 | 0 | Ph | P1 | H | H | H | C4H9 | H | H | H | H |
| 17 | Ir | 3 | 0 | Ph | P1 | C6H13 | H | H | H | H | H | H | H |
| 18 | Ir | 3 | 0 | Ph | P1 | — | C6H13 | H | H | H | H | H | H |
| 19 | Ir | 3 | 0 | Ph | P1 | H | H | C6H13 | H | H | H | H | H |
| 20 | Ir | 3 | 0 | Ph | P1 | H | H | H | C6H13 | H | H | H | H |
| 21 | Ir | 3 | 0 | Ph | P1 | C8H17 | H | H | H | H | H | H | H |
| 22 | Ir | 3 | 0 | Ph | P1 | H | C8H17 | H | H | H | H | H | H |
| 23 | Ir | 3 | 0 | Ph | P1 | H | H | C8H17 | H | H | H | H | H |
| 24 | Ir | 3 | 0 | Ph | P1 | H | H | H | C8H17 | H | H | H | H |
| 25 | Ir | 3 | 0 | Ph | P1 | C12H25 | H | H | H | H | H | H | H |
| 26 | Ir | 3 | 0 | Ph | P1 | H | C12H25 | H | H | H | H | H | H |
| 27 | Ir | 3 | 0 | Ph | P1 | H | H | C12H25 | H | H | H | H | H |
| 28 | Ir | 3 | 0 | Ph | P1 | H | H | H | C12H25 | H | H | H | H |
| 29 | Ir | 3 | 0 | Ph | P1 | C15H31 | H | H | H | H | H | H | H |
| 30 | Ir | 3 | 0 | Ph | P1 | H | C15H31 | H | H | H | H | H | H |
| 31 | Ir | 3 | 0 | Ph | P1 | H | H | C15H31 | H | H | H | H | H |
| 32 | Ir | 3 | 0 | Ph | P1 | H | H | CH3O | H | H | H | H | H |
| 33 | Ir | 3 | 0 | Ph | P1 | H | H | C2H5O | H | H | H | H | H |
| 34 | Ir | 3 | 0 | Ph | P1 | H | H | C4H9O | H | H | H | H | H |
| 35 | Ir | 3 | 0 | Ph | P1 | H | C4H9O | H | H | H | H | H | H |
| 36 | Ir | 3 | 0 | Ph | P1 | H | N-methylcarbazole | H | H | H | H | H | H |
| 37 | Ir | 3 | 0 | Ph | P1 | H | N-methyldiphenylamine | H | H | H | H | H | H |
| 38 | Ir | 3 | 0 | Ph | P1 | H | H | N-methylcarbazole | H | H | H | H | H |
| 39 | Ir | 3 | 0 | Ph | P1 | H | H | N-methyldiphenylamine | H | H | H | H | H |
| 40 | Ir | 3 | 0 | Ph | P1 | H | H | CF3O | H | H | H | H | H |
| 41 | Ir | 3 | 0 | Ph | P1 | H | H | C4F9 | H | H | H | H | H |
| 42 | Ir | 3 | 0 | Ph | P1 | H | C4F9 | H | H | H | H | H | H |
| 43 | Ir | 3 | 0 | Ph | P1 | H | H | C2F5CH2O | H | H | H | H | H |
| 44 | Ir | 3 | 0 | Ph | P1 | H | C2F5 | H | H | H | H | H | H |
| 45 | Ir | 3 | 0 | Ph | P1 | H | H | C2F5 | H | H | H | H | H |
| 46 | Ir | 3 | 0 | Ph | P1 | H | H | C5F11 | H | H | H | H | H |
| 47 | Ir | 3 | 0 | Ph | P1 | H | H | C8F17 | H | H | H | H | H |
| 48 | Ir | 3 | 0 | Ph | P1 | H | H | C2F5C2H4 | H | H | H | H | H |
| 49 | Ir | 3 | 0 | Ph | P1 | CH3 | H | CH3 | H | H | H | H | H |

TABLE 1-1-continued

| No | M | m | n | A | B | A-R1 | A-R2 | A-R3 | A-R4 | B-R5 | B-R6 | B-R7 | B-R8 |
|----|----|---|---|----|----|------|------|------|------|------|------|------|------|
| 50 | Ir | 3 | 0 | Ph | P1 | H | CH3 | CH3 | H | H | H | H | H |
| 51 | Ir | 3 | 0 | Ph | P1 | C2H5 | H | C2H5 | H | H | H | H | H |
| 52 | Ir | 3 | 0 | Ph | P1 | C4H9 | H | C4H9 | H | H | H | H | H |
| 53 | Ir | 3 | 0 | Ph | P1 | H | C4H9 | H | H | H | H | H | H |
| 54 | Ir | 3 | 0 | Ph | P1 | H | H | H | H | CH3 | H | H | H |
| 55 | Ir | 3 | 0 | Ph | P1 | H | H | H | H | H | CH3 | H | H |
| 56 | Ir | 3 | 0 | Ph | P1 | H | H | H | H | H | H | CH3 | H |
| 57 | Ir | 3 | 0 | Ph | P1 | H | H | H | H | H | H | H | CH3 |
| 58 | Ir | 3 | 0 | Ph | P1 | H | H | H | H | C4H9 | H | H | H |
| 59 | Ir | 3 | 0 | Ph | P1 | H | H | H | H | H | C4H9 | H | H |
| 60 | Ir | 3 | 0 | Ph | P1 | H | H | H | H | H | H | C4H9 | H |

TABLE 1-2

| No | M | m | n | A | B | A-R1 | A-R2 | A-R3 | A-R4 | B-R5 | B-R6 | B-R7 | B-R8 |
|-----|----|---|---|----|----|------|------|------|------|------|------|------|------|
| 61 | Ir | 3 | 0 | Ph | P1 | H | H | H | H | H | H | H | C4H9 |
| 62 | Ir | 3 | 0 | Ph | P1 | H | H | H | H | C8H17 | H | H | H |
| 63 | Ir | 3 | 0 | Ph | P1 | H | H | H | H | H | C8H17 | H | H |
| 64 | Ir | 3 | 0 | Ph | P1 | H | H | H | H | H | H | C8H17 | H |
| 65 | Ir | 3 | 0 | Ph | P1 | H | H | H | H | H | H | H | C8H17 |
| 66 | Ir | 3 | 0 | Ph | P1 | CH3 | H | H | H | CH3 | H | H | H |
| 67 | Ir | 3 | 0 | Ph | P1 | CH3 | H | H | H | H | CH3 | H | H |
| 68 | Ir | 3 | 0 | Ph | P1 | CH3 | H | H | H | H | H | CH3 | H |
| 69 | Ir | 3 | 0 | Ph | P1 | CH3 | H | H | H | H | H | H | CH3 |
| 70 | Ir | 3 | 0 | Ph | P1 | H | CH3 | H | H | CH3 | H | H | H |
| 71 | Ir | 3 | 0 | Ph | P1 | H | CH3 | H | H | H | CH3 | H | H |
| 72 | Ir | 3 | 0 | Ph | P1 | H | CH3 | H | H | H | H | CH3 | H |
| 73 | Ir | 3 | 0 | Ph | P1 | H | CH3 | H | H | H | H | H | CH3 |
| 74 | Ir | 3 | 0 | Ph | P1 | H | H | CH3 | H | CH3 | H | H | H |
| 75 | Ir | 3 | 0 | Ph | P1 | H | H | CH3 | H | H | CH3 | H | H |
| 76 | Ir | 3 | 0 | Ph | P1 | H | H | CH3 | H | H | H | CH3 | H |
| 77 | Ir | 3 | 0 | Ph | P1 | H | H | CH3 | H | H | H | H | CH3 |
| 78 | Ir | 3 | 0 | Ph | P1 | H | H | H | CH3 | H | H | CH3 | H |
| 79 | Ir | 3 | 0 | Ph | P1 | C2H5 | H | H | H | H | CH3 | H | H |
| 80 | Ir | 3 | 0 | Ph | P1 | C2H5 | H | H | H | H | CH3 | H | H |
| 81 | Ir | 3 | 0 | Ph | P1 | H | C2H5 | H | H | CH3 | H | H | H |
| 82 | Ir | 3 | 0 | Ph | P1 | H | C2H5 | H | H | CH3 | H | H | H |
| 83 | Ir | 3 | 0 | Ph | P1 | H | C2H5 | H | H | H | H | CH3 | H |
| 84 | Ir | 3 | 0 | Ph | P1 | H | C2H5 | H | H | H | H | H | CH3 |
| 85 | Ir | 3 | 0 | Ph | P1 | H | H | C2H5 | H | CH3 | H | H | H |
| 86 | Ir | 3 | 0 | Ph | P1 | H | H | C2H5 | H | H | CH3 | H | H |
| 87 | Ir | 3 | 0 | Ph | P1 | H | H | C2H5 | H | H | H | CH3 | H |
| 88 | Ir | 3 | 0 | Ph | P1 | H | H | C2H5 | H | H | H | H | CH3 |
| 89 | Ir | 3 | 0 | Ph | P1 | H | H | H | C2H5 | H | CH3 | H | H |
| 90 | Ir | 3 | 0 | Ph | P1 | H | H | H | C2H5 | H | H | CH3 | H |
| 91 | Ir | 3 | 0 | Ph | P1 | C4H9 | H | H | H | H | CH3 | H | H |
| 92 | Ir | 3 | 0 | Ph | P1 | H | C4H9 | H | H | CH3 | H | H | H |
| 93 | Ir | 3 | 0 | Ph | P1 | H | C4H9 | H | H | H | CH3 | H | H |
| 94 | Ir | 3 | 0 | Ph | P1 | H | C4H9 | H | H | H | H | CH3 | H |
| 95 | Ir | 3 | 0 | Ph | P1 | H | C4H9 | H | H | H | H | H | CH3 |
| 96 | Ir | 3 | 0 | Ph | P1 | H | H | C4H9 | H | CH3 | H | H | H |
| 97 | Ir | 3 | 0 | Ph | P1 | H | H | C4H9 | H | H | H | CH3 | H |
| 98 | Ir | 3 | 0 | Ph | P1 | H | H | H | C4H9 | CH3 | H | H | H |
| 99 | Ir | 3 | 0 | Ph | P1 | H | H | H | C4H9 | H | CH3 | H | H |
| 100 | Ir | 3 | 0 | Ph | P1 | C6H13 | H | H | H | H | CH3 | H | H |
| 101 | Ir | 3 | 0 | Ph | P1 | H | C6H13 | H | H | CH3 | H | H | H |
| 102 | Ir | 3 | 0 | Ph | P1 | H | C6H13 | H | H | H | CH3 | H | H |
| 103 | Ir | 3 | 0 | Ph | P1 | H | C6H13 | H | H | H | H | CH3 | H |
| 104 | Ir | 3 | 0 | Ph | P1 | H | C6H13 | H | H | H | H | H | CH3 |
| 105 | Ir | 3 | 0 | Ph | P1 | H | H | C6H13 | H | CH3 | H | H | H |
| 106 | Ir | 3 | 0 | Ph | P1 | H | H | C6H13 | H | H | H | CH3 | H |
| 107 | Ir | 3 | 0 | Ph | P1 | H | H | C6H13 | H | CH3 | H | H | H |
| 108 | Ir | 3 | 0 | Ph | P1 | H | H | H | C6H13 | CH3 | H | H | H |
| 109 | Ir | 3 | 0 | Ph | P1 | CH3 | H | H | H | CF3 | H | H | H |
| 110 | Ir | 3 | 0 | Ph | P1 | H | CH3 | H | H | CF3 | H | H | H |
| 111 | Ir | 3 | 0 | Ph | P1 | H | H | CH3 | H | CF3 | H | H | H |
| 112 | Ir | 3 | 0 | Ph | P1 | H | H | CH3 | CF3 | H | H | H | H |
| 113 | Ir | 3 | 0 | Ph | P1 | CH3 | H | H | H | H | CF3 | H | H |
| 114 | Ir | 3 | 0 | Ph | P1 | H | CH3 | H | H | H | CF3 | H | H |
| 115 | Ir | 3 | 0 | Ph | P1 | H | H | CH3 | H | H | CF3 | H | H |

TABLE 1-2-continued

| No | M | m | n | A | B | A-R1 | A-R2 | A-R3 | A-R4 | B-R5 | B-R6 | B-R7 | B-R8 |
|---|---|---|---|---|---|---|---|---|---|---|---|---|---|
| 116 | Ir | 3 | 0 | Ph | P1 | H | H | H | CH3 | H | CF3 | H | H |
| 117 | Ir | 3 | 0 | Ph | P1 | CH3 | H | H | H | H | H | CF3 | H |
| 118 | Ir | 3 | 0 | Ph | P1 | H | CH3 | H | H | H | H | CF3 | H |
| 119 | Ir | 3 | 0 | Ph | P1 | H | H | CH3 | H | H | H | CF3 | H |
| 120 | Ir | 3 | 0 | Ph | P1 | H | H | H | CH3 | H | H | CF3 | H |

TABLE 1-3

| No | M | m | n | A | B | A-R1 | A-R2 | A-R3 | A-R4 | B-R5 | B-R6 | B-R7 | B-R8 |
|---|---|---|---|---|---|---|---|---|---|---|---|---|---|
| 121 | Ir | 3 | 0 | Ph | P1 | CH3 | H | H | H | H | H | H | CF3 |
| 122 | Ir | 3 | 0 | Ph | P1 | H | CH3 | H | H | H | H | H | CF3 |
| 123 | Ir | 3 | 0 | Ph | P1 | H | H | CH3 | H | H | H | H | CF3 |
| 124 | Ir | 3 | 0 | Ph | P1 | H | H | H | CH3 | H | H | H | CF3 |
| 125 | Ir | 3 | 0 | Ph | P1 | CH3 | H | H | H | F | H | H | H |
| 126 | Ir | 3 | 0 | Ph | P1 | H | CH3 | H | H | F | H | H | H |
| 127 | Ir | 3 | 0 | Ph | P1 | H | H | CH3 | H | F | H | H | H |
| 128 | Ir | 3 | 0 | Ph | P1 | H | H | H | CH3 | F | H | H | H |
| 129 | Ir | 3 | 0 | Ph | P1 | CH3 | H | H | H | H | F | H | H |
| 130 | Ir | 3 | 0 | Ph | P1 | H | CH3 | H | H | H | F | H | H |
| 131 | Ir | 3 | 0 | Ph | P1 | H | H | CH3 | H | H | F | H | H |
| 132 | Ir | 3 | 0 | Ph | P1 | H | H | H | CH3 | H | F | H | H |
| 133 | Ir | 3 | 0 | Ph | P1 | CH3 | H | H | H | H | H | F | H |
| 134 | Ir | 3 | 0 | Ph | P1 | H | CH3 | H | H | H | H | F | H |
| 135 | Ir | 3 | 0 | Ph | P1 | H | H | CH3 | H | H | H | F | H |
| 136 | Ir | 3 | 0 | Ph | P1 | H | H | H | CH3 | H | H | F | H |
| 137 | Ir | 3 | 0 | Ph | P1 | CH3 | H | H | H | H | H | H | F |
| 138 | Ir | 3 | 0 | Ph | P1 | H | CH3 | H | H | H | H | H | F |
| 139 | Ir | 3 | 0 | Ph | P1 | H | H | CH3 | H | H | H | H | F |
| 140 | Ir | 3 | 0 | Ph | P1 | H | H | H | CH3 | H | H | H | F |
| 141 | Ir | 3 | 0 | Ph | P1 | C2H5 | H | H | H | CF3 | H | H | H |
| 142 | Ir | 3 | 0 | Ph | P1 | H | C2H5 | H | H | CF3 | H | H | H |
| 143 | Ir | 3 | 0 | Ph | P1 | H | H | C2H5 | H | CF3 | H | H | H |
| 144 | Ir | 3 | 0 | Ph | P1 | H | H | H | C2H5 | CF3 | H | H | H |
| 145 | Ir | 3 | 0 | Ph | P1 | C2H5 | H | H | H | H | CF3 | H | H |
| 146 | Ir | 3 | 0 | Ph | P1 | H | C2H5 | H | H | H | CF3 | H | H |
| 147 | Ir | 3 | 0 | Ph | P1 | H | H | C2H5 | H | H | CF3 | H | H |
| 148 | Ir | 3 | 0 | Ph | P1 | H | H | H | C2H5 | H | CF3 | H | H |
| 149 | Ir | 3 | 0 | Ph | P1 | C2H5 | H | H | H | H | H | CF3 | H |
| 150 | Ir | 3 | 0 | Ph | P1 | H | C2H5 | H | H | H | H | CF3 | H |
| 151 | Ir | 3 | 0 | Ph | P1 | H | H | C2H5 | H | H | H | CF3 | H |
| 152 | Ir | 3 | 0 | Ph | P1 | H | H | H | C2H5 | H | H | CF3 | H |
| 153 | Ir | 3 | 0 | Ph | P1 | C2H5 | H | H | H | H | H | H | CF3 |
| 154 | Ir | 3 | 0 | Ph | P1 | H | C2H5 | H | H | H | H | H | CF3 |
| 155 | Ir | 3 | 0 | Ph | P1 | H | H | C2H5 | H | H | H | H | CF3 |
| 156 | Ir | 3 | 0 | Ph | P1 | H | H | H | C2H5 | H | H | H | CF3 |
| 157 | Ir | 3 | 0 | Ph | P1 | C2H5 | H | H | H | F | H | H | H |
| 158 | Ir | 3 | 0 | Ph | P1 | H | C2H5 | H | H | F | H | H | H |
| 159 | Ir | 3 | 0 | Ph | P1 | H | H | C2H5 | H | F | H | H | H |
| 160 | Ir | 3 | 0 | Ph | P1 | H | H | H | C2H5 | F | H | H | H |
| 161 | Ir | 3 | 0 | Ph | P1 | C2H5 | H | H | H | H | F | H | H |
| 162 | Ir | 3 | 0 | Ph | P1 | H | C2H5 | H | H | H | F | H | H |
| 163 | Ir | 3 | 0 | Ph | P1 | H | H | C2H5 | H | H | F | H | H |
| 164 | Ir | 3 | 0 | Ph | P1 | H | H | H | C2H5 | H | F | H | H |
| 165 | Ir | 3 | 0 | Ph | P1 | C2H5 | H | H | H | H | H | F | H |
| 166 | Ir | 3 | 0 | Ph | P1 | H | C2H5 | H | H | H | H | F | H |
| 167 | Ir | 3 | 0 | Ph | P1 | H | H | C2H5 | H | H | H | F | H |
| 168 | Ir | 3 | 0 | Ph | P1 | H | H | H | C2H5 | H | H | F | H |
| 169 | Ir | 3 | 0 | Ph | P1 | C2H5 | H | H | H | H | H | H | F |
| 170 | Ir | 3 | 0 | Ph | P1 | H | C2H5 | H | H | H | H | H | F |
| 171 | Ir | 3 | 0 | Ph | P1 | H | H | C2H5 | H | H | H | H | F |
| 172 | Ir | 3 | 0 | Ph | P1 | H | H | H | C2H5 | H | H | H | F |
| 173 | Ir | 3 | 0 | Ph | P1 | C4H9 | H | H | H | F | H | H | H |
| 174 | Ir | 3 | 0 | Ph | P1 | H | C4H9 | H | H | F | H | H | H |
| 175 | Ir | 3 | 0 | Ph | P1 | H | H | C4H9 | H | F | H | H | H |
| 176 | Ir | 3 | 0 | Ph | P1 | H | H | H | C4H9 | F | H | H | H |
| 177 | Ir | 3 | 0 | Ph | P1 | C4H9 | H | H | H | H | F | H | H |
| 178 | Ir | 3 | 0 | Ph | P1 | H | C4H9 | H | H | H | F | H | H |
| 179 | Ir | 3 | 0 | Ph | P1 | H | H | C4H9 | H | H | F | H | H |
| 180 | Ir | 3 | 0 | Ph | P1 | H | H | H | C4H9 | H | F | H | H |

TABLE 1-4

| No | M | m | n | A | B | A-R1 | A-R2 | A-R3 | A-R4 | B-R5 | B-R6 | B-R7 | B-R8 |
|---|---|---|---|---|---|---|---|---|---|---|---|---|---|
| 181 | Ir | 3 | 0 | Ph | P1 | C4H9 | H | H | H | H | H | F | H |
| 182 | Ir | 3 | 0 | Ph | P1 | H | C4H9 | H | H | H | H | F | H |
| 183 | Ir | 3 | 0 | Ph | P1 | H | H | C4H9 | H | H | H | F | H |
| 184 | Ir | 3 | 0 | Ph | P1 | H | H | H | C4H9 | H | H | F | H |
| 185 | Ir | 3 | 0 | Ph | P1 | C4H9 | H | H | H | H | H | H | F |
| 186 | Ir | 3 | 0 | Ph | P1 | H | C4H9 | H | H | H | H | H | F |
| 187 | Ir | 3 | 0 | Ph | P1 | H | H | C4H9 | H | H | H | H | F |
| 188 | Ir | 3 | 0 | Ph | P1 | H | H | H | C4H9 | H | H | H | F |
| 189 | Ir | 3 | 0 | Ph | P1 | C4H9 | H | H | H | CF3 | H | H | H |
| 190 | Ir | 3 | 0 | Ph | P1 | H | C4H9 | H | H | CF3 | H | H | H |
| 191 | Ir | 3 | 0 | Ph | P1 | H | H | C4H9 | H | CF3 | H | H | H |
| 192 | Ir | 3 | 0 | Ph | P1 | H | H | H | C4H9 | CF3 | H | H | H |
| 193 | Ir | 3 | 0 | Ph | P1 | C4H9 | H | H | H | H | CF3 | H | H |
| 194 | Ir | 3 | 0 | Ph | P1 | H | C4H9 | H | H | H | CF3 | H | H |
| 195 | Ir | 3 | 0 | Ph | P1 | H | H | C4H9 | H | H | CF3 | H | H |
| 196 | Ir | 3 | 0 | Ph | P1 | H | H | H | C4H9 | H | CF3 | H | H |
| 197 | Ir | 3 | 0 | Ph | P1 | C4H9 | H | H | H | H | H | CF3 | H |
| 198 | Ir | 3 | 0 | Ph | P1 | H | C4H9 | H | H | H | H | CF3 | H |
| 199 | Ir | 3 | 0 | Ph | P1 | H | H | C4H9 | H | H | H | CF3 | H |
| 200 | Ir | 3 | 0 | Ph | P1 | H | H | H | C4H9 | H | H | CF3 | H |
| 201 | Ir | 3 | 0 | Ph | P1 | C4H9 | H | H | H | H | H | H | CF3 |
| 202 | Ir | 3 | 0 | Ph | P1 | H | C4H9 | H | H | H | H | H | CF3 |
| 203 | Ir | 3 | 0 | Ph | P1 | H | H | C4H9 | H | H | H | H | CF3 |
| 204 | Ir | 3 | 0 | Ph | P1 | H | H | H | C4H9 | H | H | H | CF3 |
| 205 | Ir | 3 | 0 | Ph | P1 | C8H17 | H | H | H | F | H | H | H |
| 206 | Ir | 3 | 0 | Ph | P1 | H | C8H17 | H | H | F | H | H | H |
| 207 | Ir | 3 | 0 | Ph | P1 | H | H | C8H17 | H | F | H | H | H |
| 208 | Ir | 3 | 0 | Ph | P1 | H | H | H | C8H17 | F | H | H | H |
| 209 | Ir | 3 | 0 | Ph | P1 | C8H17 | H | H | H | H | F | H | H |
| 210 | Ir | 3 | 0 | Ph | P1 | H | C8H17 | H | H | H | F | H | H |
| 211 | Ir | 3 | 0 | Ph | P1 | H | H | C8H17 | H | H | F | H | H |
| 212 | Ir | 3 | 0 | Ph | P1 | H | H | H | C8H17 | H | F | H | H |
| 213 | Ir | 3 | 0 | Ph | P1 | C8H17 | H | H | H | H | H | F | H |
| 214 | Ir | 3 | 0 | Ph | P1 | H | C8H17 | H | H | H | H | F | H |
| 215 | Ir | 3 | 0 | Ph | P1 | H | H | C8H17 | H | H | H | F | H |
| 216 | Ir | 3 | 0 | Ph | P1 | H | H | H | C8H17 | H | H | F | H |
| 217 | Ir | 3 | 0 | Ph | P1 | C8H17 | H | H | H | H | H | H | F |
| 218 | Ir | 3 | 0 | Ph | P1 | H | C8H17 | H | H | H | H | H | F |
| 219 | Ir | 3 | 0 | Ph | P1 | H | H | C8H17 | H | H | H | H | F |
| 220 | Ir | 3 | 0 | Ph | P1 | H | H | H | C8H17 | H | H | H | F |
| 221 | Ir | 3 | 0 | Ph | P1 | C8H17 | H | H | H | CF3 | H | H | H |
| 222 | Ir | 3 | 0 | Ph | P1 | H | C8H17 | H | H | CF3 | H | H | H |
| 223 | Ir | 3 | 0 | Ph | P1 | H | H | C8H17 | H | CF3 | H | H | H |
| 224 | Ir | 3 | 0 | Ph | P1 | H | H | H | C8H17 | CF3 | H | H | H |
| 225 | Ir | 3 | 0 | Ph | P1 | C8H17 | H | H | H | H | CF3 | H | H |
| 226 | Ir | 3 | 0 | Ph | P1 | H | C8H17 | H | H | H | CF3 | H | H |
| 227 | Ir | 3 | 0 | Ph | P1 | H | H | C8H17 | H | H | CF3 | H | H |
| 228 | Ir | 3 | 0 | Ph | P1 | H | H | H | C8H17 | H | CF3 | H | H |
| 229 | Ir | 3 | 0 | Ph | P1 | C8H17 | H | H | H | H | H | CF3 | H |
| 230 | Ir | 3 | 0 | Ph | P1 | H | C8H17 | H | H | H | H | CF3 | H |
| 231 | Ir | 3 | 0 | Ph | P1 | H | H | C8H17 | H | H | H | CF3 | H |
| 232 | Ir | 3 | 0 | Ph | P1 | H | H | H | C8H17 | H | H | CF3 | H |
| 233 | Ir | 3 | 0 | Ph | P1 | C8H17 | H | H | H | H | H | H | CF3 |
| 234 | Ir | 3 | 0 | Ph | P1 | H | C8H17 | H | H | H | H | H | CF3 |
| 235 | Ir | 3 | 0 | Ph | P1 | H | H | C8H17 | H | H | H | H | CF3 |
| 236 | Ir | 3 | 0 | Ph | P1 | H | H | H | C8H17 | H | H | H | CF3 |
| 237 | Ir | 3 | 0 | Ph | P1 | F | H | H | H | H | H | H | H |
| 238 | Ir | 3 | 0 | Ph | P1 | H | F | H | H | H | H | H | H |
| 239 | Ir | 3 | 0 | Ph | P1 | H | H | F | H | H | H | H | H |
| 240 | Ir | 3 | 0 | Ph | P1 | H | H | H | F | H | H | H | H |

TABLE 1-5

| No | M | m | n | A | B | A-R1 | A-R2 | A-R3 | A-R4 | B-R5 | B-R6 | B-R7 | B-R8 |
|---|---|---|---|---|---|---|---|---|---|---|---|---|---|
| 241 | Ir | 3 | 0 | Ph | P1 | F | F | H | H | H | H | H | H |
| 242 | Ir | 3 | 0 | Ph | P1 | F | H | F | H | H | H | H | H |
| 243 | Ir | 3 | 0 | Ph | P1 | H | F | H | F | H | H | H | H |
| 244 | Ir | 3 | 0 | Ph | P1 | H | F | F | H | H | H | H | H |
| 245 | Ir | 3 | 0 | Ph | P1 | H | F | H | H | H | H | H | H |

TABLE 1-5-continued

| No | M | m | n | A | B | A-R1 | A-R2 | A-R3 | A-R4 | B-R5 | B-R6 | B-R7 | B-R8 |
|---|---|---|---|---|---|---|---|---|---|---|---|---|---|
| 246 | Ir | 3 | 0 | Ph | P1 | H | H | H | F | H | H | H | H |
| 247 | Ir | 3 | 0 | Ph | P1 | H | H | F | F | H | H | H | H |
| 248 | Ir | 3 | 0 | Ph | P1 | F | H | F | F | H | H | H | H |
| 249 | Ir | 3 | 0 | Ph | P1 | F | F | F | H | H | H | H | H |
| 250 | Ir | 3 | 0 | Ph | P1 | H | F | F | F | H | H | H | H |
| 251 | Ir | 3 | 0 | Ph | P1 | F | F | F | F | H | H | H | H |
| 252 | Ir | 3 | 0 | Ph | P1 | F | F | F | F | H | H | H | H |
| 253 | Ir | 3 | 0 | Ph | P1 | F | H | H | H | CH3 | H | H | H |
| 254 | Ir | 3 | 0 | Ph | P1 | F | H | H | H | H | CH3 | H | H |
| 255 | Ir | 3 | 0 | Ph | P1 | F | H | H | H | H | H | CH3 | H |
| 256 | Ir | 3 | 0 | Ph | P1 | F | H | H | H | H | H | H | CH3 |
| 257 | Ir | 3 | 0 | Ph | P1 | H | F | H | H | CH3 | H | H | H |
| 258 | Ir | 3 | 0 | Ph | P1 | H | F | H | H | H | CH3 | H | H |
| 259 | Ir | 3 | 0 | Ph | P1 | H | F | H | H | H | H | CH3 | H |
| 260 | Ir | 3 | 0 | Ph | P1 | H | F | H | H | H | H | H | CH3 |
| 261 | Ir | 3 | 0 | Ph | P1 | H | H | F | H | CH3 | H | H | H |
| 262 | Ir | 3 | 0 | Ph | P1 | H | H | F | H | H | CH3 | H | H |
| 263 | Ir | 3 | 0 | Ph | P1 | H | H | F | H | H | H | CH3 | H |
| 264 | Ir | 3 | 0 | Ph | P1 | H | H | F | H | H | H | H | CH3 |
| 265 | Ir | 3 | 0 | Ph | P1 | H | H | H | F | CH3 | H | H | H |
| 266 | Ir | 3 | 0 | Ph | P1 | H | H | H | F | H | CH3 | H | H |
| 267 | Ir | 3 | 0 | Ph | P1 | H | H | H | F | H | H | CH3 | H |
| 268 | Ir | 3 | 0 | Ph | P1 | H | H | H | F | H | H | H | CH3 |
| 269 | Ir | 3 | 0 | Ph | P1 | F | F | H | H | CH3 | H | H | H |
| 270 | Ir | 3 | 0 | Ph | P1 | F | F | H | H | H | CH3 | H | H |
| 271 | Ir | 3 | 0 | Ph | P1 | F | F | H | H | H | H | CH3 | H |
| 272 | Ir | 3 | 0 | Ph | P1 | F | F | H | H | H | H | H | CH3 |
| 273 | Ir | 3 | 0 | Ph | P1 | F | H | F | H | CH3 | H | H | H |
| 274 | Ir | 3 | 0 | Ph | P1 | F | H | F | H | H | CH3 | H | H |
| 275 | Ir | 3 | 0 | Ph | P1 | F | H | F | H | H | H | CH3 | H |
| 276 | Ir | 3 | 0 | Ph | P1 | F | H | F | H | H | H | H | CH3 |
| 277 | Ir | 3 | 0 | Ph | P1 | F | H | H | F | CH3 | H | H | H |
| 278 | Ir | 3 | 0 | Ph | P1 | F | H | H | F | H | CH3 | H | H |
| 279 | Ir | 3 | 0 | Ph | P1 | F | H | H | F | H | H | CH3 | H |
| 280 | Ir | 3 | 0 | Ph | P1 | F | H | H | F | H | H | H | CH3 |
| 281 | Ir | 3 | 0 | Ph | P1 | H | F | F | H | CH3 | H | H | H |
| 282 | Ir | 3 | 0 | Ph | P1 | H | F | F | H | H | CH3 | H | H |
| 283 | Ir | 3 | 0 | Ph | P1 | H | F | F | H | H | H | CH3 | H |
| 284 | Ir | 3 | 0 | Ph | P1 | H | F | F | H | H | H | H | CH3 |
| 285 | Ir | 3 | 0 | Ph | P1 | H | F | H | F | CH3 | H | H | H |
| 286 | Ir | 3 | 0 | Ph | P1 | H | F | H | F | H | CH3 | H | H |
| 287 | Ir | 3 | 0 | Ph | P1 | H | F | H | F | H | H | CH3 | H |
| 288 | Ir | 3 | 0 | Ph | P1 | H | F | H | F | H | H | H | CH3 |
| 289 | Ir | 3 | 0 | Ph | P1 | H | H | F | F | CH3 | H | H | H |
| 290 | Ir | 3 | 0 | Ph | P1 | H | H | F | F | H | CH3 | H | H |
| 291 | Ir | 3 | 0 | Ph | P1 | H | H | F | F | H | H | CH3 | H |
| 292 | Ir | 3 | 0 | Ph | P1 | H | H | F | F | H | H | H | CH3 |
| 293 | Ir | 3 | 0 | Ph | P1 | F | F | F | H | CH3 | H | H | H |
| 294 | Ir | 3 | 0 | Ph | P1 | F | F | F | H | H | CH3 | H | H |
| 295 | Ir | 3 | 0 | Ph | P1 | F | F | F | H | H | H | CH3 | H |
| 296 | Ir | 3 | 0 | Ph | P1 | F | F | F | H | H | H | H | CH3 |
| 297 | Ir | 3 | 0 | Ph | P1 | F | F | H | F | CH3 | H | H | H |
| 298 | Ir | 3 | 0 | Ph | P1 | F | F | H | F | H | CH3 | H | H |
| 299 | Ir | 3 | 0 | Ph | P1 | F | F | H | F | H | H | CH3 | H |
| 300 | Ir | 3 | 0 | Ph | P1 | F | F | H | F | H | H | H | CH3 |

TABLE 1-6

| No | M | m | n | A | B | A-R1 | A-R2 | A-R3 | A-R4 | B-R5 | B-R6 | B-R7 | B-R8 |
|---|---|---|---|---|---|---|---|---|---|---|---|---|---|
| 301 | Ir | 3 | 0 | Ph | P1 | F | H | F | F | CH3 | H | H | H |
| 302 | Ir | 3 | 0 | Ph | P1 | F | H | F | F | H | CH3 | H | H |
| 303 | Ir | 3 | 0 | Ph | P1 | F | H | F | F | H | H | CH3 | H |
| 304 | Ir | 3 | 0 | Ph | P1 | F | H | F | F | H | H | H | CH3 |
| 305 | Ir | 3 | 0 | Ph | P1 | F | F | F | F | CH3 | H | H | H |
| 306 | Ir | 3 | 0 | Ph | P1 | F | F | F | F | H | CH3 | H | H |
| 307 | Ir | 3 | 0 | Ph | P1 | F | F | F | F | H | H | CH3 | H |
| 308 | Ir | 3 | 0 | Ph | P1 | F | F | F | F | H | H | H | CH3 |
| 309 | Ir | 3 | 0 | Ph | P1 | CF3 | H | H | H | H | H | H | H |
| 310 | Ir | 3 | 0 | Ph | P1 | H | CF3 | H | H | H | H | H | H |
| 311 | Ir | 3 | 0 | Ph | P1 | H | H | CF3 | H | H | H | H | H |

TABLE 1-6-continued

| No | M | m | n | A | B | A-R1 | A-R2 | A-R3 | A-R4 | B-R5 | B-R6 | B-R7 | B-R8 |
|---|---|---|---|---|---|---|---|---|---|---|---|---|---|
| 312 | Ir | 3 | 0 | Ph | P1 | H | CF3 | H | CF3 | H | H | H | H |
| 313 | Ir | 3 | 0 | Ph | P1 | CF3 | CF3 | H | H | H | H | H | H |
| 314 | Ir | 3 | 0 | Ph | P1 | CF3 | H | CF3 | H | H | H | H | H |
| 315 | Ir | 3 | 0 | Ph | P1 | CF3 | H | H | CF3 | H | H | H | H |
| 316 | Ir | 3 | 0 | Ph | P1 | H | CF3 | CF3 | H | H | H | H | H |
| 317 | Ir | 3 | 0 | Ph | P1 | H | H | C3F7C2H4 | H | H | H | H | H |
| 318 | Ir | 3 | 0 | Ph | P1 | H | H | C7F15 | H | H | H | H | H |
| 319 | Ir | 3 | 0 | Ph | P1 | H | H | CF3 | CF3 | H | H | H | H |
| 320 | Ir | 3 | 0 | Ph | P1 | CF3 | H | CF3 | CF3 | H | H | H | H |
| 321 | Ir | 3 | 0 | Ph | P1 | CF3 | CF3 | CF3 | H | H | H | H | H |
| 322 | Ir | 3 | 0 | Ph | P1 | H | CF3 | CF3 | CF3 | H | H | H | H |
| 323 | Ir | 3 | 0 | Ph | P1 | CF3 | CF3 | CF3 | H | H | H | H | H |
| 324 | Ir | 3 | 0 | Ph | P1 | CF3 | CF3 | CF3 | CF3 | H | H | H | H |
| 325 | Ir | 3 | 0 | Ph | P1 | CF3 | H | H | H | CH3 | H | H | H |
| 326 | Ir | 3 | 0 | Ph | P1 | CF3 | H | H | H | H | CH3 | H | H |
| 327 | Ir | 3 | 0 | Ph | P1 | CF3 | H | H | H | H | H | CH3 | H |
| 328 | Ir | 3 | 0 | Ph | P1 | CF3 | H | H | H | H | H | H | CH3 |
| 329 | Ir | 3 | 0 | Ph | P1 | H | CF3 | H | H | CH3 | H | H | H |
| 330 | Ir | 3 | 0 | Ph | P1 | H | CF3 | H | H | H | CH3 | H | H |
| 331 | Ir | 3 | 0 | Ph | P1 | H | CF3 | H | H | H | H | CH3 | H |
| 332 | Ir | 3 | 0 | Ph | P1 | H | CF3 | H | H | H | H | H | CH3 |
| 333 | Ir | 3 | 0 | Ph | P1 | H | H | CF3 | H | CH3 | H | H | H |
| 334 | Ir | 3 | 0 | Ph | P1 | H | H | CF3 | H | H | CH3 | H | H |
| 335 | Ir | 3 | 0 | Ph | P1 | H | H | CF3 | H | H | H | CH3 | H |
| 336 | Ir | 3 | 0 | Ph | P1 | H | H | CF3 | H | H | H | H | CH3 |
| 337 | Ir | 3 | 0 | Ph | P1 | H | H | H | CF3 | CH3 | H | H | H |
| 338 | Ir | 3 | 0 | Ph | P1 | H | H | H | CF3 | H | CH3 | H | H |
| 339 | Ir | 3 | 0 | Ph | P1 | H | H | H | CF3 | H | H | CH3 | H |
| 340 | Ir | 3 | 0 | Ph | P1 | H | H | H | CH3 | H | H | H | CH3 |
| 341 | Ir | 3 | 0 | Ph | P1 | CF3 | CF3 | H | H | CH3 | H | H | H |
| 342 | Ir | 3 | 0 | Ph | P1 | CF3 | CF3 | H | H | H | CH3 | H | H |
| 343 | Ir | 3 | 0 | Ph | P1 | CF3 | CF3 | H | H | H | H | CH3 | H |
| 344 | Ir | 3 | 0 | Ph | P1 | CF3 | CF3 | H | H | H | H | H | CH3 |
| 345 | Ir | 3 | 0 | Ph | P1 | CF3 | H | CF3 | H | CH3 | H | H | H |
| 346 | Ir | 3 | 0 | Ph | P1 | CF3 | H | CF3 | H | H | CH3 | H | H |
| 347 | Ir | 3 | 0 | Ph | P1 | CF3 | H | CF3 | H | H | H | CH3 | H |
| 348 | Ir | 3 | 0 | Ph | P1 | CF3 | H | CF3 | H | H | H | H | CH3 |
| 349 | Ir | 3 | 0 | Ph | P1 | CF3 | H | H | CF3 | CH3 | H | H | H |
| 350 | Ir | 3 | 0 | Ph | P1 | CF3 | H | H | CF3 | H | CH3 | H | H |
| 351 | Ir | 3 | 0 | Ph | P1 | CF3 | H | H | CF3 | H | H | CH3 | H |
| 352 | Ir | 3 | 0 | Ph | P1 | CF3 | H | H | CF3 | H | H | H | CH3 |
| 353 | Ir | 3 | 0 | Ph | P1 | H | CF3 | CF3 | H | CH3 | H | H | H |
| 354 | Ir | 3 | 0 | Ph | P1 | H | CF3 | CF3 | H | H | CH3 | H | H |
| 355 | Ir | 3 | 0 | Ph | P1 | H | CF3 | CF3 | H | H | H | CH3 | H |
| 356 | Ir | 3 | 0 | Ph | P1 | H | CF3 | CF3 | H | H | H | H | CH3 |
| 357 | Ir | 3 | 0 | Ph | P1 | H | CF3 | H | CF3 | CH3 | H | H | H |
| 358 | Ir | 3 | 0 | Ph | P1 | H | CF3 | H | CF3 | H | CH3 | H | H |
| 359 | Ir | 3 | 0 | Ph | P1 | H | CF3 | H | CF3 | H | H | CH3 | H |
| 360 | Ir | 3 | 0 | Ph | P1 | H | CF3 | H | CF3 | H | H | H | CH3 |

TABLE 1-7

| No | M | m | n | A | B | A-R1 | A-R2 | A-R3 | A-R4 | B-R5 | B-R6 | B-R7 | B-R8 |
|---|---|---|---|---|---|---|---|---|---|---|---|---|---|
| 361 | Ir | 3 | 0 | Ph | P1 | H | H | CF3 | CF3 | CH3 | H | H | H |
| 362 | Ir | 3 | 0 | Ph | P1 | H | H | CF3 | CF3 | H | CH3 | H | H |
| 363 | Ir | 3 | 0 | Ph | P1 | H | H | CF3 | CF3 | H | H | CH3 | H |
| 364 | Ir | 3 | 0 | Ph | P1 | H | H | CF3 | CF3 | H | H | H | CH3 |
| 365 | Ir | 3 | 0 | Ph | P1 | CF3 | CF3 | CF3 | H | CH3 | H | H | H |
| 366 | Ir | 3 | 0 | Ph | P1 | CF3 | CF3 | CF3 | H | H | CH3 | H | H |
| 367 | Ir | 3 | 0 | Ph | P1 | CF3 | CF3 | CF3 | H | H | H | CH3 | H |
| 368 | Ir | 3 | 0 | Ph | P1 | CF3 | CF3 | CF3 | H | H | H | H | CH3 |
| 369 | Ir | 3 | 0 | Ph | P1 | CF3 | CF3 | H | CF3 | CH3 | H | H | H |
| 370 | Ir | 3 | 0 | Ph | P1 | CF3 | CF3 | H | CF3 | H | CH3 | H | H |
| 371 | Ir | 3 | 0 | Ph | P1 | CF3 | CF3 | H | CF3 | H | H | CH3 | H |
| 372 | Ir | 3 | 0 | Ph | P1 | CF3 | CF3 | H | CF3 | H | H | H | CH3 |
| 373 | Ir | 3 | 0 | Ph | P1 | CF3 | H | CF3 | CF3 | CH3 | H | H | H |
| 374 | Ir | 3 | 0 | Ph | P1 | CF3 | H | CF3 | CF3 | H | CH3 | H | H |
| 375 | Ir | 3 | 0 | Ph | P1 | CF3 | H | CF3 | CF3 | H | H | CH3 | H |
| 376 | Ir | 3 | 0 | Ph | P1 | CF3 | H | CF3 | CF3 | H | H | H | CH3 |
| 377 | Ir | 3 | 0 | Ph | P1 | CF3 | CF3 | CF3 | CF3 | CH3 | H | H | H |

TABLE 1-7-continued

| No | M | m | n | A | B | A-R1 | A-R2 | A-R3 | A-R4 | B-R5 | B-R6 | B-R7 | B-R8 |
|---|---|---|---|---|---|---|---|---|---|---|---|---|---|
| 378 | Ir | 3 | 0 | Ph | P1 | CF3 | CF3 | CF3 | CF3 | H | CH3 | H | H |
| 379 | Ir | 3 | 0 | Ph | P1 | CF3 | CF3 | CF3 | CF3 | H | H | CH3 | H |
| 380 | Ir | 3 | 0 | Ph | P1 | CF3 | CF3 | CF3 | CF3 | H | H | H | CH3 |
| 381 | Ir | 3 | 0 | Ph | P1 | F | CF3 | H | H | H | H | H | H |
| 382 | Ir | 3 | 0 | Ph | P1 | F | CF3 | H | CF3 | H | H | H | H |
| 383 | Ir | 3 | 0 | Ph | P1 | F | H | H | CF3 | H | H | H | H |
| 384 | Ir | 3 | 0 | Ph | P1 | H | CF3 | F | H | H | H | H | H |
| 385 | Ir | 3 | 0 | Ph | P1 | H | CF3 | F | CF3 | H | H | H | H |
| 386 | Ir | 3 | 0 | Ph | P1 | H | H | F | CF3 | H | H | H | H |
| 387 | Ir | 3 | 0 | Ph | P1 | F | CF3 | F | H | H | H | H | H |
| 388 | Ir | 3 | 0 | Ph | P1 | F | H | F | CF3 | H | H | H | H |
| 389 | Ir | 3 | 0 | Ph | P1 | H | CH3 | F | H | H | H | H | H |
| 390 | Ir | 3 | 0 | Ph | P1 | H | CH3 | CF3 | H | H | H | H | H |
| 391 | Ir | 3 | 0 | Ph | P1 | F | CF3 | H | CF3 | H | H | H | H |
| 392 | Ir | 3 | 0 | Ph | P1 | CF3 | H | F | H | H | H | H | H |
| 393 | Ir | 3 | 0 | Ph | P1 | H | CF3 | F | H | H | CH3 | H | H |
| 394 | Ir | 3 | 0 | Ph | P1 | H | CF3 | F | CF3 | H | CH3 | H | H |
| 395 | Ir | 3 | 0 | Ph | P1 | H | H | F | CF3 | H | CH3 | H | H |
| 396 | Ir | 3 | 0 | Ph | P1 | F | CF3 | F | H | H | CH3 | H | H |
| 397 | Ir | 3 | 0 | Ph | P1 | F | H | F | CF3 | H | CH3 | H | H |
| 398 | Ir | 3 | 0 | Ph | P1 | F | CF3 | F | CF3 | H | CH3 | H | H |
| 399 | Ir | 3 | 0 | Ph | P1 | F | CF3 | H | H | H | H | CH3 | H |
| 400 | Ir | 3 | 0 | Ph | P1 | F | CF3 | H | CF3 | H | H | CH3 | H |
| 401 | Ir | 3 | 0 | Ph | P1 | F | H | H | CF3 | H | H | CH3 | H |
| 402 | Ir | 3 | 0 | Ph | P1 | H | CF3 | F | H | H | H | CH3 | H |
| 403 | Ir | 3 | 0 | Ph | P1 | H | CF3 | F | CF3 | H | H | CH3 | H |
| 404 | Ir | 3 | 0 | Ph | P1 | H | H | F | CF3 | H | H | CH3 | H |
| 405 | Ir | 3 | 0 | Ph | P1 | F | CF3 | F | H | H | H | CH3 | H |
| 406 | Ir | 3 | 0 | Ph | P1 | F | H | F | CF3 | H | H | CH3 | H |
| 407 | Ir | 3 | 0 | Ph | P1 | F | CF3 | F | CF3 | H | H | CH3 | H |
| 408 | Ir | 3 | 0 | Ph | P1 | F | H | H | H | H | CF3 | H | H |
| 409 | Ir | 3 | 0 | Ph | P1 | H | F | H | H | H | CF3 | H | H |
| 410 | Ir | 3 | 0 | Ph | P1 | H | H | F | H | H | CF3 | H | H |
| 411 | Ir | 3 | 0 | Ph | P1 | H | H | H | F | H | CF3 | H | H |
| 412 | Ir | 3 | 0 | Ph | P1 | F | H | H | H | H | H | CF3 | H |
| 413 | Ir | 3 | 0 | Ph | P1 | H | F | H | H | H | H | CF3 | H |
| 414 | Ir | 3 | 0 | Ph | P1 | H | H | F | H | H | H | CF3 | H |
| 415 | Ir | 3 | 0 | Ph | P1 | H | H | H | F | H | H | CF3 | H |
| 416 | Ir | 3 | 0 | Ph | P1 | H | F | H | F | H | CF3 | H | H |
| 417 | Ir | 3 | 0 | Ph | P1 | H | F | H | F | H | CF3 | H | H |
| 418 | Ir | 3 | 0 | Ph | P1 | H | F | H | F | H | CF3 | H | H |
| 419 | Ir | 3 | 0 | Ph | P1 | H | F | H | F | H | CF3 | H | H |
| 420 | Ir | 3 | 0 | Ph | P1 | H | F | H | F | H | H | CF3 | H |

TABLE 1-8

| No | M | m | n | A | B | E | J | G | A-R1 | A-R2 | A-R3 | A-R4 | B-R5 | B-R6 | B-R7 | B-R8 |
|---|---|---|---|---|---|---|---|---|---|---|---|---|---|---|---|---|
| 421 | Ir | 3 | 0 | Ph | P1 | — | — | — | H | F | H | F | H | H | CF3 | H |
| 422 | Ir | 3 | 0 | Ph | P1 | — | — | — | H | F | H | F | H | H | CF3 | H |
| 423 | Ir | 3 | 0 | Ph | P1 | — | — | — | H | F | H | F | H | H | CF3 | H |
| 424 | Ir | 3 | 0 | Ph | P1 | — | — | — | CF3 | H | H | H | H | CF3 | H | H |
| 425 | Ir | 3 | 0 | Ph | P1 | — | — | — | H | CF3 | H | H | H | CF3 | H | H |
| 426 | Ir | 3 | 0 | Ph | P1 | — | — | — | H | H | CF3 | H | H | CF3 | H | H |
| 427 | Ir | 3 | 0 | Ph | P1 | — | — | — | H | H | H | CF3 | H | CF3 | H | H |
| 428 | Ir | 3 | 0 | Ph | P1 | — | — | — | CF3 | H | H | H | H | H | CF3 | H |
| 429 | Ir | 3 | 0 | Ph | P1 | — | — | — | H | CF3 | H | H | H | H | CF3 | H |
| 430 | Ir | 3 | 0 | Ph | P1 | — | — | — | H | H | CF3 | H | H | H | CF3 | H |
| 431 | Ir | 3 | 0 | Ph | P1 | — | — | — | H | H | H | CF3 | H | H | CF3 | H |
| 432 | Ir | 3 | 0 | Ph | P1 | — | — | — | CF3 | H | CF3 | H | H | CF3 | H | H |
| 433 | Ir | 3 | 0 | Ph | P1 | — | — | — | H | F | CF3 | H | H | CF3 | H | H |
| 434 | Ir | 3 | 0 | Ph | P1 | — | — | — | CF3 | H | CF3 | H | H | CF3 | H | H |
| 435 | Ir | 3 | 0 | Ph | P1 | — | — | — | H | H | H | CF3 | H | CF3 | H | H |
| 436 | Ir | 3 | 0 | Ph | P1 | — | — | — | CF3 | H | CF3 | H | H | H | CF3 | H |
| 437 | Ir | 3 | 0 | Ph | P1 | — | — | — | H | F | CF3 | H | H | H | CF3 | H |
| 438 | Ir | 3 | 0 | Ph | P1 | — | — | — | CF3 | H | CF3 | H | H | H | CF3 | H |
| 439 | Ir | 3 | 0 | Ph | P1 | — | — | — | H | H | H | CF3 | H | H | CF3 | H |
| 440 | Ir | 2 | 1 | Ph | P1 | CH3 | H | CH3 | CH3 | H | H | H | H | H | H | H |
| 441 | Ir | 2 | 1 | Ph | P1 | CH3 | H | CH3 | H | CH3 | H | H | H | H | H | H |
| 442 | Ir | 2 | 1 | Ph | P1 | CH3 | H | CH3 | H | H | CH3 | H | H | H | H | H |
| 443 | Ir | 2 | 1 | Ph | P1 | CH3 | H | CH3 | H | H | H | CH3 | H | H | H | H |

TABLE 1-8-continued

| No | M | m | n | A | B | E | J | G | A-R1 | A-R2 | A-R3 | A-R4 | B-R5 | B-R6 | B-R7 | B-R8 |
|---|---|---|---|---|---|---|---|---|---|---|---|---|---|---|---|---|
| 444 | Ir | 2 | 1 | Ph | P1 | CH3 | H | CH3 | C2H5 | H | H | H | H | H | H | H |
| 445 | Ir | 2 | 1 | Ph | P1 | CH3 | H | CH3 | H | C2H5 | H | H | H | H | H | H |
| 446 | Ir | 2 | 1 | Ph | P1 | CH3 | H | CH3 | H | H | C2H5 | H | H | H | H | H |
| 447 | Ir | 2 | 1 | Ph | P1 | CH3 | H | CH3 | H | H | H | C2H5 | H | H | H | H |
| 448 | Ir | 2 | 1 | Ph | P1 | CH3 | H | CH3 | C3H7 | H | H | H | H | H | H | H |
| 449 | Ir | 2 | 1 | Ph | P1 | CH3 | H | CH3 | H | C3H7 | H | H | H | H | H | H |
| 450 | Ir | 2 | 1 | Ph | P1 | CH3 | H | CH3 | H | H | C3H7 | H | H | H | H | H |
| 451 | Ir | 2 | 1 | Ph | P1 | CH3 | H | CH3 | H | H | H | C3H7 | H | H | H | H |
| 452 | Ir | 2 | 1 | Ph | P1 | CH3 | H | CH3 | C4H9 | H | H | H | H | H | H | H |
| 453 | Ir | 2 | 1 | Ph | P1 | CH3 | H | CH3 | H | C4H9 | H | H | H | H | H | H |
| 454 | Ir | 2 | 1 | Ph | P1 | CH3 | H | CH3 | H | H | C4H9 | H | H | H | H | H |
| 455 | Ir | 2 | 1 | Ph | P1 | CH3 | H | CH3 | H | H | H | C4H9 | H | H | H | H |
| 456 | Ir | 2 | 1 | Ph | P1 | CH3 | H | CH3 | C6H13 | H | H | H | H | H | H | H |
| 457 | Ir | 2 | 1 | Ph | P1 | CH3 | H | CH3 | — | C6H13 | H | H | H | H | H | H |
| 458 | Ir | 2 | 1 | Ph | P1 | CH3 | H | CH3 | H | H | C6H13 | H | H | H | H | H |
| 459 | Ir | 2 | 1 | Ph | P1 | CH3 | H | CH3 | H | H | H | C6H13 | H | H | H | H |
| 460 | Ir | 2 | 1 | Ph | P1 | CH3 | H | CH3 | C8H17 | H | H | H | H | H | H | H |
| 461 | Ir | 2 | 1 | Ph | P1 | CH3 | H | CH3 | H | C8H17 | H | H | H | H | H | H |
| 462 | Ir | 2 | 1 | Ph | P1 | CH3 | H | CH3 | H | H | C8H17 | H | H | H | H | H |
| 463 | Ir | 2 | 1 | Ph | P1 | CH3 | H | CH3 | H | H | H | C8H17 | H | H | H | H |
| 464 | Ir | 2 | 1 | Ph | P1 | CH3 | H | CH3 | C12H25 | H | H | H | H | H | H | H |
| 465 | Ir | 2 | 1 | Ph | P1 | CH3 | H | CH3 | H | C12H25 | H | H | H | H | H | H |
| 466 | Ir | 2 | 1 | Ph | P1 | CH3 | H | CH3 | H | H | C12H25 | H | H | H | H | H |
| 467 | Ir | 2 | 1 | Ph | P1 | CH3 | H | CH3 | H | H | H | C12H25 | H | H | H | H |
| 468 | Ir | 2 | 1 | Ph | P1 | CH3 | H | CH3 | C15H31 | H | H | H | H | H | H | H |
| 469 | Ir | 2 | 1 | Ph | P1 | CH3 | H | CH3 | H | C15H31 | H | H | H | H | H | H |
| 470 | Ir | 2 | 1 | Ph | P1 | CH3 | H | CH3 | H | H | C15H31 | H | H | H | H | H |
| 471 | Ir | 2 | 1 | Ph | P1 | CH3 | H | CH3 | H | H | H | C15H31 | H | H | H | H |
| 472 | Ir | 2 | 1 | Ph | P1 | CH3 | CH3 | CH3 | H | H | H | H | H | H | H | H |
| 473 | Ir | 2 | 1 | Ph | P1 | CH3 | F | CH3 | H | H | H | H | H | H | H | H |
| 474 | Ir | 2 | 1 | Ph | P1 | CF3 | CH3 | CF3 | H | H | H | H | H | H | H | H |
| 475 | Ir | 2 | 1 | Ph | P1 | CF3 | F | CF3 | H | H | H | H | H | H | H | H |
| 476 | Ir | 2 | 1 | Ph | P1 | CH3 | CF3 | CH3 | H | H | H | H | H | H | H | H |
| 477 | Ir | 2 | 1 | Ph | P1 | C4H9 | F | C4H9 | H | H | H | H | H | H | H | H |
| 478 | Ir | 2 | 1 | Ph | P1 | CH3 | C2H5 | CH3 | H | H | H | H | H | H | H | H |
| 479 | Ir | 2 | 1 | Ph | P1 | CH3 | C4H9 | CH3 | H | H | H | H | H | H | H | H |
| 480 | Ir | 2 | 1 | Ph | P1 | CH3 | CH3 | CH3 | H | CH3 | H | H | H | H | H | H |

TABLE 1-9

| No | M | m | n | A | B | E | J | G | A-R1 | A-R2 | A-R3 | A-R4 | B-R5 | B-R6 | B-R7 | B-R8 |
|---|---|---|---|---|---|---|---|---|---|---|---|---|---|---|---|---|
| 481 | Ir | 2 | 1 | Ph | P1 | CH3 | F | CH3 | H | CH3 | H | H | H | H | H | H |
| 482 | Ir | 2 | 1 | Ph | P1 | CF3 | CH3 | CF3 | H | CH3 | H | H | H | H | H | H |
| 483 | Ir | 2 | 1 | Ph | P1 | CF3 | F | CF3 | H | CH3 | H | H | H | H | H | H |
| 484 | Ir | 2 | 1 | Ph | P1 | CH3 | CF3 | CH3 | H | CH3 | H | H | H | H | H | H |
| 485 | Ir | 2 | 1 | Ph | P1 | C4H9 | F | C4H9 | H | CH3 | H | H | H | H | H | H |
| 486 | Ir | 2 | 1 | Ph | P1 | CH3 | C2H5 | CH3 | H | CH3 | H | H | H | H | H | H |
| 487 | Ir | 2 | 1 | Ph | P1 | CH3 | H | CH3 | H | F | H | H | H | H | H | H |
| 488 | Ir | 2 | 1 | Ph | P1 | CH3 | CH3 | CH3 | H | F | H | H | H | H | H | H |
| 489 | Ir | 2 | 1 | Ph | P1 | CH3 | H | CH3 | H | H | F | H | H | H | H | H |
| 490 | Ir | 2 | 1 | Ph | P1 | CF3 | CH3 | CF3 | H | F | H | H | H | H | H | H |
| 491 | Ir | 2 | 1 | Ph | P1 | CF3 | F | CF3 | H | F | H | H | H | H | H | H |
| 492 | Ir | 2 | 1 | Ph | P1 | CH3 | CF3 | CH3 | H | F | H | H | H | H | H | H |
| 493 | Ir | 2 | 1 | Ph | P1 | C4H9 | F | C4H9 | H | F | H | H | H | H | H | H |
| 494 | Ir | 2 | 1 | Ph | P1 | CH3 | C2H5 | CH3 | H | F | H | H | H | H | H | H |
| 495 | Ir | 2 | 1 | Ph | P1 | CH3 | H | CH3 | H | CF3 | H | H | H | H | H | H |
| 496 | Ir | 2 | 1 | Ph | P1 | CH3 | CH3 | CH3 | H | CF3 | H | H | H | H | H | H |
| 497 | Ir | 2 | 1 | Ph | P1 | CH3 | F | CH3 | H | CF3 | H | H | H | H | H | H |
| 498 | Ir | 2 | 1 | Ph | P1 | CF3 | CH3 | CF3 | H | CF3 | H | H | H | H | H | H |
| 499 | Ir | 2 | 1 | Ph | P1 | CF3 | F | CF3 | H | CF3 | H | H | H | H | H | H |
| 500 | Ir | 2 | 1 | Ph | P1 | CH3 | CF3 | CH3 | H | CF3 | H | H | H | H | H | H |
| 501 | Ir | 2 | 1 | Ph | P1 | C4H9 | F | C4H9 | H | CF3 | H | H | H | H | H | H |
| 502 | Ir | 2 | 1 | Ph | P1 | CH3 | C2H5 | CH3 | H | CF3 | H | H | H | H | H | H |
| 503 | Ir | 2 | 1 | Ph | P1 | CH3 | H | CH3 | H | H | H | H | H | CH3 | H | H |
| 504 | Ir | 2 | 1 | Ph | P1 | CH3 | CH3 | CH3 | H | H | H | H | H | CH3 | H | H |
| 505 | Ir | 2 | 1 | Ph | P1 | CH3 | F | CH3 | H | H | H | H | H | CH3 | H | H |
| 506 | Ir | 2 | 1 | Ph | P1 | CF3 | CH3 | CF3 | H | H | H | H | H | CH3 | H | H |
| 507 | Ir | 2 | 1 | Ph | P1 | CF3 | F | CF3 | H | H | H | H | H | CH3 | H | H |
| 508 | Ir | 2 | 1 | Ph | P1 | CH3 | CF3 | CH3 | H | H | H | H | H | CH3 | H | H |
| 509 | Ir | 2 | 1 | Ph | P1 | C4H9 | F | C4H9 | H | H | H | H | H | CH3 | H | H |

TABLE 1-9-continued

| No | M | m | n | A | B | E | J | G | A-R1 | A-R2 | A-R3 | A-R4 | B-R5 | B-R6 | B-R7 | B-R8 |
|---|---|---|---|---|---|---|---|---|---|---|---|---|---|---|---|---|
| 510 | Ir | 2 | 1 | Ph | P1 | CH3 | C2H5 | CH3 | H | H | H | H | H | CH3 | H | H |
| 511 | Ir | 2 | 1 | Ph | P1 | CH3 | H | CH3 | H | H | H | H | H | H | CH3 | H |
| 512 | Ir | 2 | 1 | Ph | P1 | CH3 | CH3 | CH3 | H | H | H | H | H | CH3 | H | |
| 513 | Ir | 2 | 1 | Ph | P1 | CH3 | F | CH3 | H | H | H | H | H | H | CH3 | H |
| 514 | Ir | 2 | 1 | Ph | P1 | CF3 | CH3 | CF3 | H | H | H | H | H | H | CH3 | H |
| 515 | Ir | 2 | 1 | Ph | P1 | CF3 | F | CF3 | H | H | H | H | H | H | CH3 | H |
| 516 | Ir | 2 | 1 | Ph | P1 | CH3 | CF3 | CH3 | H | H | H | H | H | H | CH3 | H |
| 517 | Ir | 2 | 1 | Ph | P1 | C4H9 | F | C4H9 | H | H | H | H | H | H | CH3 | H |
| 518 | Ir | 2 | 1 | Ph | P1 | CH3 | C2H5 | CH3 | H | H | H | H | H | H | CH3 | H |
| 519 | Ir | 2 | 1 | Ph | P1 | CH3 | H | CH3 | H | CF3 | F | H | H | CH3 | H | H |
| 520 | Ir | 2 | 1 | Ph | P1 | CH3 | CH3 | CH3 | H | CF3 | F | H | H | CH3 | H | H |
| 521 | Ir | 2 | 1 | Ph | P1 | CH3 | F | CH3 | H | CF3 | F | H | H | CH3 | H | H |
| 522 | Ir | 2 | 1 | Ph | P1 | CF3 | CH3 | CF3 | H | CF3 | F | H | H | CH3 | H | H |
| 523 | Ir | 2 | 1 | Ph | P1 | CF3 | F | CF3 | H | CF3 | F | H | H | CH3 | H | H |
| 524 | Ir | 2 | 1 | Ph | P1 | CH3 | CF3 | CH3 | H | CF3 | F | H | H | CH3 | H | H |
| 525 | Ir | 2 | 1 | Ph | P1 | C4H9 | F | C4H9 | H | CF3 | F | H | H | CH3 | H | H |
| 526 | Ir | 2 | 1 | Ph | P1 | CH3 | C2H5 | CH3 | H | CF3 | F | H | H | CH3 | H | H |
| 527 | Ir | 2 | 1 | Ph | P1 | CH3 | H | CH3 | F | H | F | H | H | H | CH3 | H |
| 528 | Ir | 2 | 1 | Ph | P1 | CH3 | CH3 | CH3 | F | H | F | H | H | H | CH3 | H |
| 529 | Ir | 2 | 1 | Ph | P1 | CH3 | F | CH3 | F | H | F | H | H | H | CH3 | H |
| 530 | Ir | 2 | 1 | Ph | P1 | CF3 | CH3 | CF3 | F | H | F | H | H | H | CH3 | H |
| 531 | Ir | 2 | 1 | Ph | P1 | CF3 | F | CF3 | F | H | F | H | H | H | CH3 | H |
| 532 | Ir | 2 | 1 | Ph | P1 | CH3 | CF3 | CH3 | F | H | F | H | H | H | CH3 | H |
| 533 | Ir | 2 | 1 | Ph | P1 | C4H9 | F | C4H9 | F | H | F | H | H | H | CH3 | H |
| 534 | Ir | 2 | 1 | Ph | P1 | CH3 | C2H5 | CH3 | F | H | F | H | H | H | CH3 | H |
| 535 | Ir | 2 | 1 | Ph | P1 | CH3 | H | CH3 | H | F | H | F | H | H | H | H |
| 536 | Ir | 2 | 1 | Ph | P1 | CH3 | CH3 | CH3 | H | F | H | F | H | H | H | H |
| 537 | Ir | 2 | 1 | Ph | P1 | CH3 | F | CH3 | H | F | H | F | H | H | H | H |
| 538 | Ir | 2 | 1 | Ph | P1 | CF3 | CH3 | CF3 | H | F | H | F | H | H | CH3 | H |
| 539 | Ir | 2 | 1 | Ph | P1 | CF3 | F | CF3 | H | H | F | H | H | H | CF3 | H |
| 540 | Ir | 2 | 1 | Ph | P1 | CH3 | CF3 | CH3 | H | H | F | H | H | H | CF3 | H |

TABLE 1-10

| No | M | m | n | A | B | B' or B" | E | J | G | A-R1 | A-R2 | A-R3 | A-R4 | B-R5 | B-R6 | B-R7 | B-R8 |
|---|---|---|---|---|---|---|---|---|---|---|---|---|---|---|---|---|---|
| 541 | Ir | 2 | 1 | Ph | P1 | — | C4H9 | F | C4H9 | H | H | F | H | H | H | CF3 | H |
| 542 | Ir | 2 | 1 | Ph | P1 | — | CH3 | C2H5 | CH3 | H | H | F | H | H | H | CF3 | H |
| 543 | Ir | 2 | 1 | Ph | P1 | — | CH3 | H | CH3 | H | H | F | H | H | CF3 | H | H |
| 544 | Ir | 2 | 1 | Ph | P1 | — | CH3 | CH3 | CH3 | H | H | F | H | H | CF3 | H | H |
| 545 | Ir | 2 | 1 | Ph | P1 | — | CH3 | F | CH3 | H | H | F | H | H | CF3 | H | H |
| 546 | Ir | 2 | 1 | Ph | P1 | — | CF3 | CH3 | CF3 | H | H | F | H | H | CF3 | H | H |
| 547 | Ir | 2 | 1 | Ph | P1 | — | CF3 | F | CF3 | H | H | F | H | H | CF3 | H | H |
| 548 | Ir | 2 | 1 | Ph | P1 | — | CH3 | CF3 | CH3 | H | H | F | H | H | CF3 | H | H |
| 549 | Ir | 2 | 1 | Ph | P1 | — | C4H9 | F | C4H9 | H | H | F | H | H | CF3 | H | H |
| 550 | Ir | 2 | 1 | Ph | P1 | — | CH3 | C2H5 | CH3 | H | H | F | H | H | CF3 | H | H |
| 551 | Ir | 2 | 1 | Ph | P1 | — | CH3 | H | CH3 | H | CF3 | F | H | H | H | H | H |
| 552 | Ir | 2 | 1 | Ph | P1 | — | CH3 | CH3 | CH3 | H | CF3 | F | H | H | H | H | H |
| 553 | Ir | 2 | 1 | Ph | P1 | — | CH3 | F | CH3 | H | CF3 | F | H | H | H | H | H |
| 554 | Ir | 2 | 1 | Ph | P1 | — | CF3 | CH3 | CF3 | H | CF3 | F | H | H | H | H | H |
| 555 | Ir | 2 | 1 | Ph | P1 | — | CF3 | F | CF3 | H | CF3 | F | H | H | H | H | H |
| 556 | Ir | 2 | 1 | Ph | P1 | — | CH3 | CF3 | CH3 | H | CF3 | F | H | H | H | H | H |
| 557 | Ir | 2 | 1 | Ph | P1 | — | C4H9 | F | C4H9 | H | CF3 | F | H | H | H | H | H |
| 558 | Ir | 2 | 1 | Ph | P1 | — | CH3 | C2H5 | CH3 | H | CF3 | F | H | H | H | H | H |
| 559 | Ir | 2 | 1 | Ph | P1 | — | CH3 | H | CH3 | H | CF3 | F | H | H | H | CH3 | H |
| 560 | Ir | 2 | 1 | Ph | P1 | — | CH3 | CH3 | CH3 | H | CF3 | F | H | H | H | CH3 | H |
| 561 | Ir | 2 | 1 | Ph | P1 | — | CH3 | F | CH3 | H | CF3 | F | H | H | H | CH3 | H |
| 562 | Ir | 2 | 1 | Ph | P1 | — | CF3 | CH3 | CF3 | H | CF3 | F | H | H | H | CH3 | H |
| 563 | Ir | 2 | 1 | Ph | P1 | — | CF3 | F | CF3 | H | CF3 | F | H | H | H | CH3 | H |
| 564 | Ir | 2 | 1 | Ph | P1 | — | CH3 | CF3 | CH3 | H | CF3 | F | H | H | H | CH3 | H |
| 565 | Ir | 2 | 1 | Ph | P1 | — | C4H9 | F | C4H9 | H | CF3 | F | H | H | H | CH3 | H |
| 566 | Ir | 2 | 1 | Ph | P1 | — | CH3 | C2H5 | CH3 | H | CF3 | F | H | H | H | CH3 | H |
| 567 | Ir | 2 | 1 | Ph | P1 | — | CH3 | H | CH3 | H | CF3 | H | CF3 | H | H | H | H |
| 568 | Ir | 2 | 1 | Ph | P1 | — | CH3 | CH3 | CH3 | H | CF3 | H | CF3 | H | H | H | H |
| 569 | Ir | 2 | 1 | Ph | P1 | — | CH3 | F | CH3 | H | CF3 | H | CF3 | H | H | H | H |
| 570 | Ir | 2 | 1 | Ph | P1 | — | CF3 | CH3 | CF3 | H | CF3 | H | CF3 | H | H | H | H |
| 571 | Ir | 2 | 1 | Ph | P1 | — | CF3 | F | CF3 | H | CF3 | H | CF3 | H | H | H | H |
| 572 | Ir | 2 | 1 | Ph | P1 | — | CH3 | CF3 | CH3 | H | CF3 | H | CF3 | H | H | H | H |
| 573 | Ir | 2 | 1 | Ph | P1 | — | C4H9 | F | C4H9 | H | CF3 | H | CF3 | H | H | H | H |
| 574 | Ir | 2 | 1 | Ph | P1 | — | CH3 | C2H5 | CH3 | H | CF3 | H | CF3 | H | H | H | H |
| 575 | Ir | 2 | 1 | Ph | P1 | P1 | — | — | — | H | H | H | H | H | H | C4H9 | H |

TABLE 1-10-continued

| No | M | m | n | A | B | B' or B" | E | J | G | A-R1 | A-R2 | A-R3 | A-R4 | B-R5 | B-R6 | B-R7 | B-R8 |
|---|---|---|---|---|---|---|---|---|---|---|---|---|---|---|---|---|---|
| 576 | Ir | 2 | 1 | Ph | P1 | P1 | — | — | — | F | H | H | H | H | H | C4H9 | H |
| 577 | Ir | 2 | 1 | Ph | P1 | P1 | — | — | — | H | F | H | H | H | H | C4H9 | H |
| 578 | Ir | 2 | 1 | Ph | P1 | P1 | — | — | — | H | H | F | H | H | H | C4H9 | H |
| 579 | Ir | 2 | 1 | Ph | P1 | P1 | — | — | — | H | H | H | F | H | H | C4H9 | H |
| 580 | Ir | 2 | 1 | Ph | P1 | P1 | — | — | — | F | H | F | H | H | H | C4H9 | H |
| 581 | Ir | 2 | 1 | Ph | P1 | P1 | — | — | — | H | F | H | F | H | H | C4H9 | H |
| 582 | Ir | 2 | 1 | Ph | P1 | P1 | — | — | — | H | F | F | H | H | H | C4H9 | H |
| 583 | Ir | 2 | 1 | Ph | P1 | P1 | — | — | — | F | H | H | F | H | H | C4H9 | H |
| 584 | Ir | 2 | 1 | Ph | P1 | P1 | — | — | — | F | F | F | F | H | H | C4H9 | H |
| 585 | Ir | 2 | 1 | Ph | P1 | P1 | — | — | — | H | CF3 | H | H | H | H | C4H9 | H |
| 586 | Ir | 2 | 1 | Ph | P1 | P1 | — | — | — | H | H | H | CF3 | H | H | C4H9 | H |
| 587 | Ir | 2 | 1 | Ph | P1 | P1 | — | — | — | H | CF3 | H | CF3 | H | H | C4H9 | H |
| 588 | Ir | 2 | 1 | Ph | P1 | P1 | — | — | — | H | CF3 | F | H | H | H | C4H9 | H |
| 589 | Ir | 2 | 1 | Ph | P1 | P1 | — | — | — | F | CF3 | F | H | H | H | C4H9 | H |
| 590 | Ir | 2 | 1 | Ph | P1 | P1 | — | — | — | F | CF3 | H | H | H | H | C4H9 | H |
| 591 | Ir | 2 | 1 | Ph | P1 | P1 | — | — | — | H | H | F | CF3 | H | H | C4H9 | H |
| 592 | Ir | 2 | 1 | Ph | P1 | P1 | — | — | — | F | H | H | CF3 | H | H | C4H9 | H |
| 593 | Ir | 2 | 1 | Ph | P1 | P1 | — | — | — | F | H | F | CF3 | H | H | C4H9 | H |
| 594 | Ir | 2 | 1 | Ph | P1 | P1 | — | — | — | H | CH3 | H | H | H | H | C4H9 | H |
| 595 | Ir | 2 | 1 | Ph | P1 | P1 | — | — | — | H | H | CH3 | H | H | H | C4H9 | H |
| 596 | Ir | 2 | 1 | Ph | P1 | P1 | — | — | — | H | C2H5 | H | H | H | H | C4H9 | H |
| 597 | Ir | 2 | 1 | Ph | P1 | P1 | — | — | — | H | H | C2H5 | H | H | H | C4H9 | H |
| 598 | Ir | 2 | 1 | Ph | P1 | P1 | — | — | — | H | C4H9 | H | H | H | H | C4H9 | H |
| 599 | Ir | 2 | 1 | Ph | P1 | P1 | — | — | — | H | H | C4H9 | H | H | H | C4H9 | H |
| 600 | Ir | 2 | 1 | Ph | P1 | P1 | — | — | — | F | H | H | H | H | H | H | H |

TABLE 1-11

| No | M | m | n | A | B | B' or B" | A-R1 | A-R2 | A-R3 | A-R4 | B-R5 | B-R6 | B-R7 | B-R8 |
|---|---|---|---|---|---|---|---|---|---|---|---|---|---|---|
| 601 | Ir | 2 | 1 | Ph | P1 | P1 | H | F | H | H | H | H | H | H |
| 602 | Ir | 2 | 1 | Ph | P1 | P1 | H | H | F | H | H | H | H | H |
| 603 | Ir | 2 | 1 | Ph | P1 | P1 | H | H | H | F | H | H | H | H |
| 604 | Ir | 2 | 1 | Ph | P1 | P1 | H | F | H | F | H | H | H | H |
| 605 | Ir | 2 | 1 | Ph | P1 | P1 | H | F | F | H | H | H | H | H |
| 606 | Ir | 2 | 1 | Ph | P1 | P1 | F | H | H | F | H | H | H | H |
| 607 | Ir | 2 | 1 | Ph | P1 | P1 | F | F | F | F | H | H | H | H |
| 608 | Ir | 2 | 1 | Ph | P1 | P1 | H | CF3 | H | H | H | H | H | H |
| 609 | Ir | 2 | 1 | Ph | P1 | P1 | H | H | H | CF3 | H | H | H | H |
| 610 | Ir | 2 | 1 | Ph | P1 | P1 | H | CF3 | H | CF3 | H | H | H | H |
| 611 | Ir | 2 | 1 | Ph | P1 | P1 | H | CF3 | F | H | H | H | H | H |
| 612 | Ir | 2 | 1 | Ph | P1 | P1 | F | CF3 | F | H | H | H | H | H |
| 613 | Ir | 2 | 1 | Ph | P1 | P1 | F | CF3 | H | H | H | H | H | H |
| 614 | Ir | 2 | 1 | Ph | P1 | P1 | H | H | F | CF3 | H | H | H | H |
| 615 | Ir | 2 | 1 | Ph | P1 | P1 | F | H | H | CF3 | H | H | H | H |
| 616 | Ir | 2 | 1 | Ph | P1 | P1 | F | H | F | CF3 | H | H | H | H |
| 617 | Ir | 2 | 1 | Ph | P1 | P1 | H | CH3 | H | H | H | H | H | H |
| 618 | Ir | 2 | 1 | Ph | P1 | P1 | H | H | CH3 | H | H | H | H | H |
| 619 | Ir | 2 | 1 | Ph | P1 | P1 | H | C2H5 | H | H | H | H | H | H |
| 620 | Ir | 2 | 1 | Ph | P1 | P1 | H | H | C2H5 | H | H | H | H | H |
| 621 | Ir | 2 | 1 | Ph | P1 | P1 | H | C4H9 | H | H | H | H | H | H |
| 622 | Ir | 2 | 1 | Ph | P1 | P1 | H | H | C4H9 | H | H | H | H | H |
| 623 | Ir | 2 | 1 | Ph | P1 | P1 | H | H | H | H | H | H | H | CH3 |
| 624 | Ir | 2 | 1 | Ph | P1 | P1 | F | H | H | H | H | H | H | CH3 |
| 625 | Ir | 2 | 1 | Ph | P1 | P1 | H | F | H | H | H | H | H | CH3 |
| 626 | Ir | 2 | 1 | Ph | P1 | P1 | H | H | F | H | H | H | H | CH3 |
| 627 | Ir | 2 | 1 | Ph | P1 | P1 | H | H | H | F | H | H | H | CH3 |
| 628 | Ir | 2 | 1 | Ph | P1 | P1 | F | H | F | H | H | H | H | CH3 |
| 629 | Ir | 2 | 1 | Ph | P1 | P1 | H | F | H | F | H | H | H | CH3 |
| 630 | Ir | 2 | 1 | Ph | P1 | P1 | H | F | F | H | H | H | H | CH3 |
| 631 | Ir | 2 | 1 | Ph | P1 | P1 | F | H | H | F | H | H | H | CH3 |
| 632 | Ir | 2 | 1 | Ph | P1 | P1 | F | F | F | F | H | H | H | CH3 |
| 633 | Ir | 2 | 1 | Ph | P1 | P1 | H | CF3 | H | H | H | H | H | CH3 |
| 634 | Ir | 2 | 1 | Ph | P1 | P1 | H | H | H | CF3 | H | H | H | CH3 |
| 635 | Ir | 2 | 1 | Ph | P1 | P1 | H | CF3 | CF3 | H | H | H | H | CH3 |
| 636 | Ir | 2 | 1 | Ph | P1 | P1 | H | CF3 | F | H | H | H | H | CH3 |
| 637 | Ir | 2 | 1 | Ph | P1 | P1 | F | CF3 | F | H | H | H | H | CH3 |
| 638 | Ir | 2 | 1 | Ph | P1 | P1 | F | CF3 | H | H | H | H | H | CH3 |
| 639 | Ir | 2 | 1 | Ph | P1 | P1 | H | H | F | CF3 | H | H | H | CH3 |
| 640 | Ir | 2 | 1 | Ph | P1 | P1 | F | H | H | CF3 | H | H | H | CH3 |
| 641 | Ir | 2 | 1 | Ph | P1 | P1 | F | H | F | CF3 | H | H | H | CH3 |

TABLE 1-11-continued

| No | M | m | n | A | B | B' or B" | A-R1 | A-R2 | A-R3 | A-R4 | B-R5 | B-R6 | B-R7 | B-R8 |
|---|---|---|---|---|---|---|---|---|---|---|---|---|---|---|
| 642 | Ir | 2 | 1 | Ph | P1 | P1 | H | CH3 | H | H | H | H | H | CH3 |
| 643 | Ir | 2 | 1 | Ph | P1 | P1 | H | H | CH3 | H | H | H | H | CH3 |
| 644 | Ir | 2 | 1 | Ph | P1 | P1 | H | C2H5 | H | H | H | H | H | CH3 |
| 645 | Ir | 2 | 1 | Ph | P1 | P1 | H | H | C2H5 | H | H | H | H | CH3 |
| 646 | Ir | 2 | 1 | Ph | P1 | P1 | H | C4H9 | H | H | H | H | H | CH3 |
| 647 | Ir | 2 | 1 | Ph | P1 | P1 | H | H | C4H9 | H | H | H | H | CH3 |
| 648 | Ir | 3 | 0 | Ph | P2 | — | H | H | CH3 | H | H | H | H | — |
| 649 | Ir | 3 | 0 | Ph | P2 | — | H | H | C4H9 | H | H | H | H | — |
| 650 | Ir | 3 | 0 | Ph | P2 | — | F | H | F | H | H | H | H | — |
| 651 | Ir | 3 | 0 | Ph | P2 | — | H | H | F | H | H | H | H | — |
| 652 | Ir | 3 | 0 | Ph | P2 | — | H | CF3 | H | H | H | H | H | — |
| 653 | Ir | 3 | 0 | Ph | P2 | — | H | H | H | H | H | H | H | — |
| 654 | Ir | 3 | 0 | Ph | P2 | — | H | H | H | H | H | H | H | — |
| 655 | Ir | 3 | 0 | Ph | P2 | — | H | H | H | H | H | H | H | — |
| 656 | Ir | 3 | 0 | Ph | P2 | — | H | H | H | H | H | H | CH3 | — |
| 657 | Ir | 3 | 0 | Ph | P2 | — | H | H | H | H | H | CH3 | H | — |
| 658 | Ir | 3 | 0 | Ph | P3 | — | H | H | CH3 | H | H | H | H | — |
| 659 | Ir | 3 | 0 | Ph | P3 | — | H | H | C4H9 | H | H | H | H | — |
| 660 | Ir | 3 | 0 | Ph | P3 | — | F | H | F | H | H | H | H | — |

TABLE 1-12

| No | M | m | n | A | B | A-R1 | A-R2 | A-R3 | A-R4 | B-R5 | B-R6 | B-R7 | B-R8 |
|---|---|---|---|---|---|---|---|---|---|---|---|---|---|
| 661 | Ir | 3 | 0 | Ph | P3 | H | H | F | H | H | H | H | — |
| 662 | Ir | 3 | 0 | Ph | P3 | H | CF3 | H | H | H | H | H | — |
| 663 | Ir | 3 | 0 | Ph | P3 | H | H | H | H | H | H | H | — |
| 664 | Ir | 3 | 0 | Ph | P3 | H | H | H | H | H | H | H | — |
| 665 | Ir | 3 | 0 | Ph | P3 | H | H | H | H | H | H | H | — |
| 666 | Ir | 3 | 0 | Ph | P3 | H | H | H | H | CH3 | H | H | — |
| 667 | Ir | 3 | 0 | Ph | P3 | H | H | H | H | H | CH3 | H | — |
| 668 | Ir | 3 | 0 | Ph | P4 | H | H | CH3 | H | H | H | H | — |
| 669 | Ir | 3 | 0 | Ph | P4 | H | H | C4H9 | H | H | H | H | — |
| 670 | Ir | 3 | 0 | Ph | P4 | F | H | F | H | H | H | H | — |
| 671 | Ir | 3 | 0 | Ph | P4 | H | H | F | H | H | H | H | — |
| 672 | Ir | 3 | 0 | Ph | P4 | H | CF3 | H | H | H | H | H | — |
| 673 | Ir | 3 | 0 | Ph | P4 | H | H | H | H | H | H | H | — |
| 674 | Ir | 3 | 0 | Ph | P4 | H | H | H | H | H | H | H | — |
| 675 | Ir | 3 | 0 | Ph | P4 | H | H | H | H | H | H | H | — |
| 676 | Ir | 3 | 0 | Ph | P4 | H | H | H | H | CH3 | H | H | — |
| 677 | Ir | 3 | 0 | Ph | P4 | H | H | H | H | H | CH3 | H | — |
| 678 | Ir | 3 | 0 | Ph | P5 | H | H | CH3 | H | H | H | H | — |
| 679 | Ir | 3 | 0 | Ph | P5 | H | H | C4H9 | H | H | H | H | — |
| 680 | Ir | 3 | 0 | Ph | P5 | H | H | F | H | H | H | H | — |
| 681 | Ir | 3 | 0 | Ph | P5 | H | CF3 | H | H | H | H | H | — |
| 682 | Ir | 3 | 0 | Ph | P5 | H | H | H | H | H | CH3 | H | — |
| 683 | Ir | 3 | 0 | Ph | P6 | H | H | CH3 | H | H | H | H | H |
| 684 | Ir | 3 | 0 | Ph | P6 | H | H | C4H9 | H | H | H | H | H |
| 685 | Ir | 3 | 0 | Ph | P6 | H | H | F | H | H | H | H | H |
| 686 | Ir | 3 | 0 | Ph | P6 | H | CF3 | H | H | H | H | H | H |
| 687 | Ir | 3 | 0 | Ph | P6 | H | H | H | H | H | CH3 | H | H |
| 688 | Ir | 3 | 0 | Ph | P7 | H | H | CH3 | H | H | H | H | H |
| 689 | Ir | 3 | 0 | Ph | P7 | H | H | C4H9 | H | H | H | H | H |
| 690 | Ir | 3 | 0 | Ph | P7 | H | H | F | H | H | H | H | H |
| 691 | Ir | 3 | 0 | Ph | P7 | H | CF3 | H | H | H | H | H | H |
| 692 | Ir | 3 | 0 | Ph | P7 | H | H | H | H | H | CH3 | H | H |
| 693 | Ir | 3 | 0 | Ph | P8 | H | H | CH3 | H | H | H | H | H |
| 694 | Ir | 3 | 0 | Ph | P8 | H | H | C4H9 | H | H | H | H | H |
| 695 | Ir | 3 | 0 | Ph | P8 | H | H | F | H | H | H | H | H |
| 696 | Ir | 3 | 0 | Ph | P8 | H | H | H | H | H | H | CH3 | H |
| 697 | Ir | 3 | 0 | Ph | P8 | H | H | H | H | H | CH3 | H | H |
| 698 | Ir | 3 | 0 | Ph | P9 | H | H | CH3 | H | H | H | H | H |
| 699 | Ir | 3 | 0 | Ph | P9 | H | H | C4H9 | H | H | H | H | H |
| 700 | Ir | 3 | 0 | Ph | P9 | H | H | F | H | H | H | H | H |
| 701 | Ir | 3 | 0 | Ph | P9 | H | H | H | H | H | H | CH3 | H |
| 702 | Ir | 3 | 0 | Ph | P9 | H | H | H | H | H | CH3 | H | H |

TABLE 1-13

| No | M | m | n | A | B | A' | B' or B" | E | J | G | A-R1 | A-R2 | A-R3 |
|---|---|---|---|---|---|---|---|---|---|---|---|---|---|
| 703 | Ir | 2 | 1 | Ph | P1 | Ph | P1 | — | — | — | H | H | H |
| 704 | Ir | 2 | 1 | Ph | P1 | Tn1 | P1 | — | — | — | H | H | CH3 |
| 705 | Ir | 2 | 1 | Ph | P1 | Tn1 | P6 | — | — | — | H | H | H |
| 706 | Ir | 2 | 1 | Ph | P1 | Tn1 | P8 | — | — | — | H | H | CH3 |
| 707 | Ir | 2 | 1 | Ph | P1 | Tn2 | P1 | — | — | — | H | H | H |
| 708 | Ir | 2 | 1 | Ph | P1 | Tn3 | P1 | — | — | — | H | H | CH3 |
| 709 | Ir | 2 | 1 | Ph | P1 | Np1 | P1 | — | — | — | H | H | H |
| 710 | Ir | 2 | 1 | Ph | P1 | Np2 | P1 | — | — | — | H | H | CH3 |
| 711 | Ir | 2 | 1 | Ph | P1 | Np2 | P6 | — | — | — | H | H | H |
| 712 | Ir | 2 | 1 | Ph | P1 | Np2 | P8 | — | — | — | H | H | H |
| 713 | Ir | 2 | 1 | Ph | P1 | Pe | P1 | — | — | — | H | H | H |
| 714 | Ir | 2 | 1 | Ph | P1 | Cn1 | P1 | — | — | — | H | H | H |
| 715 | Ir | 2 | 1 | Ph | P1 | Cn2 | P1 | — | — | — | H | H | H |
| 716 | Ir | 2 | 1 | Ph | P1 | F1 | P1 | — | — | — | H | H | H |
| 717 | Ir | 2 | 1 | Ph | P1 | F1 | P1 | — | — | — | H | H | CH3 |
| 718 | Ir | 2 | 1 | Ph | P1 | F1 | P6 | — | — | — | H | H | CH3 |
| 719 | Ir | 2 | 1 | Ph | P1 | F1 | P8 | — | — | — | H | H | CH3 |
| 720 | Ir | 2 | 1 | Ph | P1 | Qn1 | P1 | — | — | — | H | H | H |
| 721 | Ir | 2 | 1 | Ph | P1 | Cz | P1 | — | — | — | H | H | CH3 |
| 722 | Ir | 2 | 1 | Ph | P1 | Fn1 | P1 | — | — | — | H | H | CH3 |
| 723 | Ir | 3 | 0 | Tn1 | P1 | — | — | — | — | — | CH3 | H | — |
| 724 | Ir | 3 | 0 | Tn1 | P1 | — | — | — | — | — | C2H5 | H | — |
| 725 | Ir | 3 | 0 | Tn1 | P1 | — | — | — | — | — | C4H9 | H | — |
| 726 | Ir | 3 | 0 | Tn1 | P1 | — | — | — | — | — | F | H | — |
| 727 | Ir | 3 | 0 | Tn1 | P1 | — | — | — | — | — | CF3 | H | — |
| 728 | Ir | 3 | 0 | Tn1 | P1 | — | — | — | — | — | H | CH3 | — |
| 729 | Ir | 3 | 0 | Tn1 | P1 | — | — | — | — | — | H | H | — |
| 730 | Ir | 3 | 0 | Tn1 | P1 | — | — | — | — | — | CH3 | H | — |
| 731 | Ir | 3 | 0 | Tn1 | P1 | — | — | — | — | — | H | H | — |
| 732 | Ir | 3 | 0 | Tn1 | P6 | — | — | — | — | — | CH3 | H | — |
| 733 | Ir | 2 | 1 | Tn1 | P1 | — | — | CH3 | CH3 | CH3 | H | H | — |
| 734 | Ir | 2 | 1 | Tn1 | P5 | — | — | CH3 | H | CH3 | CH3 | H | — |
| 735 | Ir | 3 | 0 | Tn2 | P1 | — | — | — | — | — | H | CF3 | — |
| 736 | Ir | 3 | 0 | Tn2 | P1 | — | — | — | — | — | H | CF3 | — |
| 737 | Ir | 3 | 0 | Tn2 | P1 | — | — | — | — | — | H | CF3 | — |
| 738 | Ir | 3 | 0 | Tn2 | P1 | — | — | — | — | — | H | CF3 | — |
| 739 | Ir | 3 | 0 | Tn2 | P1 | — | — | — | — | — | H | H | — |
| 740 | Ir | 2 | 1 | Tn2 | P1 | — | — | CH3 | F | CH3 | H | H | — |
| 741 | Ir | 2 | 1 | Tn2 | P1 | — | P1 | — | — | — | H | CH3 | — |
| 742 | Ir | 2 | 1 | Tn2 | P1 | — | P1 | — | — | — | H | H | — |
| 743 | Ir | 2 | 1 | Tn2 | P1 | — | P1 | — | — | — | H | H | — |

| No | A-R4 | A'-R1 | A'-R2 | A'-R3 | A'-R4 | B-R5 | B-R6 | B-R7 | B-R8 | B'-R5 | B'-R6 | B'-R7 | B'-R8 |
|---|---|---|---|---|---|---|---|---|---|---|---|---|---|
| 703 | H | H | H | CH3 | H | H | H | H | H | H | H | H | H |
| 704 | H | H | H | — | — | H | H | H | H | H | H | H | H |
| 705 | H | CH3 | H | — | — | H | H | H | H | H | H | H | H |
| 706 | H | H | H | — | — | H | H | H | H | H | H | H | H |
| 707 | H | H | CH3 | — | — | H | H | H | H | H | H | H | H |
| 708 | H | H | H | H | H | H | H | H | H | H | H | H | H |
| 709 | H | CH3 | H | H | H | H | H | H | H | H | H | H | H |
| 710 | H | H | H | H | H | H | H | H | H | H | H | H | H |
| 711 | H | H | H | H | H | H | CH3 | H | H | H | H | H | H |
| 712 | H | H | H | H | H | H | H | CH3 | H | H | H | H | H |
| 713 | H | H | H | H | H | H | H | H | H | H | H | H | H |
| 714 | H | H | H | — | — | H | H | H | H | H | H | H | H |
| 715 | H | H | H | — | — | H | H | H | H | H | H | H | H |
| 716 | H | H | H | Ph | H | H | H | H | H | H | H | H | H |
| 717 | H | H | H | H | H | H | H | H | H | H | H | H | H |
| 718 | H | H | H | H | H | H | H | H | H | H | H | H | H |
| 719 | H | H | H | H | H | H | H | H | H | H | H | H | H |
| 720 | H | CH3 | H | H | — | H | H | H | H | H | H | H | H |
| 721 | H | H | H | H | H | H | H | H | H | H | H | H | H |
| 722 | H | H | H | H | H | H | H | H | H | H | H | H | H |
| 723 | — | — | — | — | — | H | H | H | H | — | — | — | — |
| 724 | — | — | — | — | — | H | H | H | H | — | — | — | — |
| 725 | — | — | — | — | — | H | H | H | H | — | — | — | — |
| 726 | — | — | — | — | — | H | H | H | H | — | — | — | — |
| 727 | — | — | — | — | — | H | H | H | H | — | — | — | — |
| 728 | — | — | — | — | — | H | H | H | H | — | — | — | — |
| 729 | — | — | — | — | — | H | H | CF3 | H | — | — | — | — |
| 730 | — | — | — | — | — | H | H | CF3 | H | — | — | — | — |
| 731 | — | — | — | — | — | H | H | CH3 | H | — | — | — | — |
| 732 | — | — | — | — | — | H | H | H | H | — | — | — | — |
| 733 | — | — | — | — | — | H | H | H | H | — | — | — | — |
| 733 | — | — | — | — | — | H | H | H | H | — | — | — | — |
| 734 | — | — | — | — | — | H | H | H | H | — | — | — | — |

TABLE 1-13-continued

| | | | | | | | | | | | | | |
|---|---|---|---|---|---|---|---|---|---|---|---|---|---|
| 735 | — | — | — | — | — | H | H | H | H | — | — | — | — |
| 736 | — | — | — | — | — | H | H | H | H | — | — | — | — |
| 737 | — | — | — | — | — | H | H | CH3 | H | — | — | — | — |
| 738 | — | — | — | — | — | H | H | H | CH3 | — | — | — | — |
| 739 | — | — | — | — | — | H | H | CH3 | H | — | — | — | — |
| 740 | — | — | — | — | — | H | H | H | H | — | — | — | — |
| 741 | — | — | — | — | — | H | H | H | H | H | H | H | H |
| 742 | — | — | — | — | — | H | H | H | H | H | C4H9 | H |
| 743 | — | — | — | — | — | H | H | CH3 | H | H | H | H |

TABLE 1-14

| No | M | m | n | A | B | B' or B" | E | J | G | A-R1 | A-R2 | A-R3 | A-R4 | B-R5 | B-R6 | B-R7 | B-R8 | B'-R5 | B'-R6 | B'-R7 | B'-R8 |
|---|---|---|---|---|---|---|---|---|---|---|---|---|---|---|---|---|---|---|---|---|---|
| 744 | Ir | 3 | 0 | Tn3 | P1 | — | — | — | — | H | H | H | H | H | H | CH3 | H | — | — | — | — |
| 745 | Ir | 3 | 0 | Tn3 | P1 | — | — | — | — | H | H | H | H | H | CH3 | H | H | — | — | — | — |
| 746 | Ir | 3 | 0 | Tn3 | P1 | — | — | — | — | H | H | H | H | H | H | CF3 | H | — | — | — | — |
| 747 | Ir | 3 | 0 | Tn3 | P1 | — | — | — | — | H | H | H | H | H | H | CF3 | H | — | — | — | — |
| 748 | Ir | 2 | 1 | Tn3 | P1 | — | CH3 | CH3 | CH3 | H | H | H | H | H | H | H | H | — | — | — | — |
| 749 | Ir | 2 | 1 | Tn3 | P1 | — | CH3 | H | CH3 | H | H | H | H | H | H | CF3 | H | — | — | — | — |
| 750 | Ir | 2 | 1 | Tn3 | P1 | — | CH3 | F | CH3 | H | H | H | H | H | H | H | H | — | — | — | — |
| 751 | Ir | 3 | 0 | Np1 | P1 | — | — | — | — | CH3 | H | H | H | H | H | H | H | — | — | — | — |
| 752 | Ir | 3 | 0 | Np1 | P1 | — | — | — | — | CH3 | H | H | H | H | CH3 | H | H | — | — | — | — |
| 753 | Ir | 3 | 0 | Np1 | P1 | — | — | — | — | CH3 | H | H | H | H | H | CH3 | H | — | — | — | — |
| 754 | Ir | 3 | 0 | Np1 | P1 | — | — | — | — | CH3 | H | H | H | H | CF3 | H | H | — | — | — | — |
| 755 | Ir | 3 | 0 | Np1 | P1 | — | — | — | — | CH3 | H | H | H | H | H | CF3 | H | — | — | — | — |
| 756 | Ir | 3 | 0 | Np1 | P1 | — | — | — | — | F | H | H | H | H | H | H | H | — | — | — | — |
| 757 | Ir | 3 | 0 | Np1 | P1 | — | — | — | — | CF3 | H | H | H | H | H | H | H | — | — | — | — |
| 758 | Ir | 3 | 0 | Np1 | P1 | — | — | — | — | Ph | H | H | H | H | H | H | H | — | — | — | — |
| 759 | Ir | 3 | 0 | Np1 | P1 | — | — | — | — | F | H | H | H | H | H | CF3 | H | — | — | — | — |
| 760 | Ir | 2 | 1 | Np1 | P1 | — | CH3 | H | CH3 | CH3 | H | H | H | H | H | H | H | — | — | — | — |
| 761 | Ir | 2 | 1 | Np1 | P1 | — | CH3 | CH3 | CH3 | CH3 | H | H | H | H | H | H | H | — | — | — | — |
| 762 | Ir | 2 | 1 | Np1 | P1 | — | CH3 | F | CH3 | CH3 | H | H | H | H | H | H | H | — | — | — | — |
| 763 | Ir | 2 | 1 | Np1 | P1 | — | CH3 | C2H5 | CH3 | CH3 | H | H | H | H | H | H | H | — | — | — | — |
| 764 | Ir | 2 | 1 | Np1 | P1 | — | CH3 | H | CH3 | CH3 | H | H | H | H | H | CF3 | H | — | — | — | — |
| 765 | Ir | 2 | 1 | Np1 | P1 | P1 | — | — | — | CH3 | H | H | H | H | H | H | H | H | H | H | H |
| 766 | Ir | 2 | 1 | Np1 | P1 | P1 | — | — | — | CH3 | H | H | H | H | CF3 | H | H | H | H | H | H |
| 767 | Ir | 3 | 0 | Np2 | P1 | — | — | — | — | H | H | H | H | H | H | CH3 | H | — | — | — | — |
| 768 | Ir | 3 | 0 | Np2 | P1 | — | — | — | — | H | H | H | H | H | CH3 | H | H | — | — | — | — |
| 769 | Ir | 3 | 0 | Np2 | P1 | — | — | — | — | H | CH3 | H | H | H | H | H | H | — | — | — | — |
| 770 | Ir | 3 | 0 | Np2 | P1 | — | — | — | — | H | H | CH3 | H | H | H | H | H | — | — | — | — |
| 771 | Ir | 3 | 0 | Np2 | P1 | — | — | — | — | H | H | F | H | H | H | H | H | — | — | — | — |
| 772 | Ir | 2 | 1 | Np2 | P1 | — | CH3 | CH3 | CH3 | H | H | H | H | H | H | H | H | — | — | — | — |
| 773 | Ir | 2 | 1 | Np2 | P6 | — | CH3 | H | CH3 | H | H | CH3 | H | H | H | H | H | — | — | — | — |
| 774 | Ir | 3 | 0 | Pe | P1 | — | — | — | — | H | H | H | H | H | CH3 | H | H | — | — | — | — |
| 775 | Ir | 3 | 0 | Pe | P1 | — | — | — | — | H | H | H | H | H | H | CH3 | H | — | — | — | — |
| 776 | Ir | 3 | 0 | Pe | P1 | — | — | — | — | H | H | H | H | CH3 | H | H | H | — | — | — | — |
| 777 | Ir | 3 | 0 | Pe | P1 | — | — | — | — | H | H | H | H | H | CF3 | H | H | — | — | — | — |
| 778 | Ir | 2 | 1 | Pe | P1 | — | CH3 | H | CH3 | H | H | H | H | H | H | H | H | — | — | — | — |
| 779 | Ir | 2 | 1 | Pe | P1 | P1 | — | — | — | H | H | H | H | H | H | CH3 | H | H | H | H | H |
| 780 | Ir | 3 | 0 | Fl | P1 | — | — | — | — | H | H | CH3 | H | H | H | H | H | — | — | — | — |

TABLE 1-15

| No | M | m | n | A | B | B' or B" | E | J | G | A-R1 | A-R2 | A-R3 | A-R4 | B-R5 | B-R6 | B-R7 | B-R8 | B'-R5 | B'-R6 | B'-R7 | B'-R8 |
|---|---|---|---|---|---|---|---|---|---|---|---|---|---|---|---|---|---|---|---|---|---|
| 781 | Ir | 3 | 0 | Fl | P1 | — | — | — | — | H | H | C2H5 | H | H | H | H | H | — | — | — | — |
| 782 | Ir | 3 | 0 | Fl | P1 | — | — | — | — | H | H | H | H | H | CH3 | H | H | — | — | — | — |
| 783 | Ir | 3 | 0 | Fl | P1 | — | — | — | — | H | H | H | H | CH3 | H | H | H | — | — | — | — |
| 784 | Ir | 3 | 0 | Fl | P1 | — | — | — | — | H | H | CH3 | H | H | CH3 | H | H | — | — | — | — |
| 785 | Ir | 3 | 0 | Fl | P6 | — | — | — | — | H | H | Ph | H | H | H | H | H | — | — | — | — |
| 786 | Ir | 3 | 0 | Fl | P6 | — | — | — | — | H | H | Ch3 | H | H | H | H | H | — | — | — | — |
| 787 | Ir | 2 | 1 | Fl | P1 | — | CH3 | H | CH3 | H | H | CH3 | H | H | H | H | H | — | — | — | — |
| 788 | Ir | 2 | 1 | Fl | P1 | — | CH3O | CH3 | CH3 | H | H | H | H | H | H | H | H | — | — | — | — |
| 789 | Ir | 2 | 1 | Fl | P6 | — | CH3 | H | CH3 | H | H | CH3 | H | H | H | H | H | — | — | — | — |
| 790 | Ir | 2 | 1 | Fl | P6 | — | CH3O | CH3 | CH3 | H | H | H | H | H | H | H | H | — | — | — | — |
| 791 | Ir | 3 | 0 | Qn1 | P1 | — | — | — | — | H | H | CH3 | H | H | H | H | H | — | — | — | — |

TABLE 1-15-continued

| No | M | m | n | A | B | B' or B" | E | J | G | A-R1 | A-R2 | A-R3 | A-R4 | B-R5 | B-R6 | B-R7 | B-R8 | B'-R5 | B'-R6 | B'-R7 | B'-R8 |
|----|---|---|---|-----|----|----|------|-----|------|---|------|------|------|------|------|------|------|---|---|---|---|
| 792 | Ir | 3 | 0 | Qn1 | P3 | — | — | — | — | H | H | CH3 | H | H | H | H | H | — | — | — | — |
| 793 | Ir | 3 | 0 | Qn2 | P1 | — | — | — | — | H | CH3 | H | H | H | H | H | H | — | — | — | — |
| 794 | Ir | 3 | 0 | Qn2 | P8 | — | — | — | — | H | CH3 | H | H | H | H | H | H | — | — | — | — |
| 795 | Ir | 3 | 0 | Cz | P1 | — | — | — | — | H | CH3 | H | H | H | H | H | H | — | — | — | — |
| 796 | Ir | 3 | 0 | Cz | P1 | — | — | — | — | H | C2H5 | H | H | H | H | H | H | — | — | — | — |
| 797 | Ir | 3 | 0 | Cz | P1 | — | — | — | — | H | C4H9 | H | H | H | H | H | H | — | — | — | — |
| 798 | Ir | 3 | 0 | Cz | P1 | — | — | — | — | H | C8H17 | H | H | H | H | H | H | — | — | — | — |
| 799 | Ir | 3 | 0 | Cz | P1 | — | — | — | — | H | CH3 | H | CH3 | H | H | H | H | — | — | — | — |
| 800 | Ir | 3 | 0 | Cz | P1 | — | — | — | — | H | C2H5 | H | CH3 | H | H | H | H | — | — | — | — |
| 801 | Ir | 3 | 0 | Cz | P1 | — | — | — | — | H | CH3 | H | H | CH3 | H | H | H | — | — | — | — |
| 802 | Ir | 3 | 0 | Cz | P1 | — | — | — | — | H | CH3 | H | H | H | CH3 | H | H | — | — | — | — |
| 803 | Ir | 3 | 0 | Cz | P1 | — | — | — | — | H | Ph | H | H | H | H | H | H | — | — | — | — |
| 804 | Ir | 3 | 0 | Cz | P6 | — | — | — | — | H | CH3 | H | H | H | H | H | H | — | — | — | — |
| 805 | Ir | 2 | 1 | Cz | P1 | — | CH3 | H | CH3 | H | CH3 | H | H | H | H | H | H | — | — | — | — |
| 806 | Ir | 2 | 1 | Cz | P1 | — | CH3O | CH3 | CH3 | H | CH3 | H | H | H | H | H | H | — | — | — | — |
| 807 | Ir | 2 | 1 | Cz | P1 | — | CH3 | F | CH3 | H | CH3 | H | H | H | H | H | H | — | — | — | — |
| 808 | Ir | 2 | 1 | Cz | P1 | P1 | — | — | — | H | CH3 | H | H | H | H | H | H | H | H | H | H |
| 809 | Ir | 3 | 0 | Fn1 | P1 | — | — | — | — | H | H | H | H | H | H | CH3 | H | — | — | — | — |
| 810 | Ir | 3 | 0 | Fn1 | P1 | — | — | — | — | H | H | H | H | CH3 | H | H | H | — | — | — | — |
| 811 | Ir | 3 | 0 | Fn1 | P1 | — | — | — | — | H | H | H | H | CH3 | H | H | H | — | — | — | — |
| 812 | Ir | 3 | 0 | Fn1 | P3 | — | — | — | — | H | H | H | H | H | CH3 | — | — | — | — | — | — |
| 813 | Ir | 2 | 1 | Fn1 | P1 | — | CH3 | H | CH3 | H | H | H | H | H | H | CH3 | H | — | — | — | — |
| 814 | Ir | 2 | 1 | Fn1 | P1 | — | CH3O | CH3 | CH3 | H | H | H | H | H | H | H | H | — | — | — | — |
| 815 | Ir | 2 | 1 | Fn1 | P1 | — | CH3 | F | CH3 | H | H | H | H | H | H | H | H | — | — | — | — |
| 816 | Ir | 2 | 1 | Fn1 | P1 | P1 | — | — | — | H | H | H | H | H | H | C4H9 | H | — | — | — | — |
| 817 | Rh | 3 | 0 | Ph | P1 | — | — | — | — | H | H | CH3 | H | H | H | H | H | — | — | — | — |
| 818 | Rh | 3 | 0 | Ph | P1 | — | — | — | — | H | CH3 | H | H | H | H | H | H | — | — | — | — |
| 819 | Rh | 3 | 0 | Ph | P1 | — | — | — | — | H | H | C2H5 | H | H | H | H | H | — | — | — | — |
| 820 | Rh | 3 | 0 | Ph | P1 | — | — | — | — | H | H | C2H9 | H | H | H | H | H | — | — | — | — |

TABLE 1-16

| No | M | m | n | A | B | B' or B" | E | J | G | A-R1 | A-R2 | A-R3 | A-R4 | B-R5 | B-R6 | B-R7 | B-R8 | B'-R5 | B'-R6 | B'-R7 | B'-R8 |
|----|---|---|---|----|----|----|---|---|---|------|------|------|------|------|------|------|------|---|---|---|---|
| 821 | Rh | 3 | 0 | Ph | P1 | — | — | — | — | H | CF3 | H | H | H | H | H | H | — | — | — | — |
| 822 | Rh | 3 | 0 | Ph | P1 | — | — | — | — | H | H | F | H | H | H | H | H | — | — | — | — |
| 823 | Rh | 3 | 0 | Ph | P1 | — | — | — | — | F | H | F | H | H | H | H | H | — | — | — | — |
| 824 | Rh | 3 | 0 | Ph | P1 | — | — | — | — | H | CF3 | F | H | H | H | H | H | — | — | — | — |
| 825 | Rh | 3 | 0 | Ph | P1 | — | — | — | — | H | CF3 | H | CF3 | H | H | H | H | — | — | — | — |
| 826 | Rh | 3 | 0 | Ph | P1 | — | — | — | — | F | CF3 | F | H | H | H | H | H | — | — | — | — |
| 827 | Rh | 3 | 0 | Ph | P1 | — | — | — | — | H | CF3 | H | H | H | H | CH3 | H | — | — | — | — |
| 828 | Rh | 3 | 0 | Ph | P6 | — | — | — | — | H | CH3 | H | H | H | H | H | H | — | — | — | — |
| 829 | Rh | 3 | 0 | Fl | P1 | — | — | — | — | H | H | H | H | H | CH3 | H | H | — | — | — | — |
| 830 | Rh | 3 | 0 | Fl | P1 | — | — | — | — | H | H | H | H | H | CH3 | H | H | — | — | — | — |
| 831 | Rh | 2 | 1 | Ph | P1 | — | CH3 | H | CH3 | H | H | F | H | H | H | H | H | — | — | — | — |
| 832 | Rh | 2 | 1 | Ph | P1 | — | CH3O | CH3 | CH3 | H | H | F | H | H | H | H | H | — | — | — | — |
| 833 | Rh | 2 | 1 | Ph | P1 | — | CH3 | F | CH3 | H | H | F | H | H | H | H | H | — | — | — | — |
| 834 | Rh | 2 | 1 | Ph | P1 | P1 | — | — | — | H | H | F | H | H | H | H | H | H | H | H | H |
| 835 | Rh | 2 | 1 | Ph | P1 | P1 | — | — | — | F | H | F | H | H | H | H | H | H | H | H | H |
| 836 | Pt | 2 | 0 | Ph | P1 | — | — | — | — | H | CH3 | H | H | H | H | H | H | — | — | — | — |
| 837 | Pt | 2 | 0 | Ph | P1 | — | — | — | — | H | H | CH3 | H | H | H | H | H | — | — | — | — |
| 838 | Pt | 2 | 0 | Ph | P1 | — | — | — | — | H | C2H5 | H | H | H | H | H | H | — | — | — | — |
| 839 | Pt | 2 | 0 | Ph | P1 | — | — | — | — | H | H | C2H5 | H | H | H | H | H | — | — | — | — |
| 840 | Pt | 2 | 0 | Ph | P1 | — | — | — | — | H | H | C4H9 | H | H | H | H | H | — | — | — | — |
| 841 | Pt | 2 | 0 | Ph | P1 | — | — | — | — | H | H | C8H17 | H | H | H | H | H | — | — | — | — |
| 842 | Pt | 2 | 0 | Ph | P1 | — | — | — | — | H | H | C16H33 | H | H | H | H | H | — | — | — | — |
| 843 | Pt | 2 | 0 | Ph | P1 | — | — | — | — | H | H | CH3O | H | H | H | H | H | — | — | — | — |
| 844 | Pt | 2 | 0 | Ph | P1 | — | — | — | — | H | H | C2H5O | H | H | H | H | H | — | — | — | — |
| 845 | Pt | 2 | 0 | Ph | P1 | — | — | — | — | H | C2H4O | H | H | H | H | H | H | — | — | — | — |
| 846 | Pt | 2 | 0 | Ph | P1 | — | — | — | — | H | CF3 | H | H | H | H | H | H | — | — | — | — |
| 847 | Pt | 2 | 0 | Ph | P1 | — | — | — | — | H | H | F | H | H | H | H | H | — | — | — | — |
| 848 | Pt | 2 | 0 | Ph | P1 | — | — | — | — | H | CF3 | F | H | H | H | H | H | — | — | — | — |
| 849 | Pt | 2 | 0 | Ph | P1 | — | — | — | — | H | CF3 | H | CF3 | H | H | H | H | — | — | — | — |
| 850 | Pt | 2 | 0 | Ph | P1 | — | — | — | — | F | H | F | H | H | H | H | H | — | — | — | — |
| 851 | Pt | 2 | 0 | Ph | P1 | — | — | — | — | F | CF3 | F | H | H | H | H | H | — | — | — | — |
| 852 | Pt | 2 | 0 | Ph | P1 | — | — | — | — | H | CF3 | F | CF3 | H | H | H | H | — | — | — | — |
| 853 | Pt | 2 | 0 | Ph | P1 | — | — | — | — | H | H | CH3 | H | H | H | CH3 | H | — | — | — | — |
| 854 | Pt | 2 | 0 | Ph | P1 | — | — | — | — | H | H | C2H5 | H | H | H | CH3 | H | — | — | — | — |
| 855 | Pt | 2 | 0 | Ph | P1 | — | — | — | — | H | H | C2H5 | H | H | H | CH3 | H | — | — | — | — |
| 856 | Pt | 2 | 0 | Ph | P1 | — | — | — | — | H | H | C4H9 | H | H | H | CH3 | H | — | — | — | — |
| 857 | Pt | 2 | 0 | Ph | P1 | — | — | — | — | H | H | C8H17 | H | H | H | CH3 | H | — | — | — | — |
| 858 | Pt | 2 | 0 | Ph | P1 | — | — | — | — | H | H | C16H33 | H | H | H | CH3 | H | — | — | — | — |

TABLE 1-16-continued

| No | M | m | n | A | B | B' or B" | E | J | G | A-R1 | A-R2 | A-R3 | A-R4 | B-R5 | B-R6 | B-R7 | B-R8 | B'-R5 | B'-R6 | B'-R7 | B'-R8 |
|---|---|---|---|---|---|---|---|---|---|---|---|---|---|---|---|---|---|---|---|---|---|
| 859 | Pt | 2 | 0 | Ph | P1 | — | — | — | — | H | H | CH3O | H | H | H | CH3 | H | — | — | — | — |
| 860 | Pt | 2 | 0 | Ph | P1 | — | — | — | — | H | H | C2H5O | H | H | H | CH3 | H | — | — | — | — |

TABLE 1-17

| No | M | m | n | A | B | A' | B' or B" | E | J | G | A-R1 | A-R2 | A-R3 | A-R4 | B-R5 | B-R6 | B-R7 | B-R8 | B'-R5 | B'-R6 | B'-R7 | B'-R8 |
|---|---|---|---|---|---|---|---|---|---|---|---|---|---|---|---|---|---|---|---|---|---|---|
| 861 | Pt | 2 | 0 | Ph | P1 | — | — | — | — | — | H | C2H4O | H | H | H | H | CH3 | H | — | — | — | — |
| 862 | Pt | 2 | 0 | Ph | P1 | — | — | — | — | — | H | CF3 | H | H | H | H | CH3 | H | — | — | — | — |
| 863 | Pt | 2 | 0 | Ph | P1 | — | — | — | — | — | H | H | F | H | H | H | CH3 | H | — | — | — | — |
| 864 | Pt | 2 | 0 | Ph | P1 | — | — | — | — | — | H | CF3 | F | H | H | H | CH3 | H | — | — | — | — |
| 865 | Pt | 2 | 0 | Ph | P1 | — | — | — | — | — | H | CF3 | H | CF3 | H | H | CH3 | H | — | — | — | — |
| 866 | Pt | 2 | 0 | Ph | P1 | — | — | — | — | — | F | H | F | H | H | H | CH3 | H | — | — | — | — |
| 867 | Pt | 2 | 0 | Ph | P1 | — | — | — | — | — | F | CF3 | F | H | H | H | CH3 | H | — | — | — | — |
| 868 | Pt | 2 | 0 | Ph | P1 | — | — | — | — | — | H | CF3 | F | CF3 | H | H | CH3 | H | — | — | — | — |
| 869 | Pt | 1 | 1 | Ph | P1 | — | — | CH3 | H | CH3 | H | CH3 | H | H | H | H | H | H | — | — | — | — |
| 870 | Pt | 1 | 1 | Ph | P1 | — | — | CH3 | CH3 | CH3 | H | H | F | H | H | H | H | H | — | — | — | — |
| 871 | Pt | 1 | 1 | Ph | P1 | — | — | CH3 | F | CH3 | F | H | F | H | H | H | H | H | — | — | — | — |
| 872 | Pt | 1 | 1 | Ph | P1 | — | — | CH3 | F | CH3 | H | CF3 | F | H | H | H | H | H | — | — | — | — |
| 873 | Pt | 1 | 1 | Ph | P1 | — | P1 | — | — | — | H | CF3 | F | H | H | H | H | H | H | H | C4H9 | H |
| 874 | Pt | 1 | 1 | Ph | P1 | — | P1 | — | — | — | H | CF3 | F | H | H | H | H | H | — | — | — | — |
| 875 | Pt | 1 | 1 | Ph | P1 | Tn1 | P1 | — | — | — | CH3 | H | H | H | H | H | H | H | — | — | — | — |
| 876 | Pt | 1 | 1 | Ph | P1 | Np1 | P1 | — | — | — | CH3 | H | H | H | H | H | H | H | — | — | — | — |
| 877 | Pd | 2 | 0 | Ph | P1 | — | — | — | — | — | H | H | CH3 | H | H | H | H | H | — | — | — | — |
| 878 | Pd | 2 | 0 | Ph | P1 | — | — | — | — | — | H | H | C2H5 | H | H | H | H | H | — | — | — | — |
| 879 | Pd | 2 | 0 | Ph | P1 | — | — | — | — | — | H | H | F | H | H | H | H | H | — | — | — | — |
| 880 | Pd | 2 | 0 | Ph | P6 | — | — | — | — | — | H | CF3 | F | H | H | H | H | H | — | — | — | — |
| 881 | Pd | 2 | 0 | Cz | P1 | — | — | — | — | — | H | CH3 | H | H | H | H | H | H | — | — | — | — |
| 882 | Pd | 1 | 1 | Ph | P1 | — | — | CH3 | H | CH3 | H | H | H | H | H | H | H | H | — | — | — | — |
| 883 | Pd | 1 | 1 | Ph | P1 | — | P1 | — | — | — | H | H | CH3 | H | H | H | H | H | — | — | — | — |

Hereinbelow, the present invention will be described more specifically based on Examples.

Iridium metal coordination compounds used in Examples were synthesized along synthesis paths shown below. (Analogous reactions are described in Inorg. Chem. 1994, 33, p. 545).

<<Synthesis of Iridium Metal Coordination Compounds>>

A process scheme for synthesizing iridium complexes used in the present invention is shown below.

EXAMPLE 1

Synthesis of Example Compound No. 729

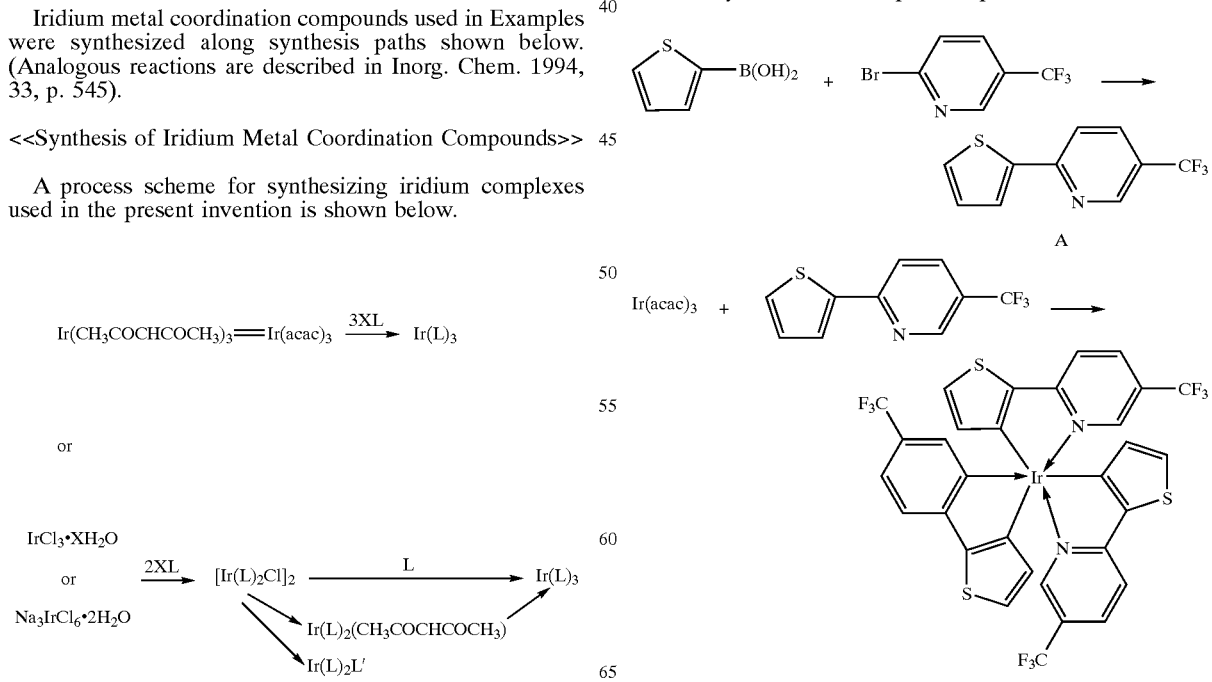

In a 100 ml-three-necked flask, 3.18 g (24.9 mmol) of thienylboronic acid, 5.65 g (25.0 mmol) of 1-bromo-4-trifluoromethylpyridine, 25 m of toluene, 12.5 ml of ethanol and 25 ml of 2M-sodium carbonate aqueous solution, were placed and stirred at room temperature under a nitrogen stream, followed by addition of 0.98 g (0.85 mmol) of tetrakis(triphenylphosphine)palladium (0). Thereafter, the system was refluxed under stirring and nitrogen stream for 8 hours. After completion of the reaction, the reaction product was cooled and extracted by adding cold water and toluene. The organic layer was washed with saline water and dried on magnesium sulfate, followed by removal of the solvent under a reduced pressure to provide dry solid. The residue was purified by silica gel column chromatography (eluent: chloroform/methanol=10/1) to obtain 4.20 g (yield= 74%) of Compound A.

In a 100 ml-four-necked flask, 50 ml of glycerol was placed and heated for 2 hours at 130–140° C. under stirring and bubbling with nitrogen. The glycerol was cooled to room temperature and poured into 300 ml of 1N-hydrochloric acid, and the precipitate was filtered out and washed with water. The precipitate was then purified by silica gel chromatography with chloroform as eluent, to obtain 0.33 g (yield: 38%) of red powdery Example Compound No. 729.

A toluene solution of the compound exhibited a luminescence spectrum showing λmax=563 nm. The compound was subjected to MALDI-TOF (matrix-assisted laser desorption ionization time-of-flight mass spectroscopy) by using an apparatus ("REFLEX-III", made by Bruker Co.). In the method, an ion obtained by removing one electron from a sample substance is subjected to measurement of a mass thereof, so that the measured mass is denoted by $M^+$, and the method is frequently used for identification of a substance. The measured $M^+$ value was 877.0 from which the objective product was confirmed.

For confirmation of phosphorescence-type luminescence, the Example Compound was dissolved in chloroform, and the solution was separately aerated with oxygen or nitrogen, each followed by photoirradiation for comparison of photoluminescence. As a result, substantially no luminescence attributable to the iridium complex was recognized with respect to the oxygen-aerated solution, whereas photoluminescence was confirmed with respect to the nitrogen-aerated solution. From these results, the compound of the present invention was confirmed to be a phosphorescent compound. For reference, in the case of a fluorescent material, luminescence attributable to the compound does not disappear even in an oxygen-aerated solution.

Further, in contrast with a fluorescent material generally showing a luminescence life of several nsec to several tens of nsec, the compounds of the present invention including those obtained in the following Examples, all exhibited a phosphorescence life of 100 nsec or longer.

EXAMPLE 2

Example Compound No. 310 was synthesized through a similar process as in Example 1.

Luminescence of toluene solution: λmax=489 nm
MALDI-TOF MS: $M^+$=859.1

EXAMPLE 3

Example Compound No. 238 was synthesized through a similar process as in Example 1.

Luminescence of toluene solution: λmax=515 nm
MALDI-TOF MS: $M^+$=709.1

EXAMPLE 4

Example Compound No. 242 was synthesized through a similar process as in Example 1.

Luminescence of toluene solution: λmax=471 nm
MALDI-TOF MS: $M^+$=763.1

EXAMPLE 5

Example Compound No. 384 was synthesized through a similar process as in Example 1.

Luminescence of toluene solution: λmax=466 nm
MALDI-TOF MS: $M^+$=913.1

EXAMPLE 6

Example Compound No. 777 was synthesized through a similar process as in Example 1.

Luminescence of toluene solution: max=696 nm MALDI-TOF MS: $M^+$=1231.1

EXAMPLE 7

Example Compound No. 472 was synthesized.

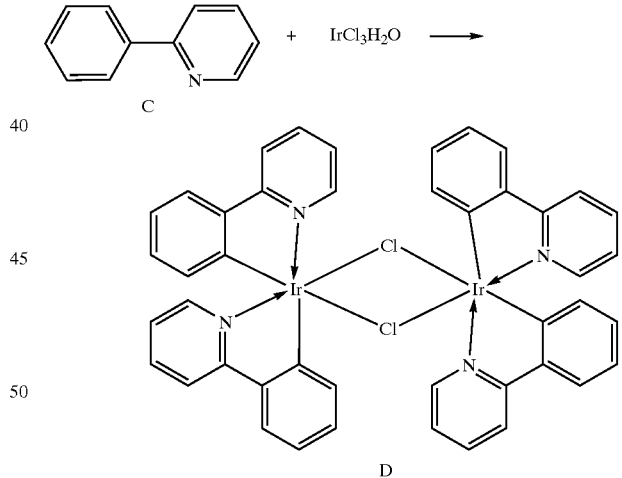

In a 100 ml-two-necked flask, 60 ml of ethoxyethanol and 20 ml of $H_2O$ were placed and stirred for 1 hour under bubbling with nitrogen. Then, 0.51 g (4.4 mmol) of Compound C and 0.71 g (2.0 mmol) of iridium (III) trichloride hydrate were added, and the system was heated for 16 hours around 100° C. under stirring and nitrogen stream. The reaction product was cooled to room temperature and poured into 100 ml of water, followed by recovery by filtration and washing with water of the precipitate. The precipitate was then poured into 60 ml of ethanol and stirred for 1 hour, followed by filtering-out and washing with acetone, to obtain 0.95 g (yield: 89%) of yellow powdery Compound D.

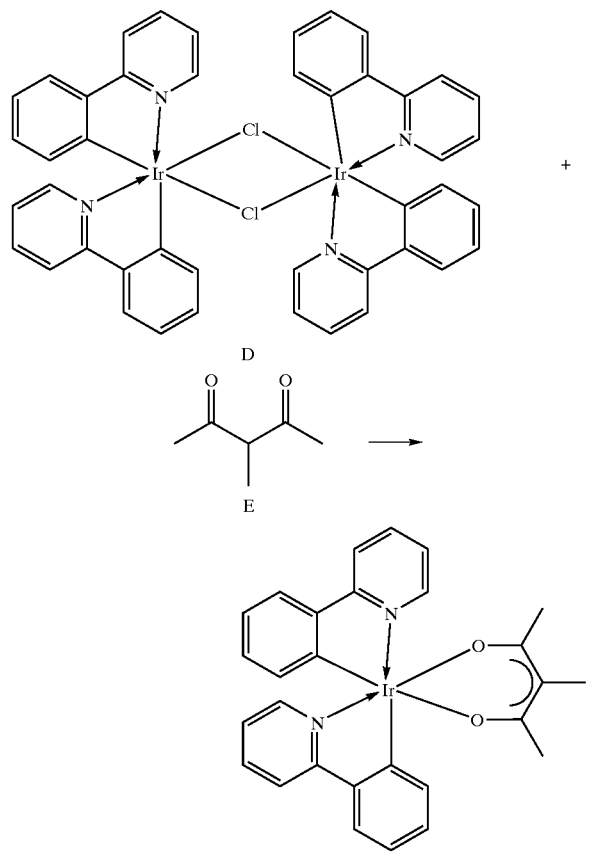

In a 100 ml-two-necked flask, 50 ml of ethoxyethanol was placed and stirred for 1 hour under bubbling with nitrogen. Then, 0.536 g (0.5 mmol) of Compound D, 0.17 g (1.4 mmol) of Compound E and 0.75 g of sodium carbonate Na$_2$CO$_3$ were added, and the system was heated for 16 hours around 100° C. under stirring and nitrogen stream. The reaction product was cooled to room temperature and poured into 100 ml of water, followed by filtering-out and washing with water of the precipitate. The precipitate was poured into 70 ml of ethanol, and after stirring for 1 hour, the precipitate was filtered out and dissolved in chloroform, followed by filtration. The resultant filtrate was condensed, and purified by silica gel column chromatography with chloroform as eluent to obtain 0.45 g (yield: 73%) of yellow powdery Example Compound No. 472. A toluene solution of the compound exhibited a luminescence spectrum showing λmax=526 nm. The compound exhibited M$^+$=614.2 according to MALDI-TOF MS and was confirmed to be the objective product.

EXAMPLE 8

In this Example, a device (effective display area=3 mm$^2$) having a device structure including 4 organic layers as shown in FIG. 1(c) was prepared. An alkali-free glass sheet was used as a transparent substrate 15 and a 100 nm-thick indium tin oxide (ITO) film was formed by sputtering and patterned as a transparent electrode 14. Further, α-NPD represented by the above-mentioned structural formula was vacuum-deposited in a layer thickness of 40 nm thereon as a hole-transporting layer 13. Then, as an organic luminescence layer 12, the above-mentioned CBP as a host material and Example Compound No. 729 (metal coordination compound) in an amount of providing 8 wt. % were co-vacuum deposited in a layer thickness of 30 nm. Further, as an exciton diffusion-prevention layer 17, BCP was vacuum-deposited in a thickness of 10 nm. Then, as an electron-transporting layer 16, the above-mentioned Alq3 was subjected to resistance heating vacuum deposition at a vacuum of 10$^{-4}$ Pa to form an organic film in a thickness of 30 nm.

On the above, as a lower layer of a metal electrode layer 11, an AlLi alloy film was disposed in a thickness of 15 nm, and a 100 nm-thick Al film was vacuum-deposited thereon to form a patterned metal electrode 11 disposed opposite to the transparent electrode 14 and having an electrode area of 3 mm$^2$.

The performances of the thus-obtained EL device were measured by using a micro-current meter ("4140B", made by Hewlett-Packard Corp.) for a current-voltage characteristic and "BM7" (made by Topcon K.K.) for an emission luminance.

EXAMPLE 9

A device was prepared in the same manner as in Example 8 except using a metal coordination compound (Example Compound No. 729) was used in a weight ratio of 7 wt. %.

COMPARATIVE EXAMPLE 1

A device was prepared in the same manner as in Example 8 except for using a metal coordination compound (729R) shown in Table 2 (wherein a substituted compound of the present invention to be compared therewith is shown in parallel) in a weight ratio of 8 wt. %.

TABLE 2

| No | M | N | m | A | B | A-R1 | A-R2 | A-R3 | A-R4 | B-R5 | B-R6 | B-R7 | B-R8 |
|---|---|---|---|---|---|---|---|---|---|---|---|---|---|
| 729R | Ir | 3 | 0 | Tn1 | P1 | H | H | — | — | H | H | H | H |
| 729 | Ir | 3 | 0 | Tn1 | P1 | H | H | — | — | H | H | CF$_3$ | H |

COMPARATIVE EXAMPLE 2

A device was prepared in the same manner as in Example 8 except for using the metal coordination compound (729R) shown in Table 2 in a weight ratio of 3 wt. %.

COMPARATIVE EXAMPLE 3

A device was prepared in the same manner as in Example 8 except for using the metal coordination compound (729R) shown in Table 2 in a weight ratio of 1 wt. %.

Each device was supplied with an electric field of 12 volts/100 nm with the ITO side as the anode and the Al side as the cathode to measure a luminance.

In order to remove factors for device deterioration due to oxygen or water, the above measurement was performed in a dry nitrogen flow after taking the device out of the vacuum chamber.

The results of devices using the respective compounds are shown in Table 3. As is understood from the results shown in Table 3, the maximum luminance concentration of Comparative Compound 729R was clearly between 1% and 8%, whereas Example Compound No. 729 provided with a substituent exhibited a higher luminance at 8% than at 7% and could exhibit a substantially higher luminance at 8% than 729R having no substituent.

TABLE 3

<Luminance comparison>

| Example | Compound No. | Concentration (wt. %) | Luminance (cd/m$^2$) |
|---|---|---|---|
| 8 | 729 | 8 | 4500 |
| 9 | 729 | 7 | 4250 |
| Comp. 1 | 729R | 8 | 1620 |
| Comp. 2 | 729R | 3 | 4000 |
| Comp. 3 | 729R | 1 | 1290 |

EXAMPLE 10

A device was prepared in the same manner as in Example 8 except for using a metal coordination compound (310) synthesized in Example 2 in a weight ratio of 3 wt. %.

EXAMPLE 11

A device was prepared in the same manner as in Example 8 except for using a metal coordination compound (310) synthesized in Example 2 in a weight ratio of 6 wt. %.

EXAMPLE 12

A device was prepared in the same manner as in Example 8 except for using a metal coordination compound (310) synthesized in Example 2 in a weight ratio of 8 wt. %.

EXAMPLE 13

A device was prepared in the same manner as in Example 8 except for using a metal coordination compound (238) synthesized in Example 3 in a weight ratio of 3 wt. %.

EXAMPLE 14

A device was prepared in the same manner as in Example 8 except for using a metal coordination compound (238) synthesized in Example 3 in a weight ratio of 6 wt. %.

EXAMPLE 15

A device was prepared in the same manner as in Example 8 except for using a metal coordination compound (238) synthesized in Example 3 in a weight ratio of 8 wt. %.

EXAMPLE 15A

A device was prepared in the same manner as in Example 8 except for using a metal coordination compound (238) synthesized in Example 3 in a weight ratio of 11 wt. %

EXAMPLE 15B

A device was prepared in the same manner as in Example 8 except for using a metal coordination compound (238) synthesized in Example 3 in a weight ratio of 13 wt. %.

EXAMPLE 16

A device was prepared in the same manner as in Example 8 except for using a metal coordination compound (242) synthesized in Example 4 in a weight ratio of 3 wt. %.

EXAMPLE 17

A device was prepared in the same manner as in Example 8 except for using a metal coordination compound (242) synthesized in Example 4 in a weight ratio of 6 wt. %.

EXAMPLE 18

A device was prepared in the same manner as in Example 8 except for using a metal coordination compound (242) synthesized in Example 4 in a weight ratio of 8 wt. %.

EXAMPLE 19

A device was prepared in the same manner as in Example 8 except for using a metal coordination compound (384) synthesized in Example 5 in a weight ratio of 3 wt. %.

EXAMPLE 20

A device was prepared in the same manner as in Example 8 except for using a metal coordination compound (384) synthesized in Example 5 in a weight ratio of 6 wt. %.

EXAMPLE 21

A device was prepared in the same manner as in Example 8 except for using a metal coordination compound (384) synthesized in Example 5 in a weight ratio of 8 wt. %.

COMPARATIVE EXAMPLE 4

A device was prepared in the same manner as in Example 8 except for using a metal coordination compound (1R) shown in Table 4 (wherein structures of the corresponding Example Compound Nos. 310, 238, 242 and 384 are shown in parallel) in a weight ratio of 3 wt. %

TABLE 4

| No | M | m | n | A | B | A-R1 | A-R2 | A-R3 | A-R4 | B-R5 | B-R6 | B-R7 | B-R8 |
|---|---|---|---|---|---|---|---|---|---|---|---|---|---|
| 1R | Ir | 3 | 0 | Ph | P1 | H | H | H | H | H | H | H | H |
| 310 | Ir | 3 | 0 | Ph | P1 | H | CF$_3$ | H | H | H | H | H | H |
| 238 | Ir | 3 | 0 | Ph | P1 | H | F | H | H | H | H | H | H |
| 242 | Ir | 3 | 0 | Ph | P1 | F | H | F | H | H | H | H | H |
| 384 | Ir | 3 | 0 | Ph | P1 | H | CF$_3$ | F | H | H | H | H | H |

COMPARATIVE EXAMPLE 5

A device was prepared in the same manner as in Example 8 except for using the metal coordination compound (1R) shown in Table 4 in a weight ratio of 6 wt. %.

COMPARATIVE EXAMPLE 6

A device was prepared in the same manner as in Example 8 except for using the metal coordination compound (1R) shown in Table 4 in a weight ratio of 8 wt. %.

Each device of Examples 10–12 and Comparative Examples 4–6 was supplied with an electric field of 12 volts/100 nm with the ITO side as the anode and the Al side as the cathode to measure a current efficiency.

The results of devices using the respective compounds are shown in Table 5. As is understood from the results shown in Table 5, the concentration giving a maximum current efficiency of Comparative Compound 1R was clearly between 3% and 8%, whereas Example Compound No. 310 provided with a substituent exhibited an increase in current efficiency even at 8%.

TABLE 5

<Comparison of current efficiency>

| Example | Compound No. | Concentration (wt. %) | Current Eff. (cd/A) |
|---|---|---|---|
| 10 | 310 | 3 | 2 |
| 11 | 310 | 6 | 2.4 |
| 12 | 310 | 8 | 2.7 |
| Comp. 4 | 1R | 3 | 15 |
| Comp. 5 | 1R | 6 | 19 |
| Comp. 6 | 1R | 8 | 17 |

Each device of Examples 13–15 and Comparative Examples 4–6 was supplied with a voltage of 12 volts/100 nm with the ITO side as the anode and the Al side as the cathode to measure an (electric) power efficiency.

The results of the devices using the respective compounds are shown in Table 6. As is understood from the results shown in Table 6, the concentration giving a maximum power efficiency of the Comparative Compound 1 R was between 3% and 8%, whereas Example Compound (238) provided with a substituent showed an increase in maximum efficiency even at a concentration of 8%.

TABLE 6

<Comparison of power efficiency>

| Example | Compound No. | Concentration (wt. %) | Power efficiency (lm/W) |
|---|---|---|---|
| 13 | 238 | 3 | 5.4 |
| 14 | 238 | 6 | 6 |
| 15 | 238 | 8 | 6.2 |
| 15A | 238 | 11 | 6.5 |
| 15B | 238 | 13 | 6.3 |
| Comp. 4 | 1R | 3 | 5.7 |
| Comp. 5 | 1R | 6 | 6.2 |
| Comp. 6 | 1R | 8 | 6 |

Each device of Examples 16–18 and Comparative Examples 4–6 was supplied with a voltage of 12 volts/100 nm with the ITO side as the anode and the Al side as the cathode to measure an external quantum efficiency, which was evaluated in terms of a ratio of luminance (lm)/current (mA) based on a value of current passing through the device by using a micro-current passing through the device by using a micro-current meter ("4140B", made by Hewlett-Packard Corp.) and a value of luminance measured by "BM7" (made by Topcon K.K.).

The results of the devices using the respective compounds are shown in Table 7. As is understood from the results shown in Table 7, the concentration giving a maximum external quantum efficiency of the Comparative Compound 1R was between 3% and 8%, whereas Example Compound (242) provided with a substituent showed an increase in maximum efficiency even at a concentration of 8%.

TABLE 7

<Comparison of external quantum efficiency>

| Example | Compound No. | Concentration (wt. %) | Ext. quantum efficiency |
|---|---|---|---|
| 16 | 242 | 3 | 3 |
| 17 | 242 | 6 | 4 |
| 18 | 242 | 8 | 4.2 |
| Comp. 4 | 1R | 3 | 7 |
| Comp. 5 | 1R | 6 | 8 |
| Comp. 6 | 1R | 8 | 7.6 |

Each device of Examples 19–21 and Comparative Examples 4–6 was supplied with a voltage of 12 volts/100 nm with the ITO side as the anode and the Al side as the cathode to measure an (electric) power efficiency.

The results of the devices using the respective compounds are shown in Table 8. As is understood from the results shown in Table 8, the concentration giving a maximum power efficiency of the Comparative Compound 1R was between 3% and 8%, whereas Example Compound (384) provided with a substituent showed an increase in maximum efficiency even at a concentration of 8%.

TABLE 8

<Comparison of power efficiency>

| Example | Compound No. | Concentration (wt. %) | Power efficiency (lm/W) |
|---|---|---|---|
| 19 | 384 | 3 | 2 |
| 20 | 384 | 6 | 2.3 |
| 21 | 384 | 8 | 2.6 |
| Comp. 4 | 1R | 3 | 5.7 |
| Comp. 5 | 1R | 6 | 6.2 |
| Comp. 6 | 1R | 8 | 6 |

EXAMPLE 22

A device was prepared in the same manner as in Example 8 except for using a metal coordination compound (777) synthesized in Example 6 in a weight ratio of 1 wt. %.

EXAMPLE 23

A device was prepared in the same manner as in Example 8 except for using a metal coordination compound (777) synthesized in Example 6 in a weight ratio of 6 wt. %.

EXAMPLE 24

A device was prepared in the same manner as in Example 8 except for using a metal coordination compound (777) synthesized in Example 6 in a weight ratio of 8 wt. %.

COMPARATIVE EXAMPLE 7

A device was prepared in the same manner as in Example 8 except for using a metal coordination compound (777R) shown in Table 9 below in a weight ratio of 1 wt. %.

TABLE 9

| No | M | m | n | A | B | A-R1 | A-R2 | A-R3 | A-R4 | B-R5 | B-R6 | B-R7 | B-R8 |
|---|---|---|---|---|---|---|---|---|---|---|---|---|---|
| 777R | Ir | 3 | 0 | Pe | P1 | H | H | H | H | H | H | H | H |
| 777 | Ir | 3 | 0 | Pe | P1 | H | H | H | H | H | H | $CF_3$ | H |

COMPARATIVE EXAMPLE 8

A device was prepared in the same manner as in Example 8 except for using the metal coordination compound (777R) shown in Table 9 in a weight ratio of 6 wt. %.

COMPARATIVE EXAMPLE 9

A device was prepared in the same manner as in Example 8 except for using the metal coordination compound (777R) shown in Table 9 in a weight ratio of 8 wt. %.

Each device of Examples 22–25 and Comparative Examples 7–9 was supplied with a voltage of 12 volts/100 nm with the ITO side as the anode and the Al side as the cathode to measure an (electric) power efficiency.

The results of the devices using the respective compounds are shown in Table 10. As is understood from the results shown in Table 6, the concentration giving a maximum power efficiency of Comparative Compound 777R was between 1% and 8%, whereas Example Compound (777) provided with a substituent showed an increase in maximum efficiency up to a concentration of 8%.

TABLE 10

<Comparison of maximum power efficiency>

| Example | Compound No. | Concentration (wt. %) | Power efficiency (lm/W) |
| --- | --- | --- | --- |
| 22 | 777 | 1 | 0.04 |
| 23 | 777 | 6 | 0.12 |
| 24 | 777 | 8 | 0.15 |
| Comp. 7 | 777R | 1 | 0.08 |
| Comp. 8 | 777R | 6 | 0.15 |
| Comp. 9 | 777R | 8 | 0.13 |

EXAMPLE 25

A device was prepared in the same manner as in Example 8 except for using a metal coordination compound (472) synthesized in Example 7 in a weight ratio of 3 wt. %.

EXAMPLE 26

A device was prepared in the same manner as in Example 1 except for using a metal coordination compound (472) synthesized in Example 7 in a weight ratio of 6 wt. %.

COMPARATIVE EXAMPLE 10

A device was prepared in the same manner as in Example 1 except for using a metal coordination compound (472R) shown below in a weight ratio of 3 wt. %.

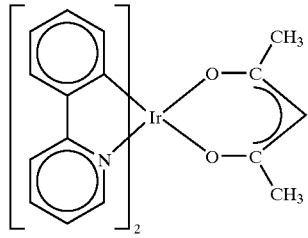

COMPARATIVE EXAMPLE 11

A device was prepared in the same manner as in Example 1 except for using the above metal coordination compound (472R) in a weight ratio of 6 wt. %.

COMPARATIVE EXAMPLE 12

A device was prepared in the same manner as in Example 1 except for using the above metal coordination compound (472R) in a weight ratio of 8 wt. %.

Each device of Examples 25–27 and Comparative Examples 10–12 was supplied with an electric field of 12 volts/100 nm with the ITO side as the anode and the Al side as the cathode to measure a power efficiency.

In order to remove factors for device deterioration due to oxygen or water, the above measurement was performed in a dry nitrogen flow after taking the device out of the vacuum chamber.

The results of devices using the respective compounds are shown in Table 11. As is understood from the results shown in Table 11, the concentration giving a maximum power efficiency of Comparative Compound 1R was clearly between 3% and 8%, whereas Example Compound (384) provided with a substituent exhibited an increase in power efficiency even at a concentration of 8%.

TABLE 11

<Comparison of maximum power efficiency>

| Example | Compound No. | Concentration (wt. %) | Power efficiency (lm/W) |
| --- | --- | --- | --- |
| 25 | 472 | 3 | 5.6 |
| 26 | 472 | 6 | 6.3 |
| 27 | 472 | 8 | 6.5 |
| Comp. 10 | 472R | 3 | 5.4 |
| Comp. 11 | 472R | 6 | 6 |
| Comp. 12 | 472R | 8 | 5.8 |

EXAMPLE 28

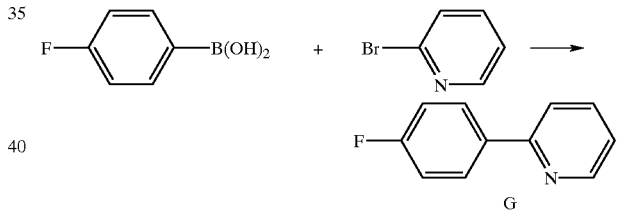

In a 200 ml-three-necked flask, 3.50 g (25.0 mmol) of 4-fluorophenylboronic acid, 3.95 g (25.0 mmol) of 1-bromopyridine, 25 ml of toluene, 12.5 ml of ethanol and 25 ml of 2M-sodium carbonate aqueous solution, were placed and stirred at room temperature under a nitrogen stream, followed by addition of 0.98 g (0.85 mmol) of tetrakis(triphenylphosphine)palladium (0). Thereafter, the system was refluxed under stirring and nitrogen stream for 8 hours. After completion of the reaction, the reaction product was cooled and extracted by adding cold water and toluene. The organic layer was washed with saline water and dried on magnesium sulfate, followed by removal of the solvent under a reduced pressure to provide a dry solid. The residue was purified by silica gel column chromatography (eluent: chloroform/methanol=10/1) to obtain 3.24 g (yield=75%) of Compound G.

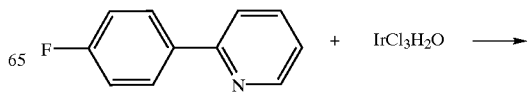

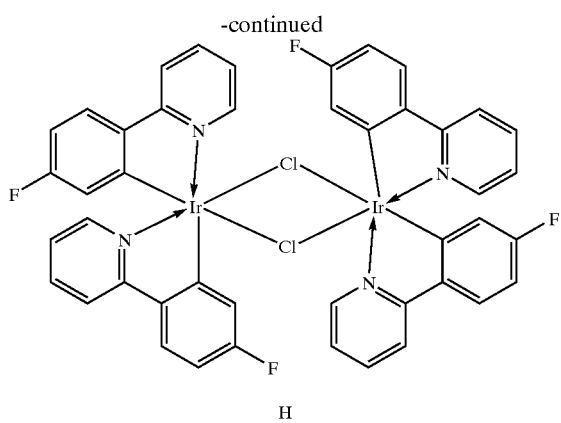

H

In a 200 ml-three-necked, 0.881 g (2.5 mmol) of iridium (III) chloride trihydrate, 0.953 g (5.5 mmol), 75 ml of ethoxyethanol and 25 ml of water were placed and stirred for 30 min. at room temperature under nitrogen stream, followed by 24 hours of reflux under stirring. The reaction product was cooled to room temperature, and the precipitate was recovered by precipitation and washed successively with water, ethanol and acetone. After being dried at room temperature under a reduced pressure, 1.32 g (yield: 92%) of yellow powdery Compound H was obtained.

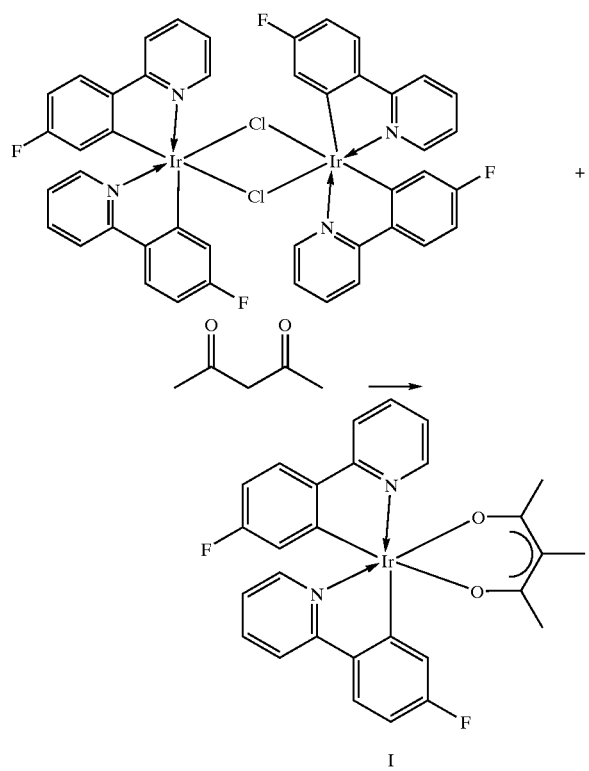

I

In a 200 ml-three-necked flask, 70 ml of ethoxyethanol, 0.80 g (0.7 mmol) of Compound H, 0.22 g (2.10 mmol) of acetylacetone and 1.04 g (9.91 mmol) of sodium carbonate, were placed and stirred for 1 hour at room temperature under a nitrogen stream, followed by 15 hours of reflux under stirring. The reaction product was cooled with ice, and the precipitate was filtered out and washed with water. The precipitate was purified by silica gel chromatography (eluent: chloroform/methanol=30/1) to obtain 0.63 g (yield: 71%) of yellow powdery Compound I (Example Compound No. 489). A toluene solution of the compound exhibited a luminescence spectrum showing λmax=499 nm. Further, according to MALDI-TOF MS, $M^+$=638.7 of the compound was confirmed.

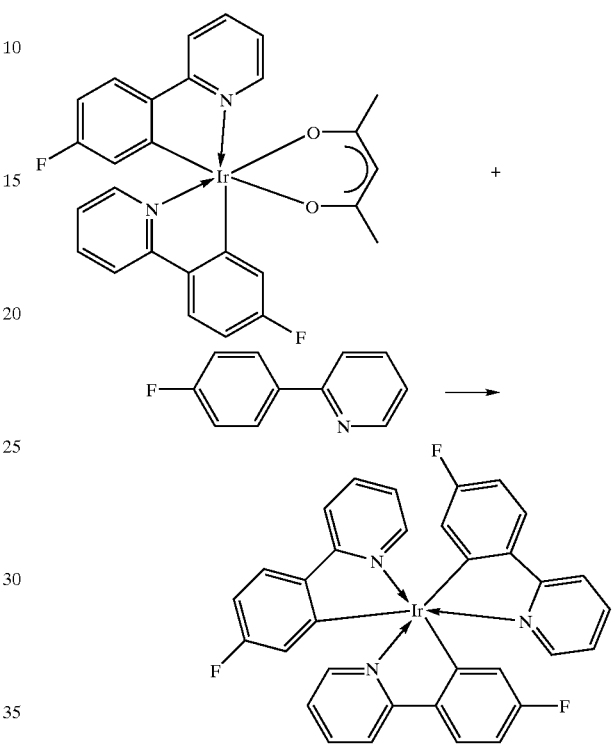

In a 100 ml-three-necked flask, 0.21 g (1.2 mmol) of Compound G, 0.32 g (0.5 mmol) of Compound I and 25 ml of glycerol, were placed and stirred for 8 hours around 180° C. under a nitrogen stream. The reaction product was cooled to room temperature and poured into 170 ml of 1N-hydrochloric acid. The precipitate was filtered out and washed with water, followed by drying for 5 hours at 100° C. under a reduced pressure. The precipitate was purified by silica gel column chromatography with chloroform as the eluent to obtain 0.22 g (yield: 63%) of yellow powdery Example Compound No. 239. A toluene solution of the compound exhibited a luminescence spectrum showing λmax=490 nm, and $M^+$=708.8 of the compound was confirmed by MALDI-TOF MS.

EXAMPLE 29

Example Compound No. 535 was synthesized through a similar process as in Example 7.

Luminescence of toluene solution: λmax=525 nm
MALDI-TOF MS: $M^+$=671.1

EXAMPLE 30

Example Compound No. 243 was synthesized through a similar process as in Example 28.

Luminescence of toluene solution: λmax=518 nm
MALDI-TOF MS: $M^+$=762.7

EXAMPLE 31

Example Compound No. 511 was synthesized through a similar process as in Example 7.

Luminescence of toluene solution: λmax=514 nm
MALDI-TOF MS: M+=628.1

EXAMPLE 32

Example Compound No. 56 was synthesized through a similar process as in Example 28.
Luminescence of toluene solution: λmax=505 nm
MALDI-TOF MS: M+=697.2

EXAMPLE 33

Example Compound No. 389 was synthesized through a similar process as in Example 1.
Luminescence of toluene solution: λmax=503 nm

EXAMPLE 34

Example Compound No. 390 was synthesized through a similar process as in Example 1.
Luminescence of toluene solution: λmax=507 nm

EXAMPLE 35

Example Compound No. 312 was synthesized through a similar process as in Example 1.
The Luminescence of toluene solution exhibited two peaks at 458 nm and 488 nm.

EXAMPLE 36

Example Compound No. 312 is synthesized through a similar process as in Example 1.

EXAMPLE 37

Example Compound No. 314 is synthesized through a similar process as in Example 1.

EXAMPLE 38

Example Compound No. 388 is synthesized through a similar process as in Example 1.

EXAMPLE 39

Example Compound No. 392 is synthesized through a similar process as in Example 1.

EXAMPLE 40

Example Compound Nos. 274, 346, 358, 393 and 396 can be synthesized through a similar process except for changing the starting material.

EXAMPLE 41

Figure 2:
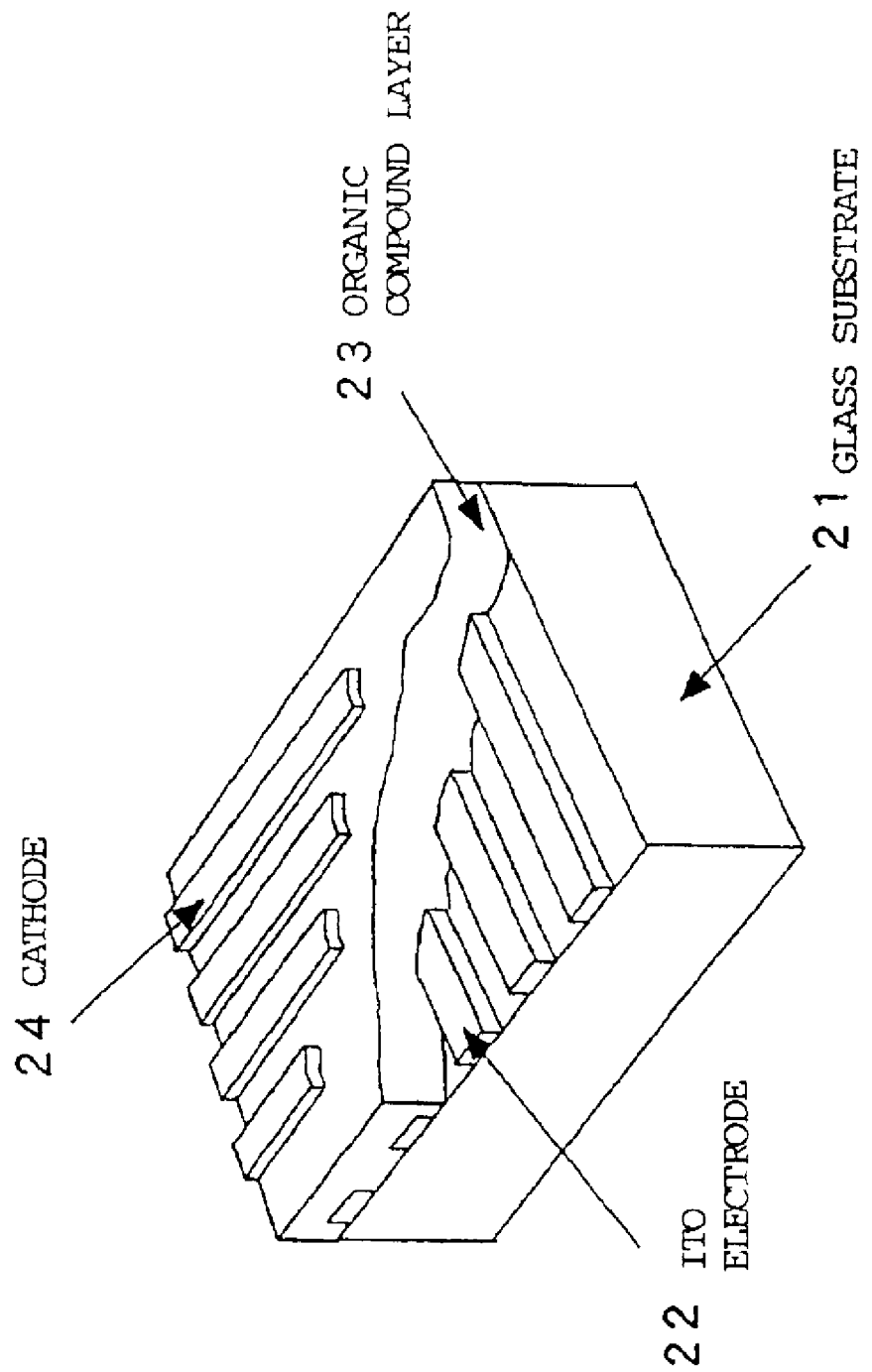
FIG. 2 illustrates a simple matrix-type organic EL device according to Example 28.

Hereinbelow, two examples of display apparatus are described. First, an example of preparation of a picture display apparatus having an XY-matrix structure is described with reference to FIG. 2.

On a glass substrate 21 measuring 150 mm-length, 150 mm-width and 1.1 mm-thickness, a ca. 100 nm-thick ITO film was formed by sputtering and patterned into 100 lines of 100 µm-wide transparent matrix electrodes (anode side) with a spacing of 40 µm as simple matrix electrodes. Then, a four-layered organic compound layer 23 was formed thereon including a luminescence layer 12 containing one of the compounds synthesized in Examples 1–7 as a guest compound.

Then, 100 lines of 100 µm-wide metal electrodes 24 were formed with a spacing of 40 µm by mask vacuum deposition so as to be perpendicular to the transparent electrodes by vacuum deposition at a vacuum of $2 \times 10^{-5}$ Torr. The metal electrodes were formed as a lamination of 10 nm-thick layer of Al/Li alloy (Li: 1.3 wt. %) and then 150 nm-thick layer of Al.

Figure 3:
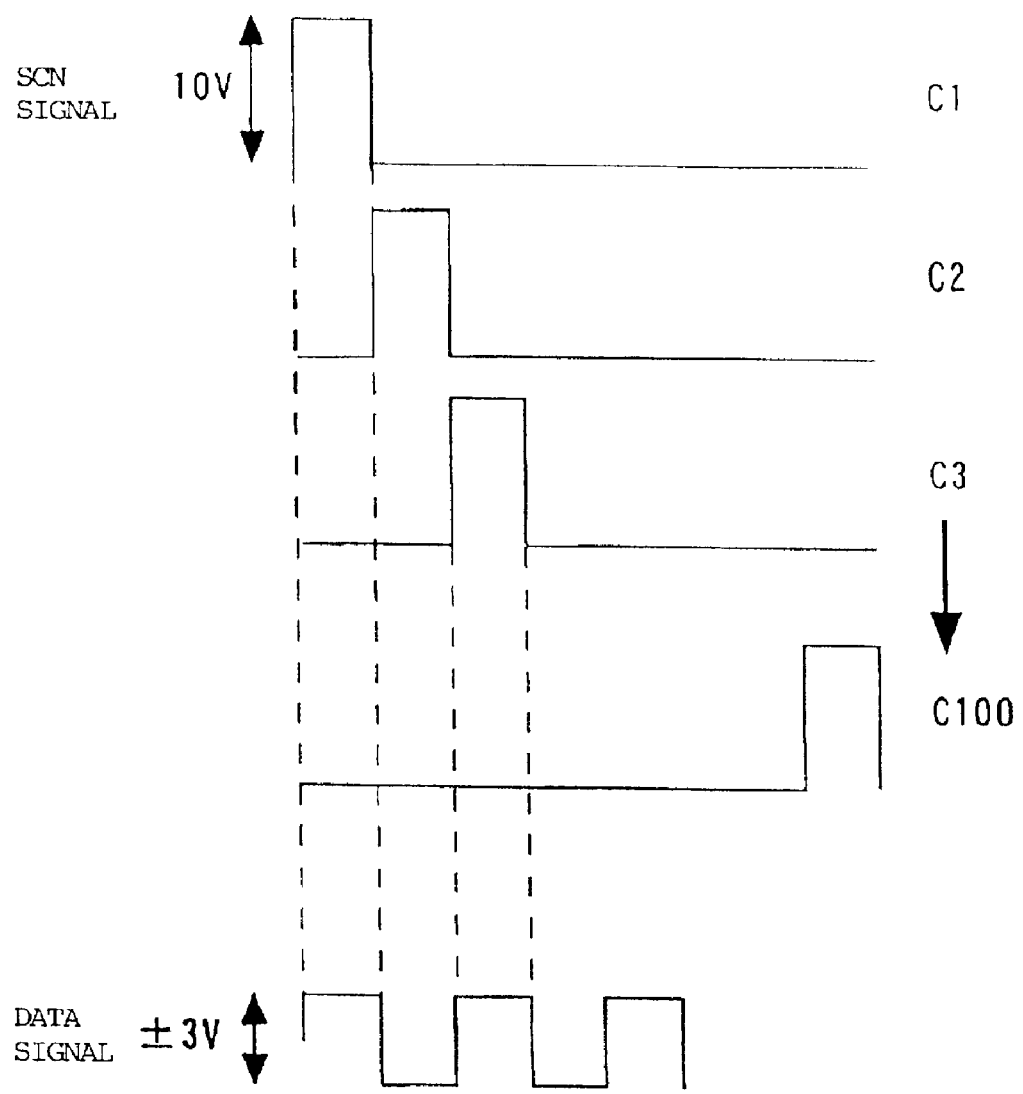
FIG. 3 illustrates drive signals used in Example 28.

The thus-obtained 100×100-simple matrix-type organic EL devices were subjected to a simple matrix drive in a glove box filled with nitrogen at voltages of 7 volts to 13 volts by using a scanning signal of 10 volts and data signals of ±3 volts as shown in FIG. 3. As a result of an interlaced drive at a frame frequency of 30 Hz, luminescence pictures were confirmed for the respective devices.

As a picture display apparatus, the high-efficiency luminescence device of the present invention allows a light-weight flat panel display with economized energy consumption and high-recognizability. As a printer light source, the luminescence devices of the present invention may be arranged in a line and disposed in proximity to the photosensitive drum, to provide a line shutter wherein the respective devices are driven independently from each other to effect prescribed exposure on the photosensitive drum. On the other hand, the energy consumption economization effect is expected in application as an illumination device or a backlight for a liquid crystal display apparatus.

For another application to a picture display device, it is particularly advantageous to form an active matrix-type picture display device equipped with thin film transistors (TFTs) instead of the above-mentioned XY-matrix wiring. Hereinbelow, an active matrix-type picture display device according to the present invention will be described with reference to FIGS. 4 to 6.

Figure 4:
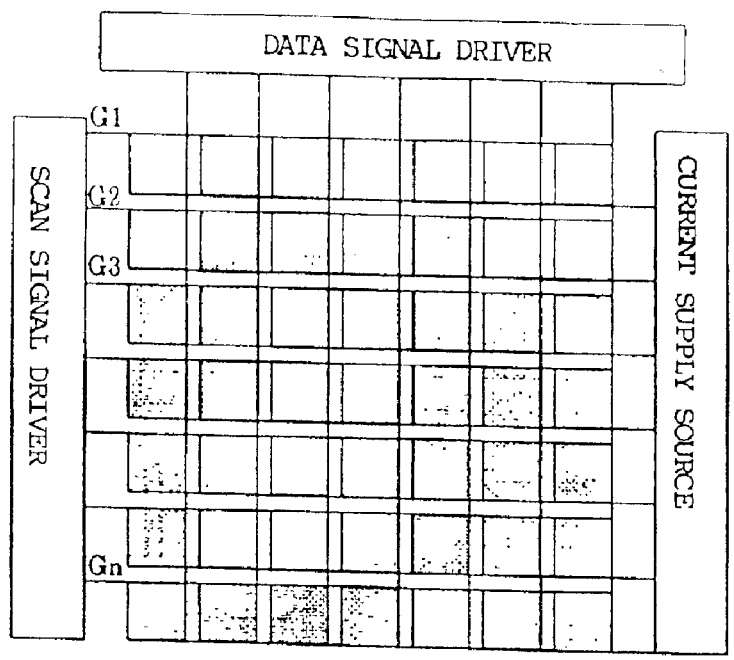
FIG. 4 schematically illustrates a panel structure including an EL device and drive means.
Figure 5:
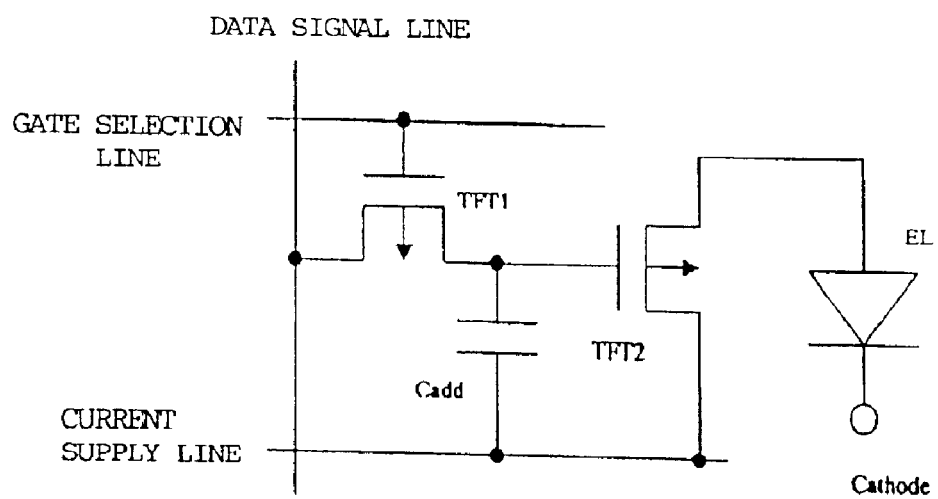
FIG. 5 illustrates an example of pixel circuit.

FIG. 4 is a schematic plan view of such a panel. Circumferentially outside the panel are disposed a drive circuit comprising a power supply source and a scanning signal driver, and a data signal driver as a display signal input means (called a picture data supply means, which are respectively connected to current supply lines, X-direction scanning lines called gate lines and Y-direction lines called data lines. The scanning signal driver sequentially selects the gate scanning lines, and in synchronism therewith, picture signals are supplied from the data signal driver. Display pixels are disposed at intersections of the gate scanning lines and the data lines.

Next, a pixel circuit operation is described with reference to an equivalent circuit. When a selection signal is applied to a gate selection line, TFT1 is turned on so that a data signal is supplied from a data signal line to a capacitor Cadd, thereby determining the gate potential of TFT2, whereby a current is supplied to an organic luminescence device (EL) disposed at each pixel through a current supply line depending on the gate potential of TFT2. The gate potential of TFT2 is held at Cadd during one frame period, so that the current continually flows from the current supply line to the EL device during the period. As a result, luminescence is retained during one frame period.

Figure 6:
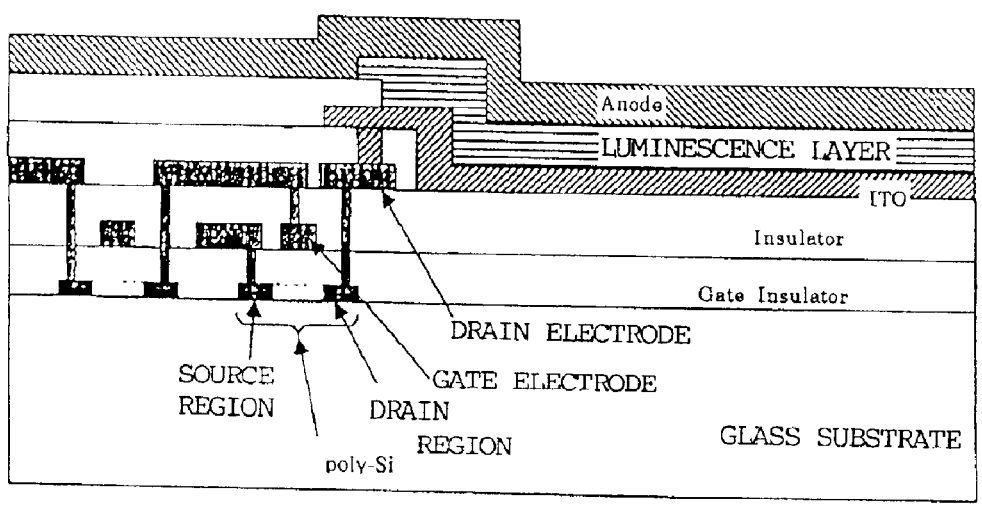
FIG. 6 is a schematic view showing an example of sectional structure of a TFT substrate.

FIG. 6 is a schematic view illustrating a sectional structure of a TFT used in this Example. On a glass substrate, a polysilicone p-Si layer is formed, and the channel, drain and source regions are doped with necessary impurities, respectively. Thereon, gate electrodes are formed via a gate. insulating film, and drain electrodes and source electrodes connected to the drain regions and source regions, respectively, are formed. In this instance, the drain electrodes and transparent pixel electrodes (ITO) are connected through contact holes bored in an intervening insulating film.

The active device used in the present invention need not be particularly restricted, and can also be a single-crystal silicon TFT, an amorphous silicon a-Si TFT, etc.

On the pixel electrodes, plural layers or a single layer of organic luminescence layer may be disposed and metal electrodes as cathode are sequentially laminated to provide an active-type organic luminescence device.

Industrial Applicability

As described above, a substituted metal coordination compound having a high phosphorescence efficiency and a short phosphorescence life can be used in a luminescence layer at a high concentration relative to the host material while preventing concentration extinction. As a result, according to the present invention, it is possible to obtain an excellent luminescence device showing high luminescence efficiency. The luminescence device of the present invention is also excellent as a display device.

What is claimed is:

1. An organic luminescence device, comprising:
   a pair of electrodes each disposed on a substrate; and
   at least one luminescence layer comprising an organic compound disposed between the electrodes,
   wherein the luminescence layer comprises a first organic compound and a phosphorescent second organic compound,
   wherein the second organic compound is present at a concentration of at least 8 wt. % in the luminescence layer, and
   wherein the second organic compound is a compound selected from the group consisting of compounds (9), (11), (29), (33), (34) and (42)–(49);

(9)

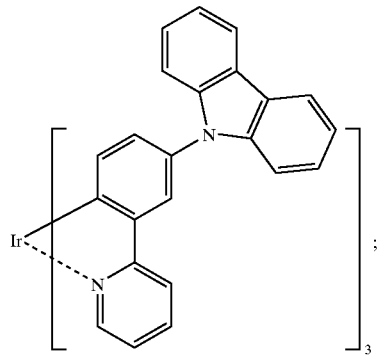

(11)

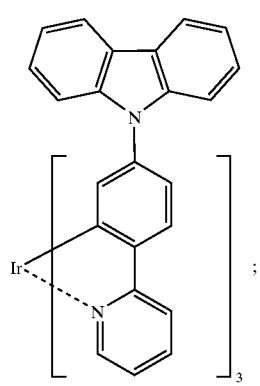

(29)

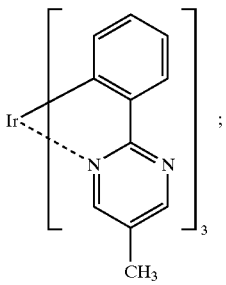

(33)

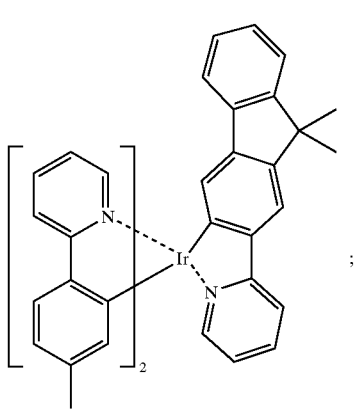

(34)

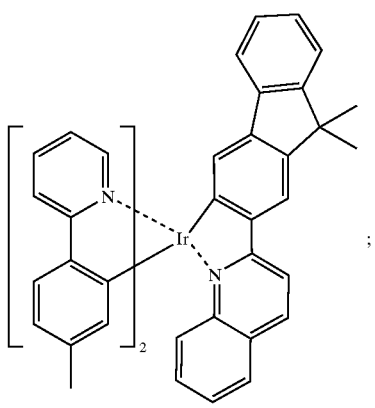

(42)

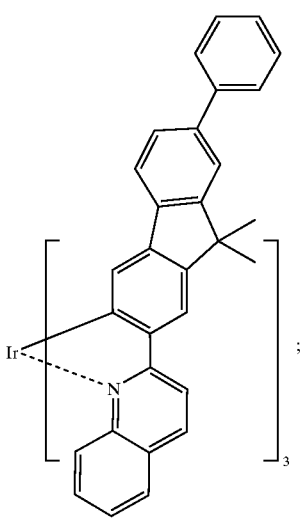

(43) 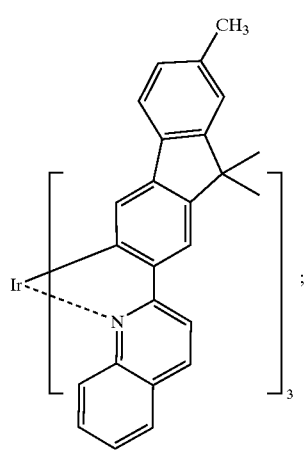
(44) 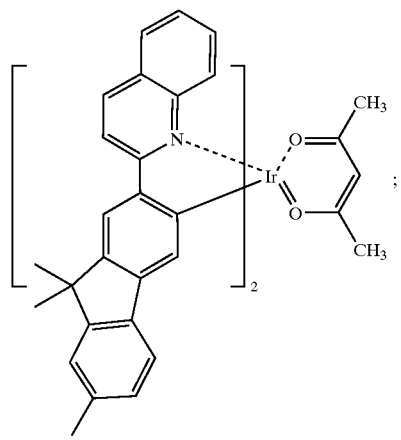
(45) 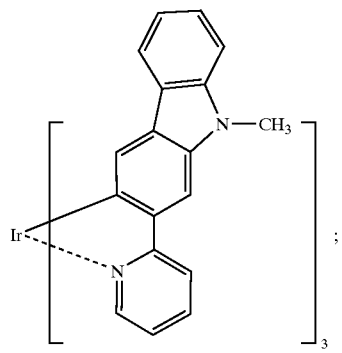
(46) 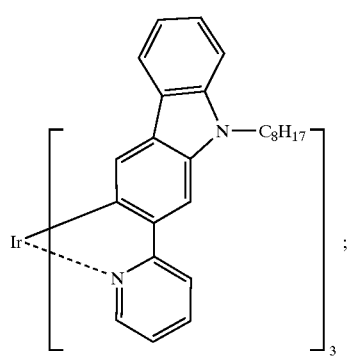
(47) 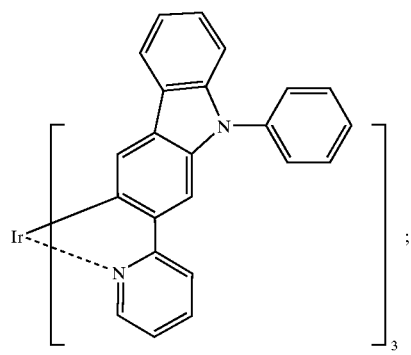
(48) 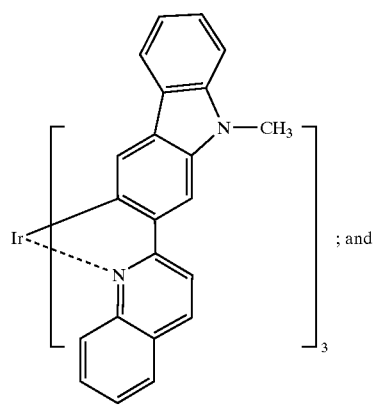
; and
(49) 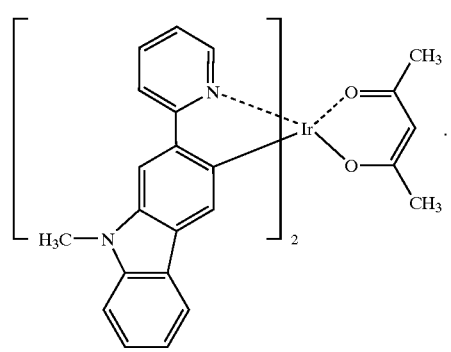
2. The organic luminescence device according to claim 1, wherein phosphorescence is emitted from the luminescence layer by applying a voltage between the electrodes.
3. A picture display apparatus, comprising:
an organic luminescence device according to claim 1; and
a drive circuit for supplying display data.
* * * * *